(12) United States Patent
Hyman et al.

(10) Patent No.: US 12,422,427 B2
(45) Date of Patent: Sep. 23, 2025

(54) COMPOUNDS FOR TREATMENT OF DISEASES AND METHODS OF SCREENING THEREFOR

(71) Applicant: Max-Planck-Gesellschaft zur Förderung der Wissenschaften e.V., Munich (DE)

(72) Inventors: Anthony A. Hyman, Dresden (DE); Richard J. Wheeler, Oxford (GB); Marc Bickle, Dresden (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 1400 days.

(21) Appl. No.: 16/653,874

(22) Filed: Oct. 15, 2019

(65) Prior Publication Data

US 2020/0150107 A1    May 14, 2020

Related U.S. Application Data

(63) Continuation of application No. PCT/EP2019/077818, filed on Oct. 14, 2019.

(30) Foreign Application Priority Data

Oct. 15, 2018 (EP) .................................... 18200401
Aug. 2, 2019 (EP) .................................... 19189772

(51) Int. Cl.
*G01N 33/53* (2006.01)
*G01N 33/50* (2006.01)

(52) U.S. Cl.
CPC ..... *G01N 33/5076* (2013.01); *C07K 2319/80* (2013.01); *C12Q 2600/142* (2013.01); *G01N 2800/2835* (2013.01)

(58) Field of Classification Search
None
See application file for complete search history.

(56) References Cited

U.S. PATENT DOCUMENTS

| | | | |
|---|---|---|---|
| 10,303,979 B2 | 5/2019 | Kraus et al. | |
| 11,340,231 B2 | 5/2022 | Szewczak et al. | |
| 11,493,519 B2 | 11/2022 | Beutel et al. | |
| 12,174,198 B2 | 12/2024 | Beutel | |
| 2007/0054353 A1 | 3/2007 | White et al. | |
| 2007/0178537 A1 | 8/2007 | Chiosis et al. | |
| 2007/0214509 A1 | 9/2007 | Langston | |
| 2009/0143433 A1 | 6/2009 | Hendrix | |
| 2009/0298910 A1 | 12/2009 | Griffey | |
| 2011/0281260 A1 | 11/2011 | Olson | |
| 2012/0100562 A1 | 4/2012 | Bourhis | |
| 2014/0080780 A1 | 3/2014 | Wolozin | |
| 2014/0121122 A1 | 5/2014 | Li | |
| 2014/0242602 A1 | 8/2014 | Chiosis et al. | |
| 2014/0287932 A1 | 9/2014 | Hnisz | |
| 2015/0045330 A1 | 2/2015 | Inoue et al. | |
| 2015/0164891 A1 | 6/2015 | Hornstein | |
| 2016/0235731 A1 | 8/2016 | Bradner | |
| 2016/0348180 A1 | 12/2016 | Al-murrani | |
| 2017/0198046 A1 | 7/2017 | Reiter | |
| 2017/0233762 A1 | 8/2017 | Zalatan | |
| 2017/0355977 A1 | 12/2017 | Brangwynne | |
| 2018/0009779 A1 | 1/2018 | Bradner | |
| 2018/0133168 A1 | 5/2018 | Hong et al. | |
| 2018/0251497 A1 | 9/2018 | Brangwynne | |
| 2018/0280407 A1 | 10/2018 | Warner | |
| 2018/0313827 A1 | 11/2018 | Baldwin et al. | |
| 2019/0127428 A1 | 5/2019 | Taylor | |
| 2019/0142860 A1 | 5/2019 | Larsen et al. | |
| 2019/0352648 A1 | 11/2019 | Young | |
| 2019/0382346 A1 | 12/2019 | Dalfo Capella | |
| 2020/0284801 A1 | 9/2020 | Beutel et al. | |
| 2021/0113525 A1 | 4/2021 | Okano et al. | |
| 2021/0208153 A1 | 7/2021 | Szewczak et al. | |
| 2021/0236532 A1 | 8/2021 | Okazawa | |
| 2021/0270844 A1 | 9/2021 | Saito et al. | |
| 2022/0112544 A1 | 4/2022 | Berman | |
| 2022/0120736 A1 | 4/2022 | Young et al. | |
| 2022/0365070 A1 | 11/2022 | Patel et al. | |

(Continued)

FOREIGN PATENT DOCUMENTS

CA    3001853 A1    4/2017
CN    107406842 A    11/2017

(Continued)

OTHER PUBLICATIONS

Adams, V.H et al. (2007). "Intrinsic Disorder and Autonomous Domain Function in the Multifunctional Nuclear Protein, MeCP2," Journal of Biological Chemistry 282(20): 15057-15064.

(Continued)

*Primary Examiner* — Michael D Pak
(74) *Attorney, Agent, or Firm* — MORRISON & FOERSTER LLP

(57) ABSTRACT

The present invention related to a compound for use in prevention or treatment of a neurodegenerative disease associated with the formation of stress granules. The compound is selected from lipoic acid, lipoamide, dihydrolipoic acid, and dihydrolipoamide. The invention further relates to a method of identifying a compound that modulates a characteristic associated with one or more condensates comprising a condensate-associated molecule, comprising: (a) contacting the compound with a cellular composition comprising one or more condensates or a cellular composition capable of forming one or more condensates, and (b) determining the characteristic associated with the one or more condensates. A modulation in the characteristic, as compared to a reference, indicates that the compound modulates the characteristic associated with the one or more condensates.

22 Claims, 35 Drawing Sheets

(56) References Cited

U.S. PATENT DOCUMENTS

| | | |
|---|---|---|
| 2022/0365093 A1 | 11/2022 | Szewczak et al. |
| 2022/0390432 A1 | 12/2022 | Young et al. |
| 2023/0176067 A1 | 6/2023 | Beutel et al. |
| 2023/0314443 A1 | 10/2023 | Mitrea et al. |
| 2024/0145034 A1 | 5/2024 | Chen |

FOREIGN PATENT DOCUMENTS

| | | |
|---|---|---|
| ES | 2338392 A1 | 5/2010 |
| JP | 2006509492 A | 3/2006 |
| JP | 2013544798 A | 12/2013 |
| JP | 2015506905 A | 3/2015 |
| JP | 2018050605 A | 4/2018 |
| JP | 2018117638 A | 8/2018 |
| JP | 2018531046 A | 10/2018 |
| KR | 20150112415 A | 10/2015 |
| KR | 20170092543 A | 8/2017 |
| WO | 0050872 A2 | 8/2000 |
| WO | WO2002038734 A2 | 5/2002 |
| WO | WO2002038734 A3 | 7/2002 |
| WO | 03040340 A2 | 5/2003 |
| WO | 2005099745 A2 | 10/2005 |
| WO | 2006070941 A1 | 7/2006 |
| WO | 2007071060 A1 | 6/2007 |
| WO | 2011093782 A1 | 8/2011 |
| WO | WO2011100374 A2 | 8/2011 |
| WO | WO2011100374 A3 | 12/2011 |
| WO | WO2012006551 A2 | 1/2012 |
| WO | 2012054565 A1 | 4/2012 |
| WO | WO2012006551 A3 | 4/2012 |
| WO | 2012162249 A1 | 11/2012 |
| WO | 2012167086 A2 | 12/2012 |
| WO | WO2014062686 A1 | 4/2014 |
| WO | WO2014066848 A1 | 5/2014 |
| WO | 2014145975 A2 | 9/2014 |
| WO | 2016097863 A1 | 6/2016 |
| WO | 2017068341 A1 | 4/2017 |
| WO | 2017204208 A1 | 11/2017 |
| WO | 2017207460 A1 | 12/2017 |
| WO | WO2018006074 A2 | 1/2018 |
| WO | WO2018006074 A3 | 2/2018 |
| WO | 2018043476 A1 | 3/2018 |
| WO | WO2018129544 A1 | 7/2018 |
| WO | 2018170794 A1 | 9/2018 |
| WO | 2019032613 A1 | 2/2019 |
| WO | WO2019084362 A2 | 5/2019 |
| WO | WO2019084362 A3 | 5/2019 |
| WO | WO2019109017 A1 | 6/2019 |
| WO | 2019146805 A1 | 8/2019 |
| WO | WO2019171068 A1 | 9/2019 |
| WO | WO2019183552 A2 | 9/2019 |
| WO | WO2019183552 A3 | 10/2019 |
| WO | WO2020037234 A1 | 2/2020 |
| WO | 2020078924 A1 | 4/2020 |
| WO | 2020163795 A1 | 8/2020 |
| WO | 2020232416 A1 | 11/2020 |
| WO | 2021055642 A2 | 3/2021 |
| WO | 2021055644 A1 | 3/2021 |
| WO | 2022035989 A1 | 2/2022 |
| WO | 2022187202 A1 | 9/2022 |
| WO | 2022187225 A1 | 9/2022 |
| WO | 2023023326 A1 | 2/2023 |
| WO | 2023068930 A1 | 4/2023 |
| WO | 2024030973 A1 | 2/2024 |
| WO | 2025014769 A1 | 1/2025 |

OTHER PUBLICATIONS

Alberti, S. (2017). "The Wisdom of Crowds: Regulating Cell Function Through Condensed States of Living Matter," J. Cell Sci. 130(17):2789-2796.

Alberti, S. (Oct. 23, 2017). "Phase Separation in Biology," Curr Biol. 27(20):R1097-R1102.

Alberti, S. et al. (Nov. 2, 2018). "A User's Guide for Phase Separation Assays With Purified Proteins." Journal of Molecular Biology 430(23):4806-4820.

Ali, M. et al. (May 22, 2018). "High-Throughput Discovery of Functional Disordered Regions," Molecular Systems Biology 14(5):e8377, 2 pages.

Allshire, R.C. et al. (Apr. 2018, e-pub. Dec. 13, 2017). "Ten Principles o Heterochromatin Formation and Function," Nature Reviews Molecular Cell Biology 19(4):229-244.

Amir, R.E. et al. (Oct. 1999). "Rett Syndrome Is Caused By Mutations in X-Linked MECP2, Encoding Methyl-CpG-Binding Protein 2," Nature Genetics, 23(2):185-188.

An, W.F. et al. (2009). "Introduction: Cell-Based Assays for High-Throughput Screening," Methods Mol Biol. 486:1-12.

Anderson, E.N. et al. (2018). "Traumatic Injury Induces Stress Granule Formation and Enhances Motor Dysfunctions in ALS/FTD Models," Hum. Mol. Genet. 27(8):1366-1381.

Ausio, J. et al. (2014). "MeCP2: The Long Trip From a Chromatin Protein to Neurological Disorders," Trends In Molecular Medicine 20(9):487-498.

Babu, M.M. et al. (Oct. 15, 2016). "The Contribution of Intrinsically Disordered Regions to Protein Function, Cellular Complexity, and Human Disease," Biochemical Society Transactions 44(5):1185-1200.

Bajar, B.T. et al. (Sep. 2016). "A Guide to Fluorescent Protein FRET Pairs," Sensors 16(9):1488, 24 pages.

Banani S.F. et al. (Jul. 28, 2016, e-pub. Jun. 30, 2016). "Compositional Control of Phase-Separated Cellular Bodies," Cell 166(3):651-663.

Banani, S.F. et al. (2017, e-pub. Feb. 22, 2017). "Biomolecular Condensates: Organizers of Cellular Biochemistry," Nat Rev Mol Cell Biol 18(5):285-298, 14 pages.

Bannister, A.J. et al. (2001). "Selective Recognition of Methylated Lysine 9 on Histone H3 by the HP1 Chromo Domain," Nature 410(6824):120-124.

Baron, D.M. et al. (Aug. 31, 2013). "Amyotrophic Lateral Sclerosis-Linked FUS/TLS Alters Stress Granule Assembly and Dynamics," Molecular Neurodegeneration 8(1):30, 18 pages.

Berry, J. et al. (Sep. 22, 2015, e-pub. Sep. 8, 2015). "RNA Transcription Modulates Phase Transition-Driven Nuclear Body Assembly," Proc Natl Acad Sci USA 112(38):E5237-E5245.

Best, R.B. (Feb. 2017). "Computational and Theoretical Advances in Studies of Intrinsically Disordered Proteins," Current Opinion in Structural Biology 42:147-154.

Boeynaems, S. et al. (Jun. 2018, e-pub. Mar. 27, 2018). "Protein Phase Separation: A New Phase in Cell Biology," Trends in Cell Biology 28(6):420-435.

Boija, A. et al. (Dec. 13, 2018, e-pub. Nov. 15, 2018). "Transcription Factors Activate Genes through the Phase-Separation Capacity of Their Activation Domains," Cell 175(7):1842-1855.

Bojcsuk, D. et al. (Apr. 20, 2017; e-pub. Dec. 19, 2016). "Inducible super-enhancers are organized based on canonical signal-specific transcription factor binding elements," Nucleic Acids Res. 45(7): 3693-3706.

Borggrefe, T. et al. (2011). "Interactions Between Subunits of the Mediator Complex With Gene-Specific Transcription Factors," Semin. Cell Dev. Biol. 22(7):759-768.

Bouchard J.J. et al. (Oct. 4, 2018, e-pub Sep. 20, 2018). "Cancer Mutations of the Tumor Suppressor SPOP Disrupt the Formation of Active," Phase-Separated Compartments. Mol Cell 72(1):19-36.

Boulay, G. et al. (2017). "Cancer-Specific Retargeting of BAF Complexes by a Prion-like Domain," Cell 171(1):163-178, 38 pages.

Boyd, J.D. et al. (Jan. 2014). "A High-Content Screen Identifies Novel Compounds That Inhibit Stress-Induced TDP-43 Cellular Aggregation and Associated Cytotoxicity." J Biomol Screen 19(1):44-56, 18 pages.

Bradner, J.E. et al. (2017). "Transcriptional Addiction in Cancer," Cell 168(4):629-643.

Brangwynne C.P. et al. (2013). "Phase Transitions and Size Scaling of Membrane-Less Organelles," J Cell Biol. 203(6):875-881.

(56) References Cited

OTHER PUBLICATIONS

Brangwynne, C.P. et al. (Jun. 26, 2009). "Germline P Granules Are Liquid Droplets That Localize By Controlled Dissolution/Condensation," Science 324:1729-1732.

Buckley D.L. et al. (2012). "Targeting the Von Hippel-Lindau E3 Ubiquitin Ligase Using Small Molecules to Disrupt the VHL/HIF-1 a Interaction," J Am Chem Soc. 134(10):4465-4468.

Burke, K.A. et al. (2015). "Residue-by-Residue View of In Vitro FUS Granules that Bind the C-Terminal Domain of RNA Polymerase II," Molecular Cell 60(2):231-241.

Carmony, K.C. et al. (2012). Chapter 44 in "PROTAC-Induced Proteolytic Targeting," Methods Mol Biol. 832, 11 pages.

Carroll J.S. et al. (2006). "Genome-Wide Analysis of Estrogen Receptor Binding Sites," Nat Genet 38(11):1289-1297.

Che, D.L. et al. (Oct. 16, 2015). "The Dual Characteristics of Light-Induced Cryptochrome 2, Homo-oligomerization and Heterodimerization, for Optogenetic Manipulation in Mammalian Cells," ACS Synth Biol. 4(10):1124-1135.

Cheutin, T. et al. (2003). "Maintenance of Stable Heterochromatin Domains By Dynamic HP1 Binding," Science 299 (5607):721-725.

Chiolo, I. et al. (2011). "Double-Strand Breaks in Heterochromatin Move Outside of a Dynamic HP1a Domain to Complete Recombinational Repair," Cell 144(5):732-744.

Cho W.K. et al. (2018). "Mediator and RNA Polymerase II Clusters Associate in Transcription-Dependent Condensates," Science 361(6400):412-415.

Cho, W.K. et al. (May 3, 2016). "RNA Polymerase II Cluster Dynamics Predict Mrna mRNA Output in Living Cells, RNA Polymerase II Cluster Dynamics Predict Mrna Output in Living Cells." Elife 5. pii: e13617, 31 pages.

Chong, S. et al. (2018). "Imaging Dynamic and Selective Low-Complexity Domain Interactions That Control Gene Transcription," Science 361(6400):eaar2555, 25 pages.

Cisse, I.I. et al. (Aug. 9, 2013). "Real-Time Dynamics of RNA Polymerase II Clustering in Live Human Cells," Science 341(6146):664-667.

Conway, E.L. (Jan. 1, 1998). "A Review of the Randomized Controlled Trials of Tacrine in the Treatment of Alzheimer's Disease: Methodologic Considerations," Clinical Neuropharmacol 21(1):8-17.

Conway, J.W. et al. (Feb. 7, 2005). "The Mammalian Mediator Complex," FEBS Lett. 579(4):904-908.

Dolgin, E. (Mar. 15, 2018). "Cell Biology's New Phase," Nature 555(7696):300-302, posted Dec. 17, 2018 on bioRXIV,http://www.cbeslm.cpaneldev.princeton.edu/wp-content/uploads/2019/01/NaturePhase.pdf.

Duan, L. et al. (Sep. 2017). "Understanding CRY2 Interactions for Optical Control of Intracellular Signaling," Nature Communications 8(1):1-10547, 10 pages.

Dubik D. et al. (Dec. 15, 1987). "Stimulation of C-Myc Oncogene Expression Associated With Estrogen-Induced Proliferation of Human Breast Cancer Cells," Cancer Res 47(24):6517-6521.

Ebmeier, C.C. et al. (Aug. 1, 2017). "Human TFIIH Kinase CDK7 Regulates Transcription-Associated Chromatin Modifications," Cell Rep 20(5):1173-1186.

Fang, M.Y. et al. (2009). "Small-Molecule Modulation of TDP-43 Recruitment to Stress Granules Prevents Persistent TDP-43 Accumulation in ALS/FTD," Neuron 103(5):802-819.

Fanning, S.W. et al. (2016). "Estrogen Receptor Alpha Somatic Mutations Y537S and D538G Confer Breast Cancer Endocrine Resistance by Stabilizing the Activating Function-2 Binding Conformation," Elife 5:e12792, 25 pages.

Festenstein, R. et al. (2003). "Modulation of Heterochromatin Protein 1 Dynamics in Primary Mammalian Cells," Science 299(5607):719-721.

Fu, D. et al. (Jul. 2014). "Imaging the Intracellular Distribution of Tyrosine Kinase Inhibitors in Living Cells With Quantitative Hyperspectral Stimulated Raman Scattering," Nature Chemistry 6(7):614-622, 18 pages.

Fukaya, T. et al. (Jul. 14, 2016). "Enhancer Control of Transcriptional Bursting," Cell 166(2):358-368.

Galdeano, C. (Oct. 23, 2014). "Structure-Guided Design and Optimization of Small Molecules Targeting the Protein-Protein Interaction Between the Von Hippel-Lindau (VHL) E3 Ubiquitin Ligase and the Hypoxia Inducible Factor (HIF) Alpha Subunit With In Vitro Nanomolar Affinities," J. Med. Chem. 57(20):8657-8663.

Germain, P. et al. (Dec. 2006). "Overview of Nomenclature of Nuclear Receptors," Pharmacological Reviews 58(4):685-704.

Ghosh, R.P. et al. (May 25, 2010). "Unique Physical Properties and Interactions of the Domains of Methylated DNA Binding Protein 2 (MeCP2)," Biochemistry 49(20):4395-4410.

Grewal, S.I.S. et al. (2007). "Heterochromatin Revisited," Nature Reviews Genetics 8(1):35-46.

Gu, B. et al. (Mar. 2, 2018, e-pub. Jan. 25, 2018). "Transcription-Coupled Changes in Nuclear Mobility of Mammalian Cis-Regulatory Elements," Science 359(6379):1050-1055.

Guo, W. et al. (Mar. 9, 2018). "Splicing Factor RBM20 Regulates Transcriptional Network of Titin Associated and Calcium Handling Genes in the Heart," Int J Biol Sci. 14(4): 369-380.

Guo, Y.E. et al. (Mar. 9, 2018, e-pub. Aug. 7, 2019). "Pol II Phosphorylation Regulates a Switch Between Transcriptional and Splicing Condensates," Nature 572(7770):543-548, 41 pages.

Guy, J. et al. (2011, e-pub. Jun. 29, 2011). "The Role of MeCP2 in the Brain," Annual Review of Cell and Developmental Biology 27(1):631-652.

Hager, K. et al. (Jan. 1, 2007). "Alpha-Lipoic Acid as a New Treatment Option For Alzheimer's Disease—A 48 Months Follow-Up Analysis," Journal of Neural Transmission Suppl 72:189-193.

Hahn, S. et al. (Nov. 2011). "Transcriptional Regulation in *Saccharomyces cerevisiae*: Transcription Factor Regulation and Function, Mechanisms of Initiation, and Roles of Activators and Coactivators," Genetics 189 (3):705-736.

Han, T.W. et al. (May 11, 2012). "Cell-Free Formation of RNA Granules: Bound RNAs Identify Features and Components of Cellular Assemblies," Cell 149(4):768-779.

Harmon, T.S. et al. (Nov. 1, 2017). "Intrinsically Disordered Linkers Determine the Interplay Between Phase Separation and Gelation in Multivalent Proteins." Elife 6:e30294, 31 pages.

Hendrich, B. et al. (Nov. 1998). "Identification and Characterization of a Family of Mammalian Methyl-CpG Binding Proteins," Molecular and Cellular Biology 18(11):6538-6547.

Hinisz, D. et al. (Mar. 23, 2017). "A Phase Separation Model for Transcriptional Control," Cell 169(1):13-23.

Hinisz, D. et al. (Nov. 7, 2013, e-pub. Oct. 10, 2013). "Super-enhancers in the control of cell identity and disease," Cell 155(4):934-947.

Hu, L.D. et al. (Aug. 2017, e-pub Jul. 10, 2017) "Screening Novel Stress Granule Regulators From a Natural Compound Library," Protein & Cell 8(8):618-622.

Hyman, A.A. et al. (2014) "Liquid-Liquid Phase Separation in Biology," Annual Review of Cell and Developmental Biology 30:39-58.

Imbeault, M. et al. (2017). "KRAB Zinc-Finger Proteins Contribute to the Evolution of Gene Regulatory Networks," Nature 543(7646):550-554.

International Search Report and Written Opinion of the International Searching Authority mailed Jan. 27, 2020, for International Patent Application No. PCT/EP2019/077818, filed Oct. 14, 2019, 12 pages.

International Search Report and Written Opinion of the International Searching Authority mailed Sep. 23, 2019, for International Patent Application No. PCT/US2019/023694, filed Mar. 22, 2019, 16 pages.

Ip, J.P.K. et al. (Jun. 2018, e-pub. Mar. 6, 2019). "Rett Syndrome: Insights Into Genetic, Molecular and Circuit Mechanisms," Nature Reviews Neuroscience 19(6):368-382.

Janicki, S.M. et al. (Mar. 5, 2004). "From Silencing to Gene Expression: Real-Time Analysis in Single Cells," Cell 116(5):683-698.

Kang, Y. K. et al. (2002). "The TRAP/Mediator Coactivator Complex Interacts Directly With Estrogen Receptors Alpha and Beta

(56) References Cited

OTHER PUBLICATIONS

Through the TRAP220 Subunit and Directly Enhances Estrogen Receptor Function In Vitro," Proc Natl Acad Sci U.S.A. 99(5):2642-2647.
Kato, M. et al. (May 11, 2012). "Cell-Free Formation of RNA Granules: Low Complexity Sequence Domains Form Dynamic Fibers Within Hydrogels." Cell 149(4):753-767.
Kwon, I. et al. (Nov. 21, 2013). "Phosphorylation-Regulated Binding of RNA Polymerase II to Fibrous Polymers of Low-Complexity Domains," Cell 155(5):1049-1060.
Lachner, M. et al. (2001). "Methylation of Histone H3 Lysine 9 Creates a Binding Site For HP1 Proteins," Nature 410(6824):116-120.
Lambert, S.A. et al. (Feb. 8, 2018). "The Human Transcription Factors," Cell 172(4):650-665.
Larson, A.G. et al. (Jul. 13, 2017). "Liquid Droplet Formation By HP1α Suggests a Role for Phase Separation in Heterochromatin," Nature 547(7662):236-240.
Lei, J.T. et al. (Aug. 7, 2018). "Functional Annotation of ESR1 Gene Fusions in Estrogen Receptor-Positive Breast Cancer," Cell Rep 24(6):1434-1444.
Leroi, I. et al. (Oct. 25, 2006, e-pub. Jun. 27, 2006). "Non-Dopaminergic Treatment of Cognitive Impairment and Dementia in Parkinson's Disease: A Review," Journal of Neurological Sciences 248(1-2):104-114.
Lewis, J.D. et al. (1992). "Purification, Sequence, and Cellular Localization of a Novel Chromosomal Protein That Binds to Methylated DNA," Cell 69(6):905-914.
Li, P. et al. (Mar. 15, 2012). "Phase Transitions in the Assembly of Multivalent Signalling Proteins." Nature 483 (7389):336-340, 13 pages.
Li, S. et al. (2013, e-pub Jan. 9, 2013). "Rbm20 Regulates Titin Alternative Splicing as a Splicing Repressor," Nucleic Acids Research 41(4):2659-2672.
Li, X-H. et al. (May 1, 2018, e-pub. Feb. 12, 2018). "Function and Regulation of Phase-Separated Biological Condensates," Biochemistry 57(17):2452-2461.
In, Y. et al. (Oct. 15, 2015). "Formation and Maturation of Phase-Separated Liquid Droplets by RNA-Binding Proteins," Mol. Cell 60(2):208-219.
Lin, Y. et al. (Oct. 20, 2016). "Toxic PR Poly-Dipeptides Encoded By The C9orf72 Repeat Expansion Target LC Domain Polymers," Cell 167(3):789-802.
Liss, M. et al. (Jun. 11, 2018). "Drug Discovery With an RBM20 Dependent Titin Splice Reporter Identifies Cardenolides as Lead Structures to Improve Cardiac Filling," PloS One 13(6): e0198492, 1-19.
Lyst, M.J. et al. (2015). "Rett Syndrome: A Complex Disorder With Simple Roots. Nature Reviews Genetics," 16(5):261-274.
Macarron, R. et al. (2009, e-pub Jun. 5. 2009). "Design and Implementation of High-Throughput Screening Assays," in High Throughput Screening, Janzen W., Bernasconi P. (eds) Humana Press: Totowa, NJ, vol. 565, 1-32., 12 pages (Abstract only).
Mackenzie, I.R. et al. (Aug. 16, 2017): "TIAI Mutations in Amyotrophic Lateral Sclerosis and Frontotemporal Dementia Promote Phase Separation and Alter Stress Granule Dynamics," Neuron 95(4):808-816.
Maharana, S. et al. (May 25, 2018, e-pub. Apr. 12, 2018). "RNA Buffers the Phase Separation Behavior of Prion-Like RNA-Binding Proteins," Science 360(6391):918-921.
Mangelsdorf, I. et al. (Jan. 1, 2017, e-pub Jun. 12, 2017). "Healing of Amyotrophic Lateral Sclerosis: A Case Report," Complementary Medicine Research 24(3):175-181.
Mansour, M.R. et al. (Dec. 12, 2014, e-pub Jan. 20, 2016). "An Oncogenic Super-Enhancer Formed Through Somatic Mutation of a Noncoding Intergenic Element," Science 346(6215):1373-1377.
Meehan, R.R. et al. (1992). "Characterization of Mecp2, a Vertebrate DNA-Binding Protein With Affinity for Methylated DNA," Nucleic Acids Research 20(19):5085-5092.

Mitchell, P.J. et al. (1989). "Transcriptional Regulation in Mammalian Cells by Sequence-Specific DNA Binding Proteins," Science 245(4916):371-378.
Nagalingam A. et al. (Apr. 2012, e-pub Feb. 16, 2012). "Med1 Plays a Critical Role in the Development of Tamoxifen Resistance," Carcinogenesis 33(4):918-930.
Nakano, M. et al. (Apr. 15, 2008). "Inactivation of a Human Kinetochore by Specific Targeting of Chromatin Modifiers," Developmental Cell, 14(4):507-522.
Nan, X. et al. (1993). "Dissection of the Methyl-Cpg Binding Domain From the Chromosomal Protein Mecp2," Nucleic Acids Research 21(21):4886-4892.
Naumann, M. et al. (Jan. 23, 2018). "Impaired DNA Damage Response Signaling By FUS-NLS Mutations Leads to Neurodegeneration and FUS Aggregate Formation," Nature Communications 9(1):1-17.
Nesbit C.E. et al. (May 13, 1999). "MYC Oncogenes and Human Neoplastic Disease," Oncogene 18(19):3004-3016.
Nott, T.J. et al. (Mar. 5, 2015). "Phase Transition of a Disordered Nuage Protein Generates Environmentally Responsive Membraneless Organelles," Mol. Cell 57(5):936-947.
Oates, M.E. et al. (2013, e-pub. Nov. 29, 2012). "$D^2P^2$: Database of Disordered Protein Predictions," Nucleic Acids Res. 41(D1):D508-D516.
Osborne, C.K. et al. (Feb. 11, 2011). "Mechanisms of Endocrine Resistance in Breast Cancer," Annu Rev Med 62:233-247, 17 pages.
Ozers, M.S. et al. (Jan. 1, 2005). "Analysis of Ligand-Dependent Recruitment of Coactivator Peptides to Estrogen Receptor Using Fluorescence Polarization," Mol Endocrinol 19(1):25-34.
Patel, A. et al. (Aug. 27, 2015). "A Liquid-to-Solid Phase Transition of the ALS Protein Accelerated by Disease Mutation" Cell 162:1066-1077.
Patel, A. et al. (May 19, 2017). "ATP As A Biological Hydrotrope," Science 356(6339):753-756.
Patel, B.P. et al. (Dec. 1, 2009). "Nutritional and Exercise-Based Interventions in the Treatment of Amyotrophic Lateral Sclerosis," Clinical Nutrition 28(6):604-617.
Posey, A.E. et al. (Mar. 9, 2018, e-pub. Jan. 22, 2018). "Profilin Reduces Aggregation and Phase Separation of Huntingtin N-Terminal Fragments by Preferentially Binding to Soluble Monomers and Oligomers," Journal of Biological Chemistry 293(10):3734-3746.
Potenza, E. et al. (Oct. 31, 2014). "MobiDB 2.0: An Improved Database of Intrinsically Disordered and Mobile Proteins," Nucleic Acids Res. 43(D1):D315-D320.
Rahman S. et al. (Jun. 15, 2017). "Activation of the LMO2 Oncogene Through a Somatically Acquired Neomorphic Promoter in T-Cell Acute Lymphoblastic Leukemia," Blood 129(24):3221-3226.
Robb, C.M. et al. (Jul. 4, 2017). "Chemically Induced Degradation of CDK9 by a Proteolysis Targeting Chimera (PROTAC)," Chem Commun (Camb). 53(54):7577-7580, 12 pages.
Roberts, S.G.E. (Aug. 2000). "Mechanisms of Action of Transcription Activation and Repression Domains," Cell. Mol. Life Sci. 57(8-9):1149-1160.
Roe J. S. et al. (Aug. 24, 2017). "Enhancer Reprogramming Promotes Pancreatic Cancer Metastasis," Cell 170(5):875-888, e820.
Sabari, B.R. et al. (Jul. 27, 2018, e-pub Jun. 21, 2018). "Coactivator Condensation at Super-Enhancers Links Phase Separation and Gene Control," Science, 361(6400): eaar3958, 1-24.
Saha, S. et al. (Sep. 8, 2016, e-pub. Sep. 1, 2016). "Polar Positioning of Phase-Separated Liquid Compartments in Cells Regulated by an Mma Competition Mechanism," 166(6):1572-1584.
Sakamoto, K.M. et al. (Jul. 17, 2001). "Protacs: Chimeric Molecules That Target Proteins to the Skp1-Cullin-F Box Complex for Ubiquitination and Degradation," Proceedings of the National Academy of Sciences 98(15):8554-8559.
Sever, R. et al. (Mar. 1, 2013). "Signaling by Nuclear Receptors," Cold Harbor Perspectives in Biology 5(3):1-4.
Shang, Y. et al. (Dec. 8, 2000). "Cofactor Dynamics and Sufficiency in Estrogen Receptor-Regulated Transcription," Cell 103(6):843-852.

(56) References Cited

OTHER PUBLICATIONS

Shin, Y. et al. (Sep. 22, 2017). "Liquid Phase Condensation in Cell Physiology and Disease," Science 357(6357):eaaf4382, 13 pages.
Shrinivas, K. et al. (Dec. 17, 2018). "Enhancer Features That Drive Formation of Transcriptional Condensates," Molecular Cell 75(3):549-561, 28 pages.
Sigler, P.B. (May 19, 1988). "Acid Blobs and Negative Noodles," Nature 333(6170):210-212.
Skene, P.J. et al. (Feb. 26, 2010). "Neuronal MeCP2 Is Expressed at Near Histone-Octamer Levels and Globally Alters the Chromatin State," Molecular Cell 37(4):457-468.
Soufi, A. et al. (Nov. 21, 2012). "Facilitators and Impediments of the Pluripotency Reprogramming Factors' Initial Engagement With the Genome," Cell 151(5):994-1004.
Staby, L. et al. (Aug. 2017). "Eukaryotic Transcription Factors: Paradigms of Protein Intrinsic Disorder," Biochem. J. 474(15):2509-2532.
Strom, A.R. et al. (Jul. 13, 2017). "Phase Separation Drives Heterochromatin Domain Formation," Nature 547 (7662):241-245, 19 pages.
Tate, P. et al. (Feb. 1996). "The Methyl-Cpg Binding Protein Mecp2 Is Essential for Embryonic Development in the Mouse," Nat Genet 12(2):205-208.
Triezenberg, S.J. (Apr. 1995). "Structure and Function of Transcriptional Activation Domains," Curr. Opin. Genet. Dev. 5(2):190-196.
Tsai, A. et al. (Nov. 2, 2017). "Nuclear Microenvironments Modulate Transcription From Low-Affinity Enhancers," Elife 6:e28975, 18 pages.
Tuttle, L.M. et al. (Mar. 20, 2018). "Gcn4-Mediator Specificity Is Mediated by a Large and Dynamic Fuzzy Protein-Protein Complex," Cell Rep. 22(12):3251-3264.
Van Esch, H. et al. (Sep. 2005). "Duplication of the MECP2 Region Is a Frequent Cause of Severe Mental Retardation and Progressive Neurological Symptoms in Males," The American Journal of Human Genetics 77(3):442-453.
Wakefield, R.I.D. et al. (Sep. 3, 1999). "The Solution Structure of the Domain From Mecp2 That Binds to Methylated DNA," Journal of Molecular Biology 291(5):1055-1065.
Waks A.G. et al. (Jan. 22, 2019). "Breast Cancer Treatment: A Review," JAMA 321(3):288-300.
Wang Y. et al. (Sep. 24, 2015). "CDK7-Dependent Transcriptional Addiction in Triple-Negative Breast Cancer," Cell 163(1):174-186.
Wang, J. et al. (May 2016). "New Insights into the Regulation of Heterochromatin," Trends in Genetics 32(5):284-294, 19 pages.
Wang, T. et al. (2018, e-pub. May 26, 2018). "α-Lipoic Acid Attenuates Oxidative Stress and Neurotoxicity Via the ERK/Akt-Dependent Pathway in the Mutant hSOD1 Related *Drosophila* Model and the NSC34 Cell Line of Amyotrophic Lateral Sclerosis," Brain Research Bulletin 140(26):299-310.
Wegmann, S. et al. (Apr. 3, 2018, e-pub. Feb. 22, 2018). "Tau Protein Liquid—Liquid Phase Separation Can Initiate Tau Aggregation," The EMBO Journal 37(7):e98049, 21 pages.
Wheeler R.J. et al. (Dec. 15, 2017). "M128: Small Molecules for Modulating Protein Driven Liquid-Liquid Phase Separation in Neurodegenerative Disease," Molecular Biology of the Cell; Annual Joint Meeting of American Society for Cell Biology/European Molecular Biology Organization (ASCB/EMBO), American Society for Cell Biology: Philadelphia, PA, 28(26):M128, 2 pages (Abstract only).
Wheeler, R.J. et al. (Aug. 21, 2019) "Small Molecules for Modulating Protein Driven Liquid-Liquid Phase Separation in Treating Neurodegenerative Disease," BioRxiv 721001, 48 pages.
Wheeler, R.J. et al. (May 26, 2018). "Controlling Compartmentalization by Non-Membrane-Bound Organelles," Philosophical Transactions of the Royal Society B: Biological Sciences 373(1747):20170193, 9 pages.
Winter, G.E. et al. (Jun. 19, 2015). "Selective Target Protein Degradation via Phthalimide Conjugation," Science 348(6241):1376-1381, 13 pages.

Zamudio, A.V. et al. (Dec. 5, 2015). "Mediator Condensates Localize Signaling Factors to Key Cell Identity Gene," Mol Cell 76(5):P753-766.E6.
Aguzzi, A. et al. (Jul. 2016). "Phase Separation: Linking Cellular Compartmentalization to Disease," Trends in Cell Biology 26(7):547-558.
Andreassen, O.A. (Apr. 2001). "Effects of on Inhibitor of Poly(ADP-Ribose) Polymerase, Desmethylselegiline, Trientine, and Lipoic Acid in Transgenic ALS Mice," Exp Neurol. 168(2):419-424.
Bailey, J.K. et al. (2017, e-pub. Aug. 9, 2017). "Nucleic Acid Binding Proteins Affect the Subcellular Distribution of Phosphorothioate Antisense Oligonucleotides." Nucleic Acids Research 45(18):10649-10671.
Basturea, G.N. et al. (Jul. 1, 2019). "Biological Condensates," Material Methods 9, 17 pages.
Bracha, D. et al. (Nov. 29, 2018). "Mapping Local and Global Liquid Phase Behavior in Living Cells Using Photo-Oligomerizable Seeds," Cell 175(6):1467-1480.
Cai, D. et al. (Feb. 10, 2021). "Biomolecular Condensates and Their Links to Cancer Progression", Trends in Biochemical Sciences 46(7):535-549.
Caicedo, J. C. et al. (Sep. 2019, e-pub. Jul. 16, 2019). "Evaluation of Deep Learning Strategies for Nucleus Segmentation in Fluorescence Images," Cytometry, Part A: the journal of the International Society for Analytical Cytology 95(9):952-965.
Carpenter, A.E. et al. (Oct. 31, 2006). "Cellprofiler: Image Analysis Software for Identifying and Quantifying Cell Phenotypes," Genome Biology 7(10):R100, 11 pages.
Chen Y. et al. (Apr. 2019). "Genome Organization Around Nuclear Speckles," Current Opinion in Genetics & Development 55:91-99.
Cheng, X. et al. (Jul. 1996). "Direct Measurement of Oligonucleotide Binding Stoichiometry of Gee V Protein by Mass Spectrometry," Proc. Natl. Acad. Sci. USA 93:7022-7027.
Cooper, M.S. et al. (Feb. 1, 2010, e-pub Sep. 5, 2009). "Visualizing Green Oil in Live Algal Cells", Journal of Bioscience and Bioengineering 109(2):198-201.
Cuccarese, M.F. et al. (2020). "Functional Immune Mapping With Deep-Learning Enabled Phenomics Applied to Immunomodulatory and COVID-19 Drug Discovery," bioRxiv, 24 pages.
Davies, N. M. et al. (2018, e-pub. Jul. 12, 2018). "Reading Mendelian Randomisation Studies: A Guide, Glossary, and Checklist For Clinicians," BMJ 362(k601):1-11.
Dolgin, E. (Feb. 9, 2021). "Drug Startups Coalesce Around Condensates", Nature Biotechnology 39(2):123-125.
Finucane, H.K. et al. (Apr. 2018). "Heritability Enrichment of Specifically Expressed Genes Identifies Disease-Relevant Tissues and Cell Types," Nat Genet. 50(4):621-629.
Gibson, B.A. et al. (Oct. 3, 2019). "Organization of Chromatin by Intrinsic and Regulated Phase Separation," Cell 179(2):470-484.
Gill, S.J. et al. (Jun. 25, 1980). "Ligand-Linked Phase Equilibria of Sickle Cell Hemoglobin," J Mol Biol. 140(2):299-312, 2pages. (Abstract Only).
Guo, W. et al. (Feb. 10, 2018). "RBM20, A Potential Target for Treatment of Cardiomyopathy Via Titin Isoform Switching," Biophysical Reviews 10(1):15-25.
Guo, W. et al. (May 2012). "RBM20, A Gene For Hereditary Cardiomyopathy, Regulates Titin Splicing," Nat Med. 18(5):766-773.
Handoko, L. et al. (Apr. 3, 2018, e-pub. Aug. 6, 2018). "JQ1 Affects BRD2-Dependent and Independent Transcription Regulation Without Disrupting H4-Hyperacetylated Chromatin States," Epigenetics 13(4):410-431.
Huang, H. (Jul. 13, 2017). "Fine-Mapping Inflammatory Bowel Disease Loci to Single-Variant Resolution," Nature 547(7662):173-178.
International Preliminary Report on Patentability issue date of Apr. 14, 2021 for Patent Application No. PCT/EP2019/077818, filed Oct. 14, 2019, 8 pages.
International Preliminary Report on Patentability issue date of Aug. 10, 2021 for Patent Application No. PCT/US2020/017333, filed Feb. 7, 2020, 7 pages.

(56) References Cited

OTHER PUBLICATIONS

International Preliminary Report on Patentability issue date of Aug. 25, 2021 for Patent Application No. PCT/US2020/015329, filed Jan. 28, 2020, 6 pages.
International Preliminary Report on Patentability issue date of Mar. 15, 2022 for Patent Application No. PCT/US2020/051331, filed Sep. 17, 2020, 11 pages.
International Preliminary Report on Patentability, issued on Nov. 16, 2021, for PCT Application No. PCT/US2020/033295, filed on May 15, 2020, 13 pages.
International Preliminary Report on Patentability, issued on Sep. 29, 2020, for PCT Application No. PCT/US2019/023694, filed on Mar. 22, 2019, 11 pages.
International Search Report and Written Opinion of the International Searching Authority mailed Apr. 2, 2020, for International Application No. PCT/US2020/015329, filed Jan. 28, 2020, 9 pages.
International Search Report and Written Opinion of the International Searching Authority mailed Jul. 3, 2020, for International Application No. PCT/US2020/017333, filed Feb. 7, 2020, 10 pages.
International Search Report and Written Opinion of the International Searching Authority mailed Jul. 25, 2022, for International Application No. PCT/US2022/018311, filed Mar. 1, 2022, 23 pages.
International Search Report and Written Opinion of the International Searching Authority mailed Jul. 29, 2020, for International Application No. PCT/US2020/033295, filed May 15, 2020, 17 pages.
International Search Report and Written Opinion of the International Searching Authority mailed Mar. 28, 2022, for International Application No. PCT/US2021/045592, filed Aug. 11, 2021, 48 pages.
International Search Report and Written Opinion of the International Searching Authority mailed May 17, 2022, for International Application No. PCT/US2022/018282, filed Mar. 1, 2022, 18 pages.
International Search Report and Written Opinion of the International Searching Authority mailed Nov. 26, 2020, for International Application No. PCT/US2020/051331, filed Sep. 17, 2020, 16 pages.
Jain, A. et al. (Jun. 8, 2017). "RNA Phase Transitions in Repeat Expansion Disorders," Nature 546(7657):243-247.
Klein, I.A. et al. (Jun. 19, 2020). "Partitioning of Cancer Therapeutics in Nuclear Condensates," Science 368(6497):1386-1392.
Kornberg, R.D. (May 2005). "Mediator and the Mechanism of Transcriptional Activation," Trends in Biochemical Sciences 30(5):235-239.
Kraus, O. Z., et al. (2016). "Classifying and Segmenting Microscopy Images With Deep Multiple Instance Learning," Bioinformatics 32(12):i52-i59.
Lanni, E.J. et al. (Aug. 1, 2012, e-pub Aug. 30, 2013). "Mass Spectrometry Imaging and Profiling of Single Cells," Journal of Proteomics 75(16):5036-5051.
Lau, M. S. et al. (Mar. 10, 2017). "Mutation of a Nucleosome Compaction Region Disrupts Polycomb-Mediated Axial Patterning," Science 355(6329):1081-1084.
Lee, J-E. et al. (Dec. 20, 2017). "Brd4 Binds to Active Enhancers to Control Cell Identity Gene Induction in Adipogenesis and Myogenesis", Nature Communications 8(1):2217, 1-12.
Lee, T.H. et al. (2017, e-pub. Jul. 17, 2017). "Molecular Mechanism of PD-1/PD-L1 Blockade via Anti-PD-L1 Antibodies Atezolizumb and Durvalumab," Scientific Reports 7(1):1-12.
Li, C.H. et al. (Oct. 2020, e-pub. Jul. 22, 2020). "Mecp2 Links Heterochromatin Condensates and Neurodevelopmental Disease," Nature 586(7829):440-444.
Lowe, D. (Aug. 6, 2019). "A Condensate-Modifying Compound, Put to the Test Science AAAS", Biological News (science.erg), 4 pages, as retrieved from https://www.science.org/content/blog-pest/condensate-modifying-compound-put-test.
Mahajan, A. et al. (Nov. 2018, e-pub. Dec. 10, 2018), "Fine-Mapping Type 2 Diabetes Loci to Single-Variant Resolution Using High-Density Imputation and Islet-Specific Epigenome Maps," Nature Genetics 50(11):1505-1513.
Malik, S. et al. (Oct. 13, 2010). "The Metazoan Mediator Co-Activator Complex as an Integrative Hub For Transcriptional Regulation," Nature Reviews Genetics 11(11) 761-772.
Martin, E.W. et al. (February, 7, 2020). "Valence and Patterning of Aromatic Residues Determine the Phase Behavior of Prion-Like Domains," Science 367(6478):694-699.
Mateju, D.E. et al. (Jun. 14, 2017, e-pub. Apr. 4, 2017). "An Aberrant Phase Transition of Stress Granules Triggered by Misfolded Protein and Prevented by Chaperone Function", The EMBO Journal 36(12):1669-1687.
McQuin, C. et al. (Jul. 3, 2018). "Cellprofiler 3.0: Next-Generation Image Processing for Biology," Plos Biology 16(7):e2005970, 17 pages.
Mitrea, D.M. et al. (Feb. 26, 2018). "Self-Interaction of NPM1 Modulates Multiple Mechanisms of Liquid-Liquid Phase Separation," Nature Communications 9(1):1-13.
Muiznieks, L.D. et al.(Nov. 2, 2018). "Role of Liquid-Liquid Phase Separation in Assembly of Elastin and Other Extracellular Matrix Proteins," Journal of Molecular Biology 430(23):4741-4753.
Mullard, A. et al. (May 1, 2019). "Biomolecular Condensates Pique Drug Discovery Curiosity", Nature Reviews 18:324-326.
Murayama, R. et al. (2018, e-pub Jun. 12, 2018). "Phosphorylation of the RSRSP Stretch is Critical for Splicing Regulation by RNA-Binding Motif Protein 20 (RBM20) Through Nuclear Localization," Scientific Reports 8(1):1-14.
Nabet, B, et al. (May 2018, e-pub Dec. 17, 2018). "The Dtag System for Immediate and Target-Specific Protein Degradation," Nature Chemical Biology 14(5):431-441.
Pers, T. H. et al. (Jan. 19, 2015). "Biological Interpretation of Genome-Wide Association Studies Using Predicted Gene Functions," Nature Communications 6(1):1-9.
Pessina, F. et al. (Oct. 2019). "Functional Transcription Promoters at DNA Double-Strand Breaks Mediate RNA-Driven Phase Separation of Damage-Response Factors," Nature Cell Biology 21(10):1286-1299.
Plys, A.J. et al. (Jul. 1, 2019). "Phase Separation of Polycomb-Repressive Complex 1 Is Governed by a Charged Disordered Region of CBX2." Genes & Development 33(13-14):799-813.
Qi, G. et al. (2019). "Mendelian Randomization Analysis Using Mixture Models for Robust and Efficient Estimation of Causal Effects," Nature Communications 10(1):1-10.
Riback, J.A. et al. (2020, e-pub May 6, 2020), "Composition-Dependent Thermodynamics of Intracellular Phase Separation," Nature 581(7807):209-214.
Riback, J.A. et al. (Oct. 22, 2019). "Composition Dependent Phase Separation Underlies Directional Flux Through the Nucleolus," bioRxiv 809210:26 pages.
Rossin, E. J. et al. (Jan. 13, 2011). "Proteins encoded in genomic regions associated with immune-mediated disease physically interact and suggest underlying biology," PLoS genetics 7(1):e1001273, 13 pages.
Ruff, K.M. et al. (Mar. 9, 2021). "Ligand Effects on Phase Separation of Multivalent Macromolecules," Proc Natl Acad Sci U S A. 118(10):e2017184118, 10 pages.
Schneider, J.W. et al. (Nov. 2020, e-pub. Nov. 13, 2020). "Dysregulated Ribonucleoprotein Granules Promote Cardiomyopathy in RBM20 Gene-Edited Pigs," Nature Medicine 26(11):1788-1800, 2 pages. (Abstract Only).
Smith, R. et al. (2016). "Raman Spectroscopy: An Evolving Technique for Live Cell Studies," Analyst 141(12):3590-3600.
Tisel, W.A. et al. (Oct. 10, 1980). "Polyphasic Linkage Between Protein Solubility and Ligand Binding in the Hemoglobin-Polyethylene Glycol System," J Biol Chem 255(19):8975-8978.
Tulpule, A. et al. (Apr. 9, 2020). "Kinase-Mediated RAS Signaling Via Membraneless Cytoplasmic Protein Granules," Biorxiv 704312:48 pages.
U.S. Appl. No. 17/611,560, filed May 15, 2020, for Young et al. (U.S. Patent Application is not submitted herewith pursuant to the waiver of 37 C.F.R. § 1.98(a)(2)(iii) issued by the Office on Sep. 21, 2004.).

(56) References Cited

OTHER PUBLICATIONS

U.S. Appl. No. 17/721,054, filed Apr. 14, 2022, for Szewczak et al. (U.S. Patent Application is not submitted herewith pursuant to the waiver of 37 C.F.R. § 1.98(a)(2)(iii) issued by the Office on Sep. 21, 2004.).
U.S. Appl. No. 17/761,545, filed Mar. 17, 2022, for Patel et al. (U.S. Patent Application is not submitted herewith pursuant to the waiver of 37 C.F.R. § 1.98(a)(2)(iii) issued by the Office on Sep. 21, 2004.).
U.S. Appl. No. 17/960,702, filed Oct. 5, 2022, for Beutel et al. (U.S. Patent Application is not) submitted herewith pursuant to the waiver of 37 C.F.R. § 1.98(a)(2)(iii) issued by the Office on Sep. 21, 2004.).
Vuignier, K. et al. (Sep. 2010). "Drug-Protein Binding: A Critical Review of Analytical Tools," Anal Bioanal Chem. 398(1):53-66.
Vujkovic, M. et al. (Jul. 2020, e-pub. Jun. 15, 2020). "Discovery of 318 New Risk Loci For Type 2 Diabetes and Related Vascular Outcomes Among 1.4 Million Participants in a Multi-Ancestry Meta-Analysis," Nature Genetics 52(7):680-691.
Wan, L. et al. (Jan. 2020, e-pub. Mar. 9, 2020). "Impaired Cell Fate Through Gain-Of-Function Mutations in a Chromatin Reader," Nature 577(7788):121-126.
Watanabe, K. et al. (Nov. 28, 2017). "Functional Mapping and Annotation of Genetic Associations With FUMA," Nat Commun. 8(1):1826, 1-11.
Weeks, E. M. et al. (2020). "Leveraging Polygenic Enrichments of Gene Features to Predict Genes Underlying Complex Traits and Diseases," MedRxiv, 24 pages.
White, M. R. et al. (May 16, 2019). "C9orf72 Poly (PR) Dipeptide Repeats Disturb Biomolecular Phase Separation and Disrupt Nucleolar Function," Molecular Cell 74(4):713-728.
Yu, C. et al. (May 2021, e-pub. Sep. 2, 2020). "Proteome-Scale Analysis of Phase-Separated Proteins in Immunofluorescence Images," Briefings in Bioinformatics 22(3):bbaa187, 15 pages.
Zhang, P. et al. (Jun. 18, 2018). "Optogranules Reveal the Evolution of Stress Granules to ALS-FTD Pathology," bioRxiv 348870, 35 pages, as retrieved from https://www.biorxiv.org/content/biorxiv/early/2018/06/18/348870.full.pdf.
Zhou, M. et al. (Mar. 19, 2020). "Phase-Separated Condensate-Aided Enrichment of Biomolecular Interactions for High-Throughput Drug Screening in Test Tubes", Journal of Biological Chemistry 295(33):11420-11434.
Zhu, C. et al. (Feb. 1, 2015, e-pub Jan. 8, 2015), "RBM20 Is an Essential Factor for Thyroid Hormone-Regulated Titin Isoform Transition," Journal of Molecular Cell Biology 7(1):88-90.
Alberti, S. et al. (Oct. 2016). "Are Aberrant Phase Transitions a Driver of Cellular Aging?" Bioessays 38(10):959-968.
Beqqali, A. et al. (Oct. 2016, e-pub. Aug. 5, 2016). "A Mutation in the Glutamate-Rich Region of RNA-Binding Motif Protein 20 Causes Dilated Cardiomyopathy Through Missplicing of Titin and Impaired Frank-Starling Mechanism," Cardiovasc Res. 112(1):452-463.
Capel, P.J. et al. (Feb. 1994). "Heterogeneity of Human IgG Fc Receptors," Immunomethods 4(1):25-34.
Chothia, C. et al. (Aug. 20, 1987). "Canonical Structures for the Hypervariable Regions of Immunoglobulins," J. Mol. Biol. 196(4):901-917.
Daeron, M. (1997). "Fc Receptor Biology," Annu. Rev. Immunol. 15:203-234.
De Haas, M. et al. (Oct. 1995). "Fcγ Receptors of Phagocytes," J. Lab. Clin. Med. 126(4):330-341.
Guyer, R.L. et al. (Aug. 1976). "Immunoglobulin Binding by Mouse Intestinal Epithelial Cell Receptors," J. Immunol. 117(2):587-593.
International Preliminary Report on Patentability, issued on Aug. 29, 2023, for PCT Application No. PCT/US2022/018282, filed on Mar. 1, 2023, 9 pages,.
International Preliminary Report on Patentability, issued on Aug. 29, 2023, for PCT Application No. PCT/US2022/018311, filed on Mar. 1, 2023, 14 pages.
International Preliminary Report on Patentability, issued on Feb. 7, 2023, for PCT Application No. PCT/US2021/045592, filed on Aug. 11, 2021, 16 pages.
International Search Report and Written Opinion of the International Searching Authority mailed Dec. 22, 2022, for International Application No. PCT/US2022/040890, filed Aug. 19, 2022, 9 pages.
Isabelle, M. et al. (Oct. 1, 2012). "Quantitative Proteomics and Dynamic Imaging Reveal that G3BP-mediated Stress Granule Assembly is Poly(ADP-ribose)-Dependent Following Exposure to MNNG-induced DNA Alkylation," Journal of Cell Science 125(19):4555-4566.
Kabat, E.A. et al. (Oct. 10, 1977). "Unusual Distributions of Amino Acids in Complementarity-Determining (Hypervariable) Segments of Heavy and Light Chains of Immunoglobulins and Their Possible Roles in Specificity of Antibody-Combining Sites," J. Biol. Chem. 252(19):6609-6616.
Kim, J-K. et al. (1994). "Localization of the Site of the Murine IgGl Molecule That is Involved in Binding to the Murine Intestinal Fc Receptor," Eur. J. Immunol. 24:2429-2434.
Lee, H-W. et al. (October 20103, e-pub Sep. 26, 2013). "Real-Time Single-Molecule Coimmunoprecipitation of Weak Protein-Protein Interactions," Nature Protocols 8(10):2045-2060.
MacCallum, R.M. et al. (1996). "Antibody-Antigen Interactions: Contact Analysis and Binding Site Topography," J. Mol. Biol. 262:732-745.
Mohammed, H. et al. (Feb. 2016, e-pub. Jan. 21, 2016). "Rapid Immunoprecipitation Mass Spectrometry of Endogenous Proteins (RIME) For Analysis of Chromatin Complexes," Nature Protocols 11(2):316-326.
Ravetch, J.V. et al. (1991). "Fc Receptors," Annu. Rev. Immunol. 9:457-492.
Rigaut, G. et al. (Oct. 1999). "A Generic Protein Purification Method for Protein Complex Characterization and Proteome Exploration," Nature Biotechnology 17(10):1030-1032.
Sciuto, M. R. et al. (Jan. 2019, e-pub. Oct. 30, 2018). "Two-Step Co-Immunoprecipitation (TIP)," Current Protocols in Molecular Biology 125(1):e80, 21 pages.
Sciuto, M. R. et al. (May 2018). "Two-Step Coimmunoprecipitation (TIP) Enables Efficient and Highly Selective Isolation of Native Protein Complexes," Molecular & Cellular Proteomics 17(5):993-1009.
Sohei, M. (Sep. 26, 2019). "ALS and RNA Binding Proteins as Therapeutic Target," located at https://gousei.f.u-tokyo.ac.jp/seminar/pdf/Lit_Sohel_Majima_M2.pdf, 33 pages.
Woodruff, J. B. et al. (Jun. 1, 2017). "The Centrosome Is a Selective Condensate that Nucleates Microtubules by Concentrating Tubulin," Cell 169(6): 1066-1077, 23 pages.
Anderson, K. C. et al. "Project 3. Oncogenomics to Identify and Validate Novel Targeted Therapies in Myeloma," National Institutes of Health Grant No. CA155258, Abstract (Funding Start Date: Dec. 1, 2011).
Anderson, K. C. et al. "Oncogenomics to Identify and Validate Novel Targeted Therapies in Multiple Myeloma," National Institutes of Health Grant No. CA155258, Abstract (Funding Start Date: Sep. 1, 2011).
Attal, M. et al. "Role of Combination Therapy with Novel Targeted Agents," National Institutes of Health Grant No. CA155258 (Funding Start Date: Sep. 1, 2011).
Avet Loiseau, H. et al. "Genomic Analysis to Gain Insights into Novel and Clinically Relevant Mol," National Institutes of Health Grant No. CA155258, Abstract (Funding Start Date: Sep. 1, 2011).
Avet Loiseau, H. et al. "Project 1. Developing MRD-based Therapeutic Strategy in Newly Diagnosed Multiple Myeloma," National Institutes of Health Grant No. CA155258, Abstract (Funding Start Date: Dec. 1, 2011).
Avet Loiseau, H. et al. "Core 2: Clinical and Tissue Core," National Institutes of Health Grant No. CA155258, Abstract (Funding Start Date: Dec. 1, 2011).
Baluja, S. et al. (Sep. 2017). "1-Octanol-water Partition Coefficient of Some Cyanopyridine and Chalcone Compounds," Rev. Colomb. Cienc. Quim. Farm. 46(3):342-356.
Bernkopf, D. B. et al. (Sep. 21, 2018). "Sulforaphane Inhibits Growth and Blocks Wnt/β-catenin Signaling of Colorectal Cancer Cells," Oncotarget 9(74):33982-33994.

(56) References Cited

OTHER PUBLICATIONS

Campbell, P. et al. "Core 4: Genome Sequencing Core," National Institutes of Health Grant No. CA155258, Abstract (Funding Start Date: Dec. 1, 2011).
Chakraborty, A. et al. "A Phase Separation Model for Transcriptional Control in Mammals," National Science Foundation Award No. 1743900 (Funding Start Date: Aug. 1, 2017).
Chen, H. et al. (Feb. 23, 2018). "Targeting Oncogenic Myc as a Strategy for Cancer Treatment," Signal Transduction and Targeted Therapy 3:1-7.
Epstein, C. B. et al. "Core 3: Epigenomics Core," National Institutes of Health Grant No. CA155258, Abstract (Funding Start Date: Dec. 1, 2011).
Futreal, P. A. et al. "Genome Sequencing Core," National Institutes of Health Grant No. CA155258, Abstract (Funding Start Date: Sep. 1, 2011).
Gallant, P. et al. (Dec. 1, 2009). "Myc's Secret Life without Max," Cell Cycle 8(23):3848-3853.
Harousseau, J.- L. et al. "Clinical and Tissue Core," National Institutes of Health Grant No. CA155258, Abstract (Funding Start Date: Sep. 1, 2011).
Housman, D. E. et al. "Molecular Genetics of Wilms' Tumor," National Institutes of Health Grant No. CA042063, Abstract (Funding Start Date: Oct. 1, 1996).
International Search Report and Written Opinion of the International Searching Authority mailed Nov. 24, 2023, for International Application No. PCT/US2023/071541, filed Aug. 2, 2023, 11 pages.
Jacks, T. E. "Investigaton of Small Regulatory RNAs in Tumor Development," National Institutes of Health Grant No. CA042063, Abstract (Funding Start Date: Sep. 15, 2006).
Jacks, T. E. "Project 1: Evolution of Transcriptional Programs in Lung Cancer Progression," National Institutes of Health Grant No. CA042063, Abstract (Funding Start Date: Jul. 1, 2017).
Jacks, T. E. et al. "Core 1—Shared Resources Core," National Institutes of Health Grant No. CA042063, Abstract (Funding Start Date: Jul. 1, 2017).
Jacks, T. E. et al. "Functional Analysis of the RB Tumor Suppressor Gene Family," National Institutes of Health Grant No. CA042063, Abstract (Funding Start Date: Oct. 1, 1996).
Jacks, T. E. et al. "Investigation of Regulatory RNAs in Tumor Development," National Institutes of Health Grant No. CA042063, Abstract (Funding Start Date: Jun. 1, 2012).
Kumar, D. et al. (2017, e-pub. Mar. 16, 2017). " Therapeutic Interventions of Cancers Using Intrinsically Disordered Proteins as Drug Targets: c-Myc as Model System," Cancer Informatics 16:1-7.
Lees, J. A. et al. "Cancer and Gene Regulation by the pRB/E2F Pathway," National Institutes of Health Grant No. CA042063, Abstract (Funding Start Date: Sep. 15, 2006).
Lees, J. A. et al. "Project 3: Targeting Epigenetic Regulators in Cancer," National Institutes of Health Grant No. CA042063, Abstract (Funding Start Date: Jul. 1, 2017).
Lees, J. A. et al. "Role of E2F in Regulation of Cell Cycle and Tumor Development," National Institutes of Health Grant No. CA042063, Abstract (Funding Start Date: Oct. 1, 1996).
Letzsch, S. et al. (2016). "Phenotypic Profiling of Autophagy Using Opera Phenix High-Content Screening System," PerkinElmer, 9 pages.
Levin, B. et al. (2021). "Harnessing the Power of Fluorescence to Characterize Biomolecular Condensates," Methods in Microbiology 48:1-47.
Ma, H. et al. (Jan. 2016). "α-lipoic Acid Protects Mouse Ovarian Granulosa Cells from Oxidative Stress and Apoptosis," Journal of Xi'an Jiaotong University (Medical Edition) 37(1):54-59. English Abstract.
Minvielle, S. et al. "Genomics Core," National Institutes of Health Grant No. CA155258, Abstract (Funding Start Date: Sep. 1, 2011).
Mitrea, D.M. et al. (Nov. 2022, e-pub Aug. 16, 2022). "Modulating Biomolecular Condensates: A Novel Approach to Drug Discovery," Nat Rev Drug Discov. 21(11):841-862.
Munshi, N. et al. "Administrative and Communication Core," National Institutes of Health Grant No. CA155258, Abstract (Funding Start Date: Sep. 1, 2011).
Munshi, N. et al. "Biostatistics and Bioinformatics," National Institutes of Health Grant No. CA155258, Abstract (Funding Start Date: Sep. 1, 2011).
Munshi, N. et al. "Core 1: Administrative and Communication Core," National Institutes of Health Grant No. CA155258, Abstract (Funding Start Date: Dec. 1, 2011).
Munshi, N. et al. "Integrative Oncogenomics of Multiple Myeloma (1 of 2)," National Institutes of Health Grant No. CA155258, Abstract (Funding Start Date: Dec. 1, 2011).
Munshi, N. et al. "Integrative Oncogenomics of Multiple Myeloma (2 of 2)," National Institutes of Health Grant No. CA155258, Abstract (Funding Start Date: Dec. 1, 2011).
Munshi, N. et al. "Integrative Oncogenomics of Multiple Myeloma," National Institutes of Health Grant No. CA155258, Abstract (Funding Start Date: Sep. 1, 2011).
Munshi, N. et al. "Project 4. Targeting Genomic Instability and Evolution in Myeloma," National Institutes of Health Grant No. CA155258, Abstract (Funding Start Date: Dec. 1, 2011).
Munshi, N. et al. "Targeting Genomic Instability and Evolution in Myeloma," National Institutes of Health Grant No. CA155258, Abstract (Funding Start Date: Sep. 1, 2011).
Parmigiani, G. L. et al. "Core 5: Biostatistics and Bioinformatics," National Institutes of Health Grant No. CA155258, Abstract (Funding Start Date: Dec. 1, 2011).
Sharp, P. A. "Biology of Oncogenes and Tumor Suppressor Genes," National Institutes of Health Grant No. CA042063, Abstract (Funding Start Date: Jul. 16, 2001).
Sharp, P. A. "Cancer and Gene Regulation by Non-coding RNAs," National Institutes of Health Grant No. CA042063, Abstract (Funding Start Date: Jun. 1, 2012).
Sharp, P. A. "Cancer and Gene Regulation by Short RNAs," National Institutes of Health Grant No. CA042063, Abstract (Funding Start Date: May 1, 2006).
Sharp, P. A. "Characterization of Pathways Controlling Cancer at the Level of Gene Regulation," National Institutes of Health Grant No. CA042063, Abstract (Funding Start Date: Sep. 15, 2006).
Sharp, P. A. et al. "Common Facilities and shRNA Vector Libraries," National Institutes of Health Grant No. CA042063, Abstract (Funding Start Date: Sep. 15, 2006).
Sharp, P. A. et al. "Core Facility," National Institutes of Health Grant No. CA042063, Abstract (Funding Start Date: Oct. 1, 1997).
Sharp, P. A. et al. "Expression by Oncogenes and Anti-Oncogenes," National Institutes of Health Grant No. CA042063, Abstract (Funding Start Date: May 1, 1991).
Sharp, P. A. et al. "Gene Regulation by Oncogenes and Tumor Suppressor Genes," National Institutes of Health Grant No. CA042063, Abstract (Funding Start Date: Sep. 15, 1996).
Sharp, P. A. et al. "Project 2: Pathways Controlling Cancer at the Level of Gene Regulation," National Institutes of Health Grant No. CA042063, Abstract (Funding Start Date: Jul. 1, 2017).
Sharp, P. A. et al. "Regulation of Gene Expression by Oncogenes," National Institutes of Health Grant No. CA042063, Abstract (Funding Start Date: May 1, 1986).
Sharp, P. A. et al. "Shared Bioinformatics Specialist and Facilities," National Institutes of Health Grant No. CA042063, Abstract (Funding Start Date: Jun. 1, 2012).
Sharp, P. A. et al. "Transcription Regulation by Oncogenes," National Institutes of Health Grant No. CA042063, Abstract (Funding Start Date: Oct. 1, 1996).
Verheyen, E. M. et al. (Jan. 2010). "Regulation of Wnt/beta-catenin Signaling by Protein Kinases," Dev Dyn. 239(1):34-44.
Vita, M. et al. (Sep. 2006). "The Myc Oncoprotein as a Therapeutic Target for Human Cancer," Seminars in Cancer Biology 16:318-330.
Wang, F. et al. (2020, e-pub. Aug. 16, 2020). "Targeting Stress Granules: A Novel Therapeutic Strategy for Human Diseases," Pharmacological Research 161:105143, 17 pages.
Watanabe, T. et al. (Nov. 28, 2018). "Alternative Splicing Regulator RBM20 and Cardiomyopathy," Frontiers in Molecular Biosciences 5(105):1-11.

(56) References Cited

OTHER PUBLICATIONS

Weintraub, A. S. et al. (Dec. 14, 2017, e-pub Dec. 7, 2017). "YY1 Is a Structural Regulator of Enhancer-Promoter Loops," Cell. 171(7):1573-1588, 59 pages.

Wong, K. K. et al. "Targeting the Transcriptional and Epigenetic Landscape in Chemo-refractory Small-Cell Lung Cancer," National Institutes of Health Grant No. CA213333, Abstract (Funding Start Date: Jun. 9, 2017).

Young, R. et al. "Project 2. Investigating Epigenetic Circuitry in Multiple Myeloma," National Institutes of Health Grant No. CA155258, Abstract (Funding Start Date: Dec. 1, 2011).

Young, R. et al. "Transcriptional Regulatory Network in Living Cells," National Institutes of Health Grant No. HG002668, Abstract (Funding Start Date: May 1, 2006).

Young, R. et al. "Transcriptional Regulatory Networks in Living Cells," National Institutes of Health Grant No. GM123511, Abstract (Funding Start Date: Jul. 1, 2017).

Young, R. et al. "Transcriptional Regulatory Networks in Living Cells," National Institutes of Health Grant No. GM123511, Abstract (Funding Start Date: May 2, 2003).

Young, R. et al. Project 2. Investigating Epigenetic Circuitry in Multiple Myeloma, National Institutes of Health Grant No. CA155258, Abstract (Funding Start Date: Aug. 1, 2017).

Zhang, J. H. et al. (Jan. 2008). "Z-Factor," Encyclopedia of Cancer 3227-3228.

Zhao, C. Y. et al. (Apr. 2015). "Role of Nrf2 in Neurodegenerative Diseases and Recent Progress of its Activators," Yao Xue Xue Bao 50(4):375-384. Machine Translation.

Zhu, C. et al. (Sep. 2017, e-pub. Jul. 1, 2017). "Insulin Regulates Titin Pre-mRNA Splicing through the PI3K-Akt-mTOR Kinase Axis in a RBM20-dependent Manner," Biochim Biophys Acta Mol Basis Dis. 1863(9):2363-2371.

Zirath, H. et al. (Jun. 3, 2013). "MYC Inhibition Induces Metabolic Changes Leading to Accumulation of Lipid Droplets in Tumor Cells," PNAS 110(25):10258-10263.

Salojin, C. et al. (Apr. 5-10, 2024). "Poster LB199: Condensate Modulator Sequesters Beta-catenin into Depot Condensates and Demonstrates Competitive Anti-tumor Activity in Animal Models of Colorectal Cancer,"American Association for Cancer Research Annual Meeting 2024 (AACR), 1 page.

Shiina, N. (2022). "Biomecular Condensate," J. Jpn Biochem. Soc. 94(4): 631-632. Partial English Translation.

U.S. Appl. No. 18/939,875, filed Nov. 7, 2024, for Beutel et al. (U.S. Patent Application is not submitted herewith pursuant to the waiver of 37 C.F.R. § 1.98(a)(2)(ill) issued by the Office on Sep. 21, 2004.).

FIG. 2D
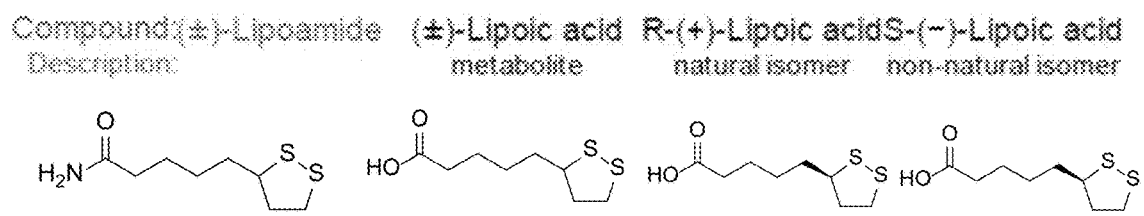
| Compound Description: | (±)-Lipoamide | (±)-Lipoic acid metabolite | R-(+)-Lipoic acid natural isomer | S-(−)-Lipoic acid non-natural isomer |
|---|---|---|---|---|
| $EC_{50}$ droplets: | 17.2 μM ↓ | 39.1 μM ↓ | 22.6 μM ↓ | 35.3 μM ↓ |
| partition: | 30.6 μM ↑ | ≈30 μM ↑ | ≈30 μM ↑ | ≈30 μM ↑ |
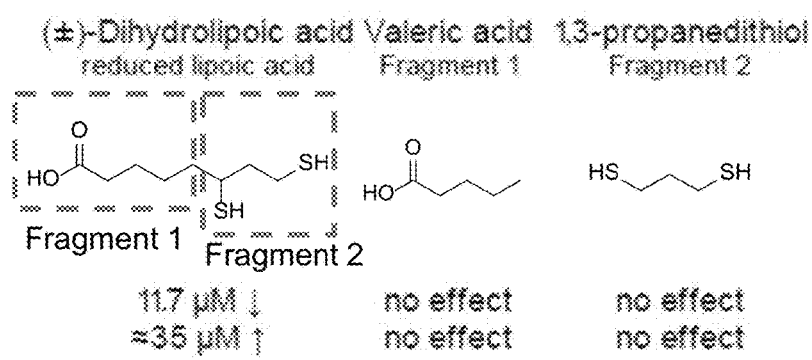
| (±)-Dihydrolipoic acid reduced lipoic acid | Valeric acid Fragment 1 | 1,3-propanedithiol Fragment 2 |
|---|---|---|
| 11.7 μM ↓ | no effect | no effect |
| ≈35 μM ↑ | no effect | no effect |

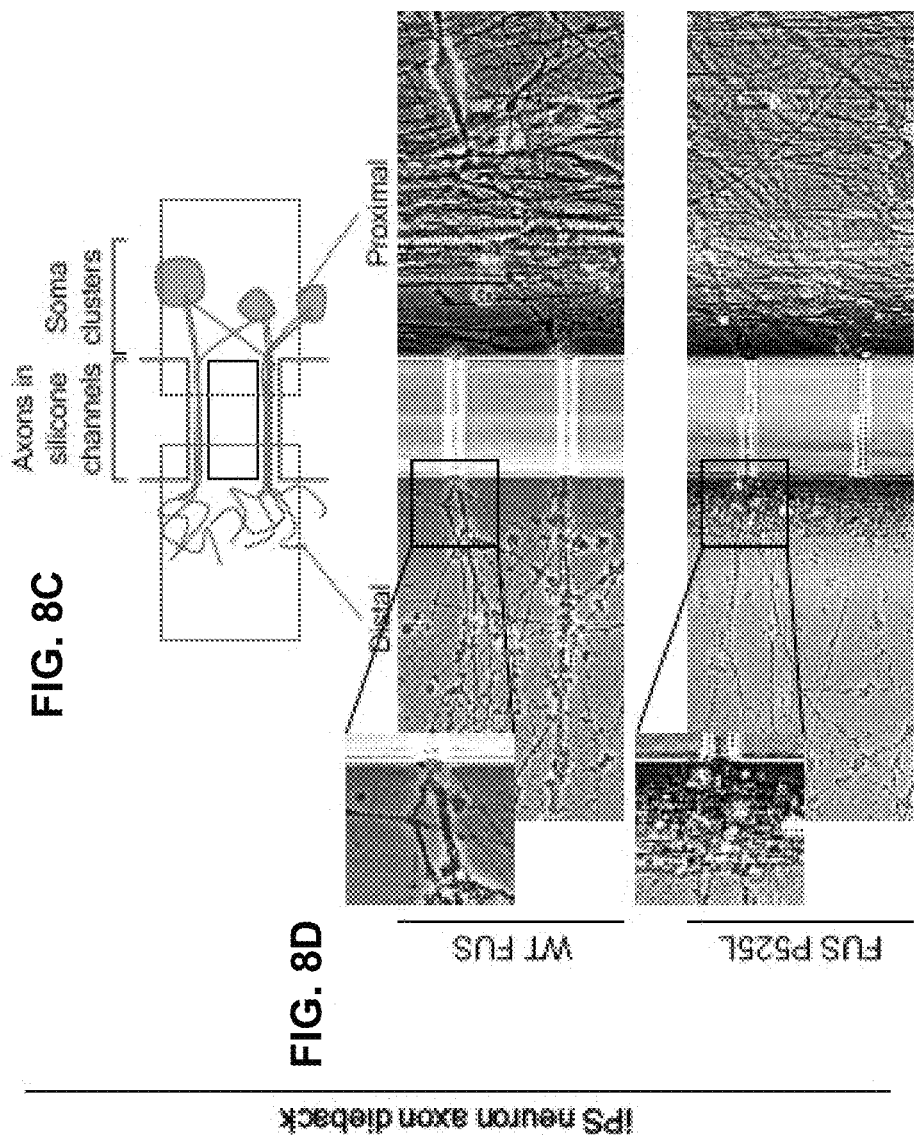
FIG. 8C
FIG. 8D
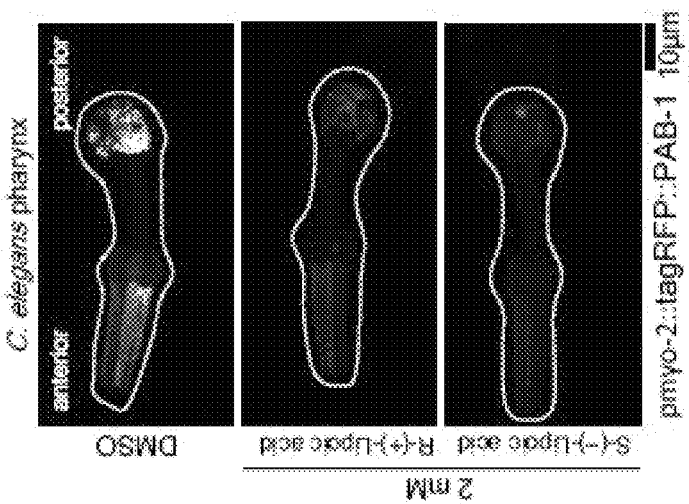
FIG. 8B

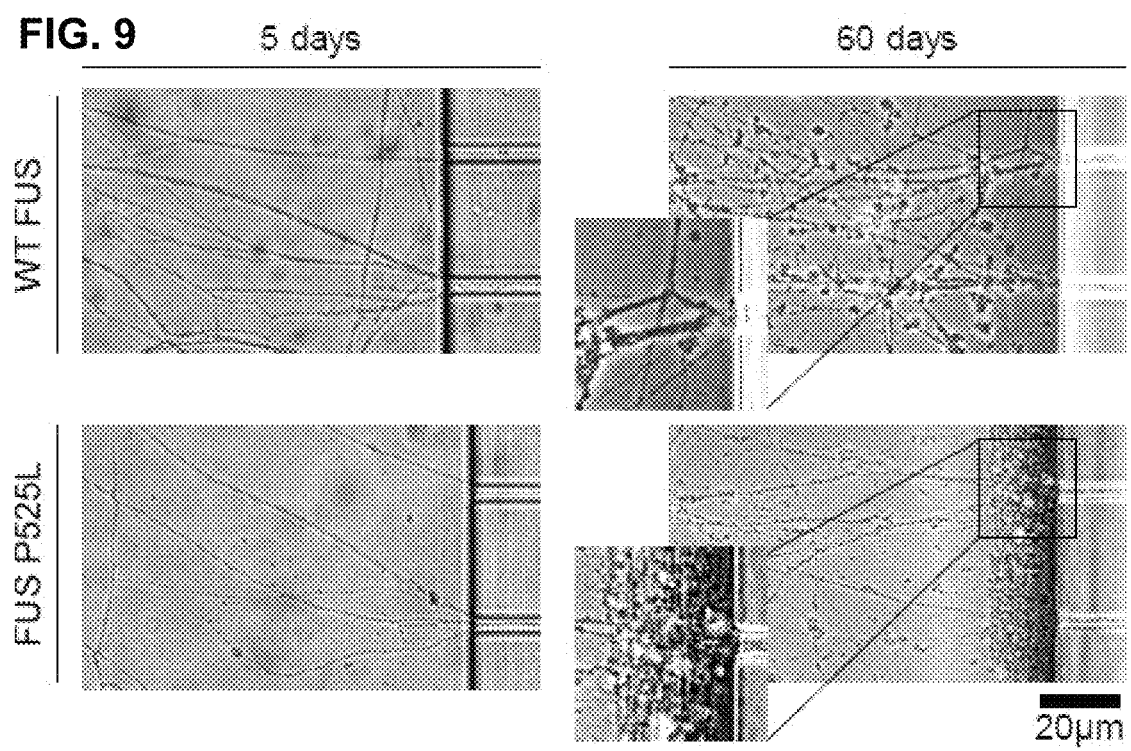

- ● FUS eGFP droplets per cell (left axis)
- ○ Normalised nuclear partition (right axis)

FIG. 10C
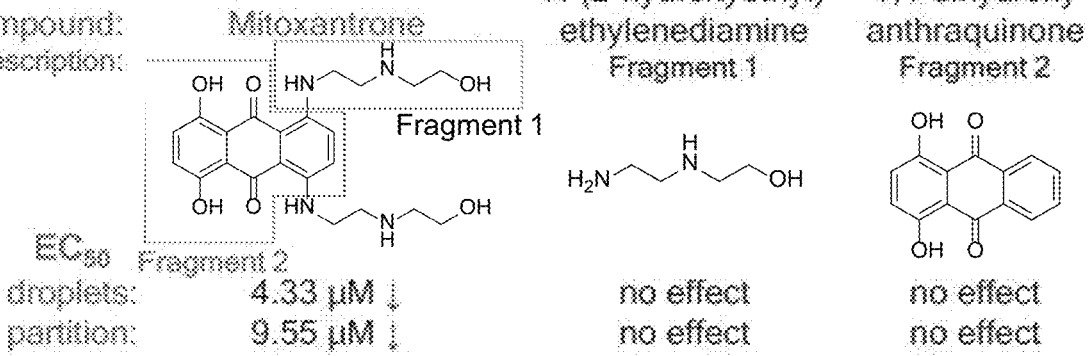
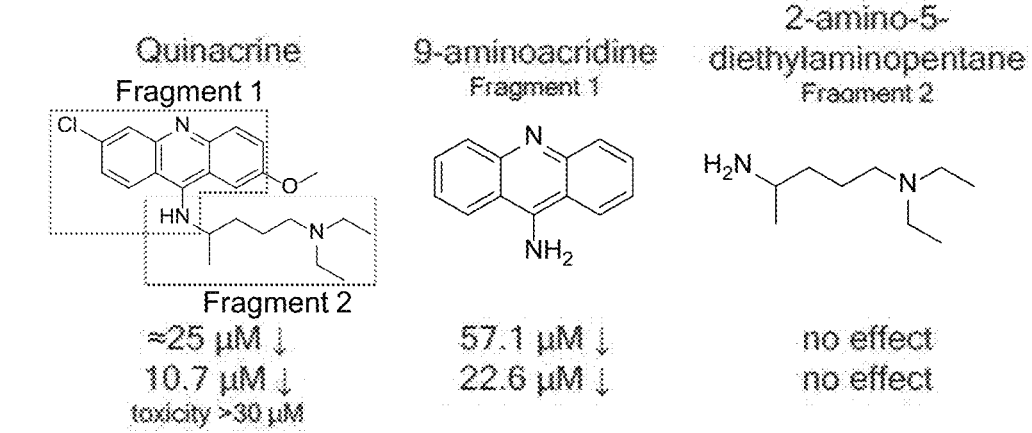
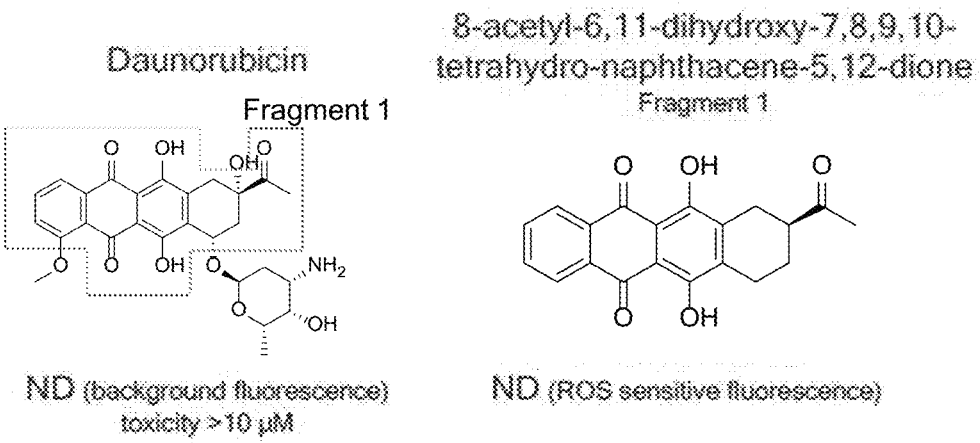

COMPOUNDS FOR TREATMENT OF DISEASES AND METHODS OF SCREENING THEREFOR

CROSS-REFERENCE TO RELATED APPLICATIONS

This application is a continuation of International Application PCT/EP2019/077818, with an international filing date of Oct. 14, 2019, and this application claims priority to EP18200401.0, filed on Oct. 15, 2018, and EP19189772.7, filed on Aug. 2, 2019, which are each hereby incorporated by reference in their entirety.

BACKGROUND

Amyotrophic lateral sclerosis (ALS) is a fatal neurodegenerative disease with poor prognosis and little options for therapy. Currently only two FDA approved drugs are available, riluzole and edaravone, however both only slow disease progression by a few months. The effects of riluzole and edaravone are not well understood and most likely do not directly target the underlying pathomechanism of the disease. New approaches are therefore critically needed. Most forms of ALS are sporadic but around 10% are monogenic disorders. Familial ALS-associated mutations are frequently found in RNA-binding proteins (RBPs) such as FUS and TDP-43. These RBPs have characteristic low complexity domains (LCDs).

The precise mechanism of ALS pathogenesis is not known; it is ambiguous whether aggregates or oligomers are toxic or if they cause loss of function of the proteins, and how this results in downstream effects. However, mutated TDP-43 and FUS often mislocalise to the cytoplasm where they promote stress granule formation and aberrant cytoplasmic aggregates associated with disease. One hypothesis in particular suggests that pathological stability of stress granules might be related to disease. This suggests dissolving stress granules and/or aggregates could ameliorate disease, whether or not pathogenesis is through a toxic gain of function or protein sequestration and loss of function.

Stress granules are liquid-like non-membrane bound compartments, and recent work has shown that LCD-containing proteins form these compartments by liquid-liquid phase separation. Therefore, in principle, it might be possible to target the physical chemistry driving stress granule formation. Indeed, there are known compounds which disrupt this phase separation, notably 1,6-hexanediol and similar alcohols. However these compounds suffer from two problems: First, they require extremely high concentrations (1-10%) and are toxic. Second, their effects are not specific to stress granules and they also affect other liquid-like non-membrane bound compartments. Many other compartments are also liquid-like, particularly in the nucleus.

There is a need for methods of identifying compounds that more specifically modulate phase separation of certain compartments for effective and specific treatment of ALS.

All references cited herein, including patent applications and publications, are incorporated by reference in their entirety.

BRIEF SUMMARY

In some aspects, the present disclosure provides a method of identifying a compound that modulates a characteristic associated with one or more condensates comprising a condensate-associated molecule, the method comprising: (a) contacting the compound with a cellular composition comprising one or more condensates or a cellular composition capable of forming one or more condensates, and (b) determining the characteristic associated with the one or more condensates, wherein a modulation in the characteristic, as compared to a reference, indicates that the compound modulates the characteristic associated with the one or more condensates.

In some embodiments, determining the characteristic associated with the one or more condensates is based on any one or more of the following: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates; (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the one or more condensates; and (xiii) aggregation of the condensate-associated molecule.

In some embodiments, the one or more condensates are within one or more cells in the cellular composition.

In some embodiments, the methods described herein further comprise subjecting the cellular composition to a condensate-forming condition prior to determining the characteristic associated with one or more condensates.

In some embodiments, the methods described herein further comprise subjecting the cellular composition to a condensate-forming condition prior to contacting a compound with a cellular composition.

In some embodiments, the condensate-forming condition is any one or more of: (i) an oxidative stressor; (ii) a mitochondrial electron transport chain inhibitor; (iii) a heat stressor; (iv) an osmotic stressor; (v) a hyperosmotic stressor; and (vi) glycolysis inhibition.

In some embodiments, the condensate-associated molecule is a polypeptide. In some embodiments, the condensate-associated molecule is a wildtype polypeptide. In some embodiments, the condensate-associated molecule is a mutant polypeptide. In some embodiments, the condensate-associated molecule is selected from the group consisting of: FUS, EWSR1, TIAL1, PABPC1, and G3BP1.

In some embodiments, the cell in the cellular composition expresses the condensate-associated molecule. In some embodiments, the cellular composition comprises a HeLA, iPSC, or iPSC MN cell.

In some embodiments, the methods described herein further comprise imaging at least a portion of the cellular composition.

In some embodiments, the methods described herein further comprise contacting at least a portion of the cellular composition with a fixative.

In some embodiments, the methods described herein further comprise contacting at least a portion of the cellular composition with a stain.

In some embodiments, the methods described herein further comprise contacting at least a portion of the cellular composition with a DNA-damaging condition. In some embodiments, the DNA-damaging condition is laser irradiation.

In some embodiments, the reference is a second condensate. In some embodiments, the reference is a second cellular composition.

In some embodiments, the methods described herein further comprise assessing the identified compound using a second cell-based assay.

In some embodiments, the methods described herein further comprise assessing the identified compound using a biochemical assay.

In some embodiments, the methods described herein further comprise assessing the identified compound using an in vivo assay.

In another aspect, the present disclosure provides a method of identifying a compound useful for treating a disease, the method comprising identifying a compound according to any one of the methods described herein. In some embodiments, the disease is a neurodegenerative disease. In some embodiments, the neurodegenerative disease is ALS.

The present invention relates to compounds for treatment of neurodegenerative disease associated with the formation of stress granules, particularly for treatment of amyotrophic lateral sclerosis.

One aspect of the invention relates to a compound selected from lipoic acid (5-(1,2-dithiolan-3-yl)pentanoic acid; CAS Nos 1200-22-2; 1077-27-6; 1077-28-7), lipoamide (5-(1,2-dithiolan-3-yl)pentanamide; CAS No 940-69-2) dihydrolipoic acid (6,8-dimercaptooctanoic acid; CAS No 462-20-4), and dihydrolipoamide (6,8-bis(sulfanyl)octanamide; CAS No 3884-47-7) for use in a method for preventing or treating a neurodegenerative disease associated with the formation of stress granules.

Particularly, the neurodegenerative disease is associated with the formation of stress granules in the cytosol of a cell comprised within the disease affected tissue.

Particularly, lipoic acid and/or lipoamide may be used in the R-Form, the S-form or as a racemate.

The skilled person is aware that any specifically mentioned compound may be present as a pharmaceutically acceptable salt of compound. Pharmaceutically acceptable salts comprise the ionized drug and an oppositely charged counterion. Non-limiting examples of pharmaceutically acceptable anionic salt forms include acetate, benzoate, besylate, bitatrate, bromide, carbonate, chloride, citrate, edetate, edisylate, embonate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate, phosphate, diphosphate, salicylate, disalicylate, stearate, succinate, sulfate, tartrate, tosylate, triethiodide and valerate. Non-limiting examples of pharmaceutically acceptable cationic salt forms include aluminium, benzathine, calcium, ethylene diamine, lysine, magnesium, meglumine, potassium, procaine, sodium, tromethamine and zinc.

In some embodiments, the compound of the invention is administered according to the following dosage regimen: administering a daily dose of 600 mg to 1,600 mg of the compound.

Advantageously, a daily dose of 600 mg may give a plasma concentration of 8 µM to 30 µM of the compound of the invention.

In some embodiments, the neurodegenerative disease associated with the formation of stress granules is selected from amyotrophic lateral sclerosis, Parkinson's disease, Alzheimer's disease and Huntington's disease.

In some embodiments, a pharmaceutical composition for use in a method for preventing or treating a neurodegenerative disease associated with formation of stress granules comprises the compound of the invention as recited in paragraph 0025.

In some embodiments, the pharmaceutical composition is formulated for oral application.

In some embodiments, the neurodegenerative disease associated with the formation of stress granules is amyotrophic lateral sclerosis.

Alternatively, a dosage form for use in a method for preventing or treating a neurodegenerative disease associated with the formation of stress granules is provided, wherein the dosage form comprises the compound of the invention, particularly a compound as recited in paragraph 0025.

Dosage forms may be for enteral administration, such as nasal, buccal, rectal, transdermal or oral administration, or as an inhalation form or suppository. Alternatively, parenteral administration may be used, such as subcutaneous, intravenous, intrahepatic or intramuscular injection forms. Optionally, a pharmaceutically acceptable carrier and/or excipient may be present.

In some embodiments, the dosage form is formulated for oral application.

In some embodiments, the neurodegenerative disease associated with the formation of stress granules is selected from amyotrophic lateral sclerosis, Parkinson's disease, Alzheimer's disease and Huntington's disease.

Alternatively, the aspect of treatment according to the invention can be formulated as a method for preventing or treating a neurodegenerative disease associated with the formation of stress granules, wherein the method comprises the administration of the compound of the invention to a patient in need thereof, particularly administration of a compound as recited in paragraph 0025.

In some embodiments, the compound is administered at a daily dose of 600 mg to 1,600 mg.

In some embodiments, the compound is administered orally.

In some embodiments, the neurodegenerative disease associated with the formation of stress granules is selected from amyotrophic lateral sclerosis, Parkinson's disease, Alzheimer's disease and Huntington's disease.

In some embodiments, the neurodegenerative disease associated with the formation of stress granules is amyotrophic lateral sclerosis.

In certain aspects, the invention relates to a method for reducing or inhibiting the formation of stress granules in a cell, wherein the method comprises the use of a compound selected from:
lipoic acid, lipoamide, dihydrolipoic acid, dihydrolipoamide,
a heterotricyclic compound, particularly an anthraquinone or anthraquinone derivative such as 1,4-dihydroxyanthraquinone,
an acridine or acridine derivative such as quinacrine or aminoacridine or mitoxantrone;
a tetracyclic compound, and a surfactant, particularly cetylpyridium chloride.

In some embodiments, the compound is provided in the culture medium, in which the cell is incubated.

It will also be understood by those skilled in the art that changes in the form and details of the implementations described herein may be made without departing from the scope of this disclosure. In addition, although various advantages, aspects, and objects have been described with reference to various implementations, the scope of this disclosure should not be limited by reference to such advantages, aspects, and objects.

BRIEF DESCRIPTION OF THE DRAWINGS

FIG. 1A) The sub-cellular localisation of FUS GFP in unstressed HeLa cells, stressed cells with compound solvent (DMSO) negative control, and with the positive controls dimercaprol (an arsenic chelating drug) and emetine (which prevents stress granule formation by stabilising polysomes). Stress causes nuclear export of FUS and formation of stress granules (cytoplasmic liquid FUS-containing droplets). FIG. 1B) Workflow for screening small molecules for effects on FUS GFP localisation in HeLa cells ex vivo. FIG. 1C) Ranked Mahalanobis distances for all 1600 compounds screened (mean from six fields of view) where high values mean more compound effect. Several automated measures of FUS localisation were combined into a single Mahalanobis distance score; the largest contributor were cytoplasmic FUS droplet number and area. A cut-off of 130 was used to select 47 compounds for further analysis. Dimercaprol and emetine are highlighted. FIG. 1D) Workflow for screening small molecules for effects on FUS liquid-liquid phase separation of purified FUS GFP in vitro. FIG. 1E) Ranked Z scores of change in droplet number and signal partition into FUS GFP droplets (formed under low salt conditions) where larger positive or negative values mean more compound effect. Scores were calculated at the maximum concentration at which the compound solvent (DMSO) negative control had no significant effect; 100 µM. Lipoamide, surfactant and heterotri-/tetracyclic compounds are indicated by data point colour, see FIG. 1F). FIG. 1F) Examples of the three classes of hit; lipoamide, cetylpyridinium chloride (surfactants), mitoxantrone (heterotri-/tetracyclic compounds). FIG. 1G) Appearance of the droplets with compound solvent (DMSO) negative control or examples of compound classes: cetylpyridinium chloride (surfactant), lipoamide or mitoxantrone (heterotricyclic). Note the larger drops with cetylpyridinium chloride and lipoamide and the fewer smaller drops with mitoxantrone.

FIGS. 2A-2D show the structure activity relationship of lipoamide-related compounds informs likely mechanism of action. FIG. 2A) Dose response of HeLa cell FUS GFP droplet number (•, left axis) and nuclear/cytoplasmic signal ratio (○, right axis) after 1 h pre-treatment with lipoamide followed by 1 h arsenate stress with continued lipoamide treatment. FIG. 2B) Dose response of iPS cell FUS GFP droplet number and nuclear/cytoplasm ratio, as in FIG. 2A). FIG. 2C) Dose response of HeLa cell FUS GFP droplet number and nuclear/cytoplasm ratio, with the same stress/treatment regime as FIG. 2A), for a range of compounds related to lipoamide. FIG. 2D) Summary of compounds structures and effect on cytoplasmic FUS droplet number and FUS nuclear partition.

FIG. 1A) Kinetics of loss of cytoplasmic FUS GFP droplets in HeLa cells pre-stressed for 1 h with arsenate then treated with 10 µM lipoamide (or DMSO solvent control) with continued arsenate stress. Example images 2 min and 100 min after addition of compound are shown on the right. Lipoamide can reverse the effect of existing arsenate stress. FIG. 2B) Images of HeLa cells expressing FUS GFP pre-treated with 10 µM lipoamide (or DMSO control) for 1 h, followed by 3 washes then 1 h arsenate stress. Lipoamide pre-treatment does not have a lasting effect on cells which prevents response to arsenate stress. FIG. 3C) Images of HeLa cells expressing GFP-labelled stress granule markers (EWSR1, TIAL1, PABC1 or G3BP1) following 1 h with arsenate stress and 10 µM lipoamide or isomers of lipoic acid, arsenate stress with DMSO solvent control, or DMSO without arsenate. Lipoamide and lipoic affect many stress granule components. FIG. 3D) Images of HeLa cells expressing FUS GFP subject to different stresses-rotenone (mitochondrial), no serum, sorbitol (osmotic), heat, arsenate or 6-deoxyglucose (glycolysis)—with concurrent treatment with 10 µM lipoamide or isomers of lipoic acid. Lipoamide and lipoic acid are active against several stresses, including mitochondrial, osmotic and oxidative stress.

FIG. 4A) Images of HeLa cells expressing Protein GFP markers of other non-membrane bound compartments subject to 1 h treatment with 10 µM compound (or DMSO control). Where unclear, the position of nuclei is indicated with a dotted outline. Lipoamide does not disrupt P bodies (DCP1A), Cajal bodies (COIL), DNA damage foci (TRP53BP1) or the nucleolus (NCB1), while mitoxantrone does have non-stress granule specific effects. FIG. 4B) Recruitment of FUS GFP to sites of UV laser-induced DNA damage in iPS cells after 1 h treatment with compound followed by 1 h arsenate stress. Top row shows FUS GFP fluorescence prior to the laser cut, stress granules are indicated with an arrow. Bottom row shows mean FUS GFP signal intensity response to DNA damage and one standard deviation above and below the mean. Mitoxantrone prevents formation of nuclear FUS droplets at the sites of DNA damage at under the cytoplasmic droplet number $EC_{50}$ while lipoamide does prevent formation of nuclear FUS droplets.

FIG. 5A) Schematic illustrating the quantitation of condensate droplet liquidity using optical tweezers. Two droplets are brought into contact and begin to fuse the time taken to relax to a single spherical droplet (once adjusted for droplet size) is a measure of the viscosity to surface tension ratio of the droplet—a measure of liquidity. Representative of two independent replicates. FIG. 5B) Droplet size-corrected relaxation times for droplet fusions with either 300 µM lipoamide or equivalent DMSO solvent control (0.3%). Box represents the $25^{th}$, $50^{th}$ and $75^{th}$ percentiles, whiskers represent 5th and 95th percentiles. Lipoamide reduces fusion time indicating lower viscosity and/or greater surface tension. FIGS. 5C-5E) Effect of 10 µM lipoamide on G156E FUS GFP condensates (formed under dextran crowding) on 'aging' while shaking, relative to an equivalent DMSO solvent control (0.1%). These conditions match those previously published[7]. FIG. 5C) Representative images after 30 h aging, showing fibre formation in the DMSO sample. FIG. 5D) Representative fluorescence recovery after photobleaching (FRAP) time series of FUS condensates and fibres during aging. FIG. 5E) Quantitation of FRAP in FIG. 5C). Error bars represent standard deviation. Aged condensates treated with lipoamide maintain large FUS GFP mobile fraction and short FRAP half-life while untreated condensates harden Effect of lipoamide and lipoic acid on G156E FUS GFP condensate 'aging' while shaking, relative to an equivalent DMSO solvent control (0.3%). Both compounds delay fibre formation.

FIG. 6A) Droplets formed by 2.8 µM FUS GFP in vitro with different concentrations of KCl (which inhibits droplet formation) with 100 µM lipoamide, lipoic acid or equivalent DMSO solvent control (1%). Lipoamide and lipoic acid subtly promote droplet formation. FIG. 6B) Effect of lipoamide and lipoic acid on G156E FUS GFP droplet 'aging' while shaking, relative to an equivalent DMSO solvent control (0.3%). Both compounds delay fibre formation. FIG. 6C) Representative fluorescence recovery after photobleaching (FRAP) of FUS droplets and fibres formed during the aging shown in FIG. 6B). Aged droplets treated with lipoamide or lipoic acid retain fast FRAP indicating liquidity. FIG. 6D) Quantitation of fluorescence signal intensity illustrated in FIG. 6C). Error bars represent standard deviation. Lipoamide and lipoic acid treatment allow droplets to maintain large FUS GFP mobile fraction and short FRAP half-life when untreated droplets harden.

FIG. 7A) $_{15}$N R-(+) and (+)-lipoamide were synthesised and characterised. Using a $_{15}$N-edited $_1$H-detected 1D HSQC NMR experiment, the two amide protons could be selectively detected in biological media and in HeLa cell pellets. The trans-amide proton (resonance at 6.9 ppm) was amenable to quantification by NMR. Below pH 8.5, 10° C., the intensity of the signal was proportional to lipoamide concentration. For detail, see supplemental methods. FIG. 7B) Uptake of lipoamide by HeLa cells was measured by exposing cells to $_{15}$N lipoamide then fractionating the samples and using NMR signal intensity from the trans-amide proton to measure $_{15}$N lipoamide concentration. Medium with 100 µM $_{15}$N lipoamide was incubated for 1 h in the absence or presence of HeLa cells. Following removal of medium, the cells were washed with medium (without arsenate) and detached using EDTA-trypsin. Solution or cell pellet/in-cell NMR was used to determine $_{15}$N lipoamide concentration. Example spectra for cells stressed with 3 mM arsenate and incubated with R-(+)-lipoamide are shown with the same y axis scale. FIG. 7C) Cellular uptake was determined by subtracting signal from medium incubated with cells (red) from signal from medium without cells (cyan). This was carried out for all four combinations of stressed (3 mM arsenate) or unstressed cells with $_{15}$N R-(+) or (+)-lipoamide. For stressed cells treated with $_{15}$N R-(+)-lipoamide the high signal intensity from the washed cell sample (green) is consistent with the large uptake from the medium calculated from the with (red) and without cell (cyan) signal intensity. FIG. 7D) Quantitation of FIG. 7C) showing percentage uptake and calculated intracellular concentration, assuming that lipoamide is uniformly distributed within cells (see Supplemental Methods). Uncertainty in measurement was approximately 30% and there was no significant difference in uptake between conditions. All measurements indicated substantial uptake of lipoamide and cellular concentrations >1 mM.

FIGS. 8A-8H show that lipoamide and lipoic acid have beneficial effects on in vitro and in vivo ALS models. FIGS. 8A-8B) Lipoic acid reduces age-induced aggregation of stress granule but not non-stress granule proteins in *C. elegans*. FIG. 8A) Toxicity and the effect on protein aggregation of R-(+)- or S-(−)-lipoic acid in worms overexpressing fluorescently tagged proteins prone to aggregation. Incidence of PAB-1 aggregation in the pharyngeal muscles was scored from the proportion of cells with >10 aggregates. Incidence of RHO-1 and KIN-19 were scored on a low, medium, high scale-see methods. Toxicity was assessed from the proportion of abnormally small or dead animals. Both isomers of lipoic acid caused strong dose-dependent reduction of aggregation of PAB-1 but not RHO-1 or KIN-19. Significant changes from the DMSO control are indicated, Fisher's exact test. * $p<0.0001$,  $p<0.001$, * $p<0.01$. Error bars represent standard error of proportion, $n>100$ for each sample. FIG. 8B) Z projections of confocal microscope stacks through the pharynx of worms expressing fluorescently tagged PAB-1 with or without lipoic acid treatment showing reduced aggregate number. FIGS. 8C-8E) Lipoic acid and lipoamide on dieback of neurons derived from iPS cells expressing FUS P525L, associated with familial ALS. FIG. 8C) Schematic of neuron culture, showing the channels through which the axons grow from the soma on the right. The region shown in micrographs in FIGS. 8D-8E) is indicated. FIG. 8D) iPS-derived neurons after 60 days in culture with 0.02% DMSO. Neurons expressing wild-type FUS have stable axons, while neurons expressing FUS P525L have unstable axons which die back leaving material around the exit point of axons from the channels. FIG. 8E) iPS-derived neurons expressing FUS P525L after 60 days in culture in the presence of 2 µM lipoamide or racemic, R-(+)- or S-(−)-lipoic acid. Representative images from a blinded experiment which also included the DMSO (solvent control) treated neurons shown in FIG. 8C). FIG. 8F) Lipoic acid recovers defects in motor function of *D. melanogaster* overexpressing human wild type FUS or ALS-associated FUS mutations. Overexpression of FUS leads to motor defects and the animals are unable to climb. Treatment with lipoic acid showed a dose-dependent increase in the ability of animals expressing wild-type FUS, FUS P525L or FUS R512C to climb. ** $p<0.005$, * $p<0.05$, one-way ANOVA. FIG. 8G) Lipoamide also recovers defects in motor function of *D. melanogaster*. Equivalent conditions to FIG. 8F) are shown, with lipoamide treatment in place of lipoic acid. * $p<0.05$, ** $p<0.005$, Student's T test. FIG. 8H) Lipoic acid recovers defects in motor function of *D. melanogaster* overexpressing human wild type FUS or ALS-associated FUS mutations. Overexpression of FUS leads to motor defects and the animals are unable to climb. ** $p<0.005$, * $p<0.05$, one-way ANOVA.

FIG. 9 shows iPS-derived neurons after 5 days and 60 days in culture with 0.02% DMSO. Neurons expressing wild-type FUS have stable axons, while neurons expressing FUS P525L have unstable axons which die back leaving material around the exit point of axons from the channels.

FIGS. 10A-10C show that structure activity relationship of heterotricyclic compounds implicates the tricyclic core as responsible for activity. FIG. 10A) Dose response of HeLa cell FUS GFP droplet number (•, left axis) and nuclear/cytoplasmic signal ratio (○, right axis) after 1 h pre-treatment with mitoxantrone followed by 1 h arsenate stress with continued mitoxantrone treatment. FIG. 10B) Dose response of HeLa cell FUS GFP droplet number and nuclear/cytoplasm ratio, with the same stress/treatment regime as FIG. 10A), for a range of compounds related to mitoxantrone and other heterotricyclic hits, quinacrine and the tetracycline antibiotic family. FIG. 10C) Summary of compounds structures and effect on cytoplasmic FUS droplet number and FUS nuclear partition.

FIG. 11A) FUS GFP localisation in isogenic iPS cells expressing either wild-type or P525L FUS GFP under combinations of 1 h arsenate stress followed by 1 h stress with 30 µM lipoamide or DMSO negative control treatment. FUS P525L causes formation of larger cytoplasmic FUS droplets which are still sensitive to lipoamide. FIG. 11B) Relative optical densities of aggregated FUS assessed by filter retardation from the iPS cells in FIG. 11A) following 1 h pre-treatment with 100 µM lipoamide or DMSO solvent control followed by 1 h arsenate stress or no stress. Significant changes (Student's t-test) are indicated, n=5. FIG. 11C) Anti-FUS and anti-GAPDH Western blots following the cell treatments in FIG. 11B). No significant change in FUS expression level relative to GAPDH was detected (Student's t-test, n=3). *anova*

FIG. 12A) Example kymographs of lysosome movement in the distal portion of FUS P525L GFP motor neuron axons after 3 days treatment with compound solvent (DMSO) or 2 µM lipoamide. Lysotracker fluorescence. FIG. 12B) Proportion of lysotracker-labelled lysosomes moving with an average speed greater than 2 µm/s following 3 days treatment with 2 µM lipoamide or equivalent DMSO concentration solvent control for motor neurons expressing either P525L or wild-type FUS. n=5 (P525L) or n=3 (wild-type) biological replicates, analysing 5 axon bundles per replicate. Lipoamide significantly increased lysosome transport (Student's T-test).*anova*

FIG. 13A) The chemical structure of $^{15}N$ lipoamide. FIG. 13B) Resonances in the $^1H$ NMR spectrum can be unambiguously assigned to individual protons of $^{15}N$ lipoamide in $CDCl_3$. FIG. 13C) $^{15}N$ filtered NMR experiments were acquired that show the cis-amide and trans-amide protons (environments 13 and 14 respectively) of lipoamide. The relative signal intensities sensitive to local solution conditions, indicating chemical exchange at 37° C. FIG. 13D) At pH 8.3, the intensity of both resonances decreased with increasing temperature. This indicated chemical exchange where local molecular dynamics and/or interactions with $H_2O$ on ms to us timescale reduce the signal. Below 15° C., the intensity of the trans-amide resonance (14) approaches a plateau, indicating a slow exchange regime where signal intensity is an unambiguous measure of concentration. FIG. 13E) At 10° C., the intensity of the cis- and trans-amide proton resonances increased with decreasing pH indicating the presence of ms to us second dynamics. Below pH 8.6, the intensity of the trans-amide proton was constant, indicating a slow exchange regime. Together, FIG. 13D) and FIG. 13F) indicate at 10° C. and below pH 8.6 integrated signal intensity of the trans-amide proton of lipoamide in $^{15}N$ edited $^1H$ NMR experiments is a reliable proxy for concentration. FIG. 13F) Signal intensity of the trans-amide proton of lipoamide, when dissolved in growth medium, decreased over time at 37° C. but not at 10° C. At 10° C. signal intensity is stable for >10 h experiments. FIG. 13G) The signal intensity of both the cis- and trans-amide protons under different experimental conditions. This is an expanded version of FIG. 13B, which only shows the trans-amide proton, and includes one additional condition: v) Cells (from iii) disrupted with Triton X-100 and DNaseI. Taken together, i) to iv) imply lipoamide is taken up by HeLa cells in a mobile form while most of the molecules were unmodified (with uptake quantified in FIGS. 13C-13D). FIG. 13H) An expanded view of the spectra in FIG. 13G) i) and v). On disruption of cells with Triton X-100 and DNaseI the spectrum changed significantly, indicating chemical modification of lipoamide when cellular compartments are disrupted.

DETAILED DESCRIPTION

Figure 1A:
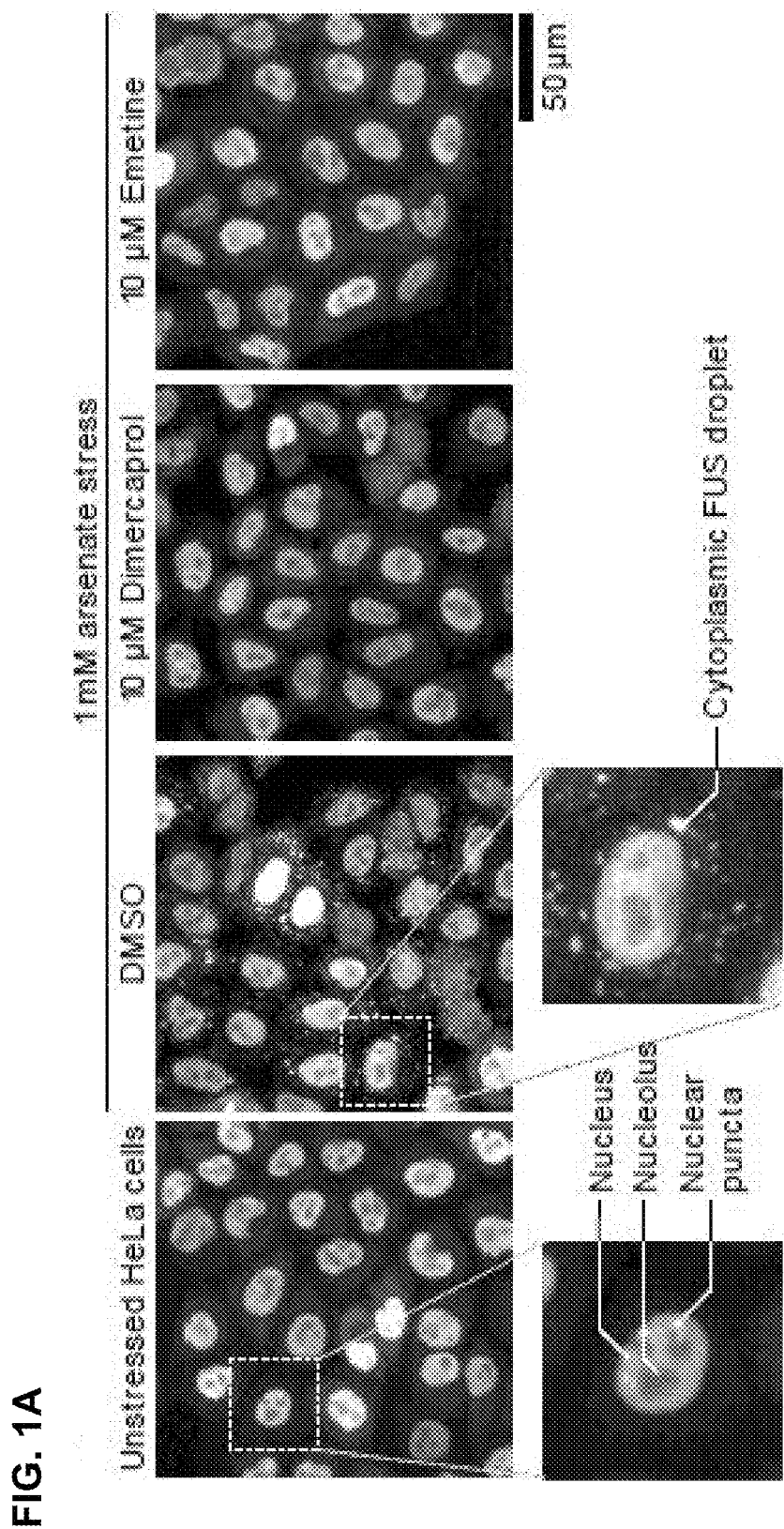
FIGS. 1A-1G show the screening for small compounds which affect FUS-containing stress granule formation ex vivo in HeLa cells.

The invention includes, in some aspects, methods of identifying compounds that modulate condensates, and applications thereof, such as the usefulness of such compounds in the treatment of diseases.

Traditionally, the various membrane-bound compartments (organelles) of cells were thought to be a crowded jumble of macromolecules and metabolites, all freely mixing with each other, randomly diffusing within the confines of the membrane that delineates that particular compartment (the nucleus, cytosol, mitochondria, endoplasmic reticulum, etc.). Cellular processes were thought to be regulated by the interactions of these molecules, driven by specific binding sites that would lead to biochemical reactions (enzymatic activities such as transcription, RNA processing, metabolic reactions, signaling molecule reactions like phosphorylation, etc.) between the molecules. For example, a kinase diffuses until it happens to bind to a protein that it recognizes as its target, binds to it and phosphorylates it.

What is now clear from recent work is that macromolecules sort inside the membrane-bound organelles into condensates based on the intrinsic physical properties of proteins, RNA, and/or DNA. The macromolecules assemble, or condense, into liquid droplets in a phase separation reaction, resulting in specific proteins and/or nucleic acid molecules being concentrated inside the condensates while other specific proteins and/or nucleic acids are excluded.

The process of forming condensates is not driven by specific simple stoichiometric binding events, as previously thought, but rather by a phase separation reaction. This is a layer of architecture within the cell that organizes macromolecules throughout the cell into sub-compartments to increase the specificity of reactions and drive reactions through higher local concentrations.

Notably, condensates are liquid and reversible, so that upon changes in cell physiology (e.g., a signaling event, a change in concentration of one of the macromolecules or other changes in the local environment), the different condensates within the cell will change, sometimes completely dissolving, other times more subtly altering their molecular composition. This is, therefore, a primary mechanism for regulation of almost all reactions within the cell, synergizing with the previously understood mechanism of specific binding events.

Some diseases, including neurodegenerative diseases like ALS, appear to be caused by aberrant aggregates of proteins accumulating in the cell. Previous attempts to screen for drugs that prevent or disrupt these aggregates were not based on the new understanding of condensates. The disclosure of the present application is based, at least in part, on the inventors' unique insight that the phase separation of macromolecules into condensates is, in this case, an intermediate step that occurs before the proteins then form aberrant aggregates, so by using assays that directly monitor the effect of compounds on condensate formation and properties, new useful compounds for treating such diseases can be discovered.

In some aspects, the methods disclosed herein allow for the identification of compounds that modulate certain aspects of condensate behavior. For examples, some aspects of the methods disclosed herein allow for the identification of compounds that modulate liquidity, but not the formation of condensates. Further, using the methods described herein, the inventors identified compounds that did not simply disrupt all condensate formation, but appeared specific to a condensate of interest. Such specificity could potentially improve potency and reduce side effects such as toxicity.

The present application provides novel methods for identifying compounds that modulate one or more characteristics of cellular and extracellular condensates and consequently are useful for treating condensate-associated diseases. The methods focus on changes in the behavior or characteristics of one or more condensates, thus allowing for identification of compounds without necessarily having knowledge about the specific molecular target of each compound. This allows one to quickly screen for potentially useful compounds in simple and elegant behavior assays. Exemplary characteristics of the condensates include, but are not limited to, (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates; (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the one or more condensates; and (xiii) aggregation of the condensate-associated molecule. Compounds of desired properties can be identified by evaluating their ability to modulate some (such as any of the 1, 2, 3, 4, 5, 6, 7, 8, 9, 10, 11, 12, 13) or all of the characteristics of one or more condensates. Additionally, compounds of desired properties can be identified by evaluating their ability to modulate some but not other characteristics of the condensates, or ability to modulate some but not other condensates. Using the methods described herein, compounds which target the physical chemistry of condensates formed by liquid-liquid phase separation have been identified.

Thus, in some aspects, provided herein are methods of screening for compounds that modulate a characteristic associated with one or more condensates and/or are useful in methods of treating a disease. In some aspects, provided herein are methods of high throughput screening for compounds that modulate a characteristic associated with one or more condensates and/or are useful in methods of treating a disease.

In some embodiments, the method comprises: (a) contacting the compound with a cellular composition comprising one or more condensates or with a cellular composition that is capable of forming one or more condensates, and (b) determining the characteristic associated with the one or more condensates. In some embodiments, a modulation in the characteristic indicates that the compound modulates the characteristic associated with the one or more condensates. In some embodiments, a modulation in the characteristic, as compared to a reference, indicates that the compound modulates the characteristic associated with the one or more condensates. In some embodiments, the method comprises determining a plurality of characteristics associated with the one or more condensates.

In some embodiments, the method comprises: (a) contacting a plurality of candidate compounds with a cellular composition comprising one or more condensates or with a cellular composition that is capable of forming one or more condensates, and (b) determining the characteristic associated with the one or more condensates, wherein a modulation in the characteristic, as compared to a reference, indicates that the candidate compound modulates the characteristic associated with the one or more condensates, thereby obtaining the compound that modulates a characteristic of one or more condensates.

In some aspects, provided herein are methods of identifying a compound that modulates a characteristic associated with a first set of one or more condensates comprising a first condensate-associated molecule, the methods comprising: (a) contacting the compound with a cellular composition comprising the first and second set of one or more condensates or with a cellular composition that is capable of forming the first and second set of one or more condensates, and (b) determining the characteristic associated with the first set of one or more condensates, and (c) determining the characteristic associated with the second set of one or more condensates.

In some aspects, provided herein are methods of identifying a compound that modulates a characteristic associated with a first set of one or more condensates comprising a first condensate-associated molecule, the method comprising: (a) contacting the compound with a cellular composition comprising the first and second set of one or more condensates or with a cellular composition that is capable of forming the first and second set of one or more condensates, and (b) determining the characteristic associated with the first set of one or more condensates, and (c) determining the characteristic associated with the second set of one or more condensates.

In some aspects, provided herein are methods of screening (such as high throughput screening) for compounds that modulate a characteristic associated with a first set of one or more condensates comprising a first condensate-associated molecule, the method comprising: (a) contacting a plurality of candidate compounds with a cellular composition comprising the first set of one or more condensates or with a cellular composition that is capable of forming the first set of one or more condensates, and (b) determining the characteristic associated with the first set of one or more condensates, (c) contacting the plurality of candidate compounds with a cellular composition comprising a second set of one or more condensates comprising a second condensate-associated molecule or that is capable of forming the second set of one or more condensates, and (d) determining the characteristic associated with the second set of one or more condensates.

In some embodiments, a modulation in the characteristic associated with the first set that is different from a modulation in the characteristic associated with the second set indicates that the candidate compound modulates the characteristic associated with the first set of one or more condensates, thereby obtaining the compound that modulates a characteristic associated with the first set one or more condensates. In some embodiments, a modulation in the characteristic associated with the second set that is different from a modulation in the characteristic associated with the first set, as compared to a reference, indicates that the compound modulates the characteristic associated with the second set of one or more condensates, thereby obtaining the compound that modulates a characteristic associated with the second set one or more condensates.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-translational modifications of the polypeptide, for example, glycosylation, sialylation, acetylation, phosphorylation, and the like.

The term "polynucleotide" or "nucleic acid" as used herein refers to a polymeric form of nucleotides of any length, including ribonucleotides and deoxyribonucleotides. Thus, this term includes, but is not limited to, single-, double- or multi-stranded DNA or RNA, genomic DNA, cDNA, mRNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. The backbone of the polynucleotide can comprise repeating units, such as N-(2-aminoethyl)-glycine, linked by peptide bonds (e.g., peptide nucleic acid). Alternatively, the backbone of the polynucleotide can comprise a polymer of synthetic subunits such as phosphoramidates and thus can be an oligodeoxynucleoside phosphoramidate (P-NH2) or a mixed phosphoramidate-phosphodiester oligomer.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

As used herein a "condensate" means a non-membrane-encapsulated compartment formed by phase separation of one or more of proteins and/or other macromolecules (including all stages of phase separation).

As used herein a "condensate-associated molecule" means a molecule that can be found in or on a condensate under physiological or pathological conditions.

The term stress granules in the context of the present specification relates to liquid-like non-membrane bound compartments located within the nucleus or the cytosol of a cell and comprising proteins and RNA, which appear when the cell is under stress.

The term neurodegenerative disease in the context of the present specification relates to a medical condition that is characterized by a progressive loss of structure or function of neurons. Non-limiting examples of neurodegenerative disease comprise amyotrophic lateral sclerosis, Parkinson's disease, Alzheimer's disease and Huntington's disease.

As used herein, the term treating or treatment of any disease or disorder (e.g., ALS) refers in one embodiment, to ameliorating the disease or disorder (e.g., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. As used herein, the term prevent or preventing or prevention of any disease or disorder (e.g., ALS) refers to the suppression, including complete suppression, of the development or onset of the disease or disorder (e.g., delaying the development or onset of the disease or disorder). Methods for assessing treatment and/or prevention of disease are generally known in the art, unless specifically described hereinbelow.

The section headings used herein are for organizational purposes only and are not to be construed as limiting the subject matter described.

Methods of Screening and Identifying Compounds

In some aspects of the application, methods of identifying compounds that modulate a characteristic associated with one or more condensates and/or are useful in methods of treating a disease are provided. In some aspects, provided herein are methods of screening for compounds that modulate a characteristic associated with one or more condensates and/or are useful in methods of treating a disease. In some aspects, provided herein are methods of high throughput screening for compounds that modulate a characteristic associated with one or more condensates and/or are useful in methods of treating a disease.

Described in more detail below are techniques for identifying compounds. Those skilled in the art will recognize that, in view of the provided description, several embodiments are possible within the scope and spirit of the disclosure of this application.

In some aspects, provided herein are methods of identifying a compound that modulates a characteristic associated with one or more condensates comprising a condensate-associated molecule, the method comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates. In some embodiments, the method comprises determining a single characteristic associated with the one or more condensates. In some embodiments, the method comprises determining a plurality of characteristics associated with the one or more condensates.

In some aspects, provided herein are methods of screening (such as high throughput screening) for compounds that modulate a characteristic associated with one or more condensates, the methods comprising assessing each of a plurality of compounds in a screen using any of the methods described herein. In some embodiments, the method of screening (such as high throughput screening) for a compound that modulates a characteristic associated with one or more condensates comprising a condensate-associated molecule, comprises: (a) contacting each of a plurality of candidate compounds with a cellular composition comprising one or more condensates or with a cellular composition that is capable of forming one or more condensates, and (b) determining the characteristic associated with the one or more condensates, wherein a modulation in the characteristic, as compared to a reference, indicates that the candidate compound modulates the characteristic associated with the one or more condensates, thereby obtaining the compound that modulates a characteristics of one or more condensates. In some embodiments, the method comprises determining a plurality of characteristics associated with the one or more condensates. In some embodiments, the plurality of compounds comprises at least any of 100, 200, 300, 500, 800, 1000, 1500, 3,000, 5,000, 10,000 or more different candidate compounds. In some embodiments, the plurality of candidate compounds are allowed to be in contact with the cellular composition in separate reactions (e.g., separate wells or vessels). In some embodiments, the plurality of candidate compounds are allowed to be in contact with the cellular compositions in separate reactions simultaneously.

In some aspects, provided herein are methods of identifying a compound that modulates a characteristic associated with a first set of one or more condensates comprising a first condensate-associated molecule, the methods comprising: (a) contacting the compound with a cellular composition comprising the first and second set of one or more condensates or with a cellular composition that is capable of forming the first and second set of one or more condensates, (b) determining the characteristic associated with the first set of one or more condensates, and (c) determining the characteristic associated with the second set of one or more condensates, wherein a modulation in the characteristic associated with the first set that is different from a modulation in the characteristic associated with the second set, as compared to a reference, indicates that the compound modulates the characteristic associated with the first set of one or more condensates.

In some aspects, provided herein are methods of identifying a compound that modulates a characteristic associated with a first set of one or more condensates comprising a first condensate-associated molecule, the methods comprising: (a) contacting the compound with a cellular composition comprising the first set of one or more condensates or with a cellular composition that is capable of forming the first set of one or more condensates, (b) determining the characteristic associated with the first set of one or more condensates, (c) contacting the compound with a cellular composition comprising a second set of one or more condensates comprising a second condensate-associated molecule or with a cellular composition that is capable of forming the second set of one or more condensates, and (d) determining the characteristic associated with the second set of one or more condensates wherein a modulation in the characteristic associated with the first set that is different from a modulation in the characteristic associated with the second set, as compared to a reference, indicates that the compound modulates the characteristic associated with the first set of one or more condensates.

In some aspects, provided herein are methods of screening (such as high throughput screening) for compounds that modulate a characteristic associated with a first set of one or more condensates comprising a first condensate-associated molecule, the methods comprising: (a) contacting a plurality of candidate compounds with a cellular composition comprising the first and second set of one or more condensates or with a cellular composition that is capable of forming the first and second set of one or more condensates, (b) determining the characteristic associated with the first set of one or more condensates, and (c) determining the characteristic associated with the second set of one or more condensates, wherein a modulation in the characteristic associated with the first set that is different from a modulation in the characteristic associated with the second set, as compared to a reference, indicates that the compound modulates the characteristic associated with the first set of one or more condensates, thereby obtaining the compound that modulates a characteristic associated with the first set of one or more condensates.

In some aspects, provided herein are methods of screening (such as high throughput screening) for compounds that modulate a characteristic associated with a first set of one or more condensates comprising a first condensate-associated molecule, the methods comprising: (a) contacting a plurality of candidate compounds with a cellular composition comprising the first set of one or more condensates or with a cellular composition that is capable of forming the first set of one or more condensates, (b) determining the characteristic associated with the first set of one or more condensates, (c) contacting a plurality of candidate compounds with a cellular composition comprising a second set of one or more condensates comprising a second condensate-associated molecule or with a cellular composition that is capable of forming the second set of one or more condensates, and (d) determining the characteristic associated with the second set of one or more condensates, wherein a modulation in the characteristic associated with the first set that is different from a modulation in the characteristic associated with the second set, as compared to a reference, indicates that the compound modulates the characteristic associated with the first set of one or more condensates, thereby obtaining the compound that modulates a characteristic associated with the first set of one or more condensates. In some embodiments, the first and second condensate-associated molecules are the same. In some embodiments, the first and second condensate-associated molecules are the different. In some embodiments, the first set of one or more condensates are stress granules and the second set of one or more condensates are paraspeckles.

In some aspects, provided herein are methods of identifying a compound that modulates a characteristic associated with one or more stress granules, the methods comprising: (a) contacting the compound with a cellular composition comprising one or more stress granules or with a cellular composition that is capable of forming one or more stress granules, and (b) determining the characteristic associated with the one or more stress granules, wherein a modulation in the characteristic, as compared to a reference, indicates that the compound modulates the characteristic associated with the one or more stress granules. In some embodiments, the method comprises determining a single characteristic associated with the one or more stress granules. In some embodiments, the method comprises determining a plurality of characteristics associated with the one or more stress granules.

In some aspects, provided herein are methods of screening (such as high throughput screening) for compounds that modulate a characteristic associated with one or more stress granules, the methods comprising: (a) contacting a plurality of candidate compounds with a cellular composition comprising one or more stress granules or with a cellular composition that is capable of forming one or more stress granules, and (b) determining the characteristic associated with the one or more stress granules, wherein a modulation in the characteristic, as compared to a reference, indicates that the candidate compound modulates the characteristic associated with the one or more stress granules, thereby obtaining the compound that modulates a characteristics of one or more stress granules. In some embodiments, the method comprises determining a plurality of characteristics associated with the one or more stress granules. In some embodiments, the plurality of compounds comprises at least any of 100, 200, 300, 500, 800, 1000, 1500, 3,000, 5,000, 10,000 or more different candidate compounds. In some embodiments, the plurality of candidate compounds are allowed to be in contact with the cellular composition in separate reactions (e.g., separate wells or vessels). In some embodiments, the plurality of candidate compounds are allowed to be in contact with the cellular compositions in separate reactions simultaneously.

In some aspects, provided herein are methods of identifying a compound that modulates a characteristic associated with one or more stress granules, the method comprising: (a) contacting the compound with a cellular composition comprising one or more stress granules and one or more paraspeckles, condensates formed around sites of DNA damage, P bodies, Cajal bodies, and/or PML bodies or with a cellular composition that is capable of forming one or more stress granules and one or more paraspeckles, condensates formed around sites of DNA damage, P bodies, Cajal bodies, and/or PML bodies, (b) determining the characteristic associated with the one or more stress granules, and (c) determining the characteristic associated with the one or more paraspeckles, condensates formed around sites of DNA damage, P bodies, Cajal bodies, and/or PML bodies, wherein a modulation in the characteristic associated with the one or more stress granules that is different from a modulation in the characteristic associated with the one or more paraspeckles, condensates formed around sites of DNA damage, P bodies, Cajal bodies, and/or PML bodies, as compared to a reference, indicates that the compound modulates the characteristic associated with the one or more stress granules.

In some aspects, provided herein are methods of identifying a compound that modulates a characteristic associated with one or more stress granules, the methods comprising: (a) contacting the compound with a cellular composition comprising the one or more stress granules or with a cellular composition that is capable of forming the one or more stress granules, (b) determining the characteristic associated with the one or more stress granules, (c) contacting the compound with a cellular composition comprising one or more paraspeckles, condensates formed around sites of DNA damage, P bodies, Cajal bodies, and/or PML bodies or with a cellular composition that is capable of forming one or more paraspeckles, condensates formed around sites of DNA damage, P bodies, Cajal bodies, and/or PML bodies, and (d) determining the characteristic associated with the one or more paraspeckles, condensates formed around sites of DNA damage, P bodies, Cajal bodies, and/or PML bodies, wherein a modulation in the characteristic associated with the one or more stress granules that is different from a modulation in the characteristic associated with the one or more paraspeckles, condensates formed around sites of DNA damage, P bodies, Cajal bodies, and/or PML bodies, as compared to a reference, indicates that the compound modulates the characteristic associated with the one or more stress granules.

In some aspects, provided herein are methods of screening (such as high throughput screening) for compounds that modulate a characteristic associated with one or more paraspeckles, condensates formed around sites of DNA damage, P bodies, Cajal bodies, and/or PML bodies, the methods comprising: (a) contacting a plurality of candidate compounds with a cellular composition comprising the one or more stress granules and one or more paraspeckles, condensates formed around sites of DNA damage, P bodies, Cajal bodies, and/or PML bodies or with a cellular composition that is capable of forming the one or more stress granules and one or more paraspeckles, condensates formed around sites of DNA damage, P bodies, Cajal bodies, and/or PML bodies, (b) determining the characteristic associated with the one or more stress granules, and (c) determining the characteristic associated with the one or more paraspeckles, condensates formed around sites of DNA damage, P bodies, Cajal bodies, and/or PML bodies, wherein a modulation in the characteristic associated with the one or more stress granules that is different from a modulation in the characteristic associated with the one or more paraspeckles, condensates formed around sites of DNA damage, P bodies, Cajal bodies, and/or PML bodies, as compared to a reference, indicates that the compound modulates the characteristic associated with the one or more stress granules, thereby obtaining the compound that modulates a characteristic associated with the one or more stress granules.

In some aspects, provided herein are methods of screening (such as high throughput screening) for compounds that modulate a characteristic associated one or more stress granules, the methods comprising: (a) contacting a plurality of candidate compounds with a cellular composition comprising the one or more stress granules or with a cellular composition that is capable of forming the one or more stress granules, (b) determining the characteristic associated with the one or more stress granules, (c) contacting a plurality of candidate compounds with a cellular composition comprising one or more paraspeckles, condensates formed around sites of DNA damage, P bodies, Cajal bodies, and/or PML bodies or with a cellular composition that is capable of forming the one or more paraspeckles, condensates formed around sites of DNA damage, P bodies, Cajal bodies, and/or PML bodies, and (d) determining the characteristic associated with the one or more paraspeckles, condensates formed around sites of DNA damage, P bodies, Cajal bodies, and/or PML bodies, wherein a modulation in the characteristic associated with the one or more stress granules that is different than a modulation in the characteristic associated with the one or more paraspeckles, condensates formed around sites of DNA damage, P bodies, Cajal bodies, and/or PML bodies, as compared to a reference, indicates that the compound modulates the characteristic associated with the one or more stress granules, thereby obtaining the compound that modulates a characteristic associated with the one or more stress granules.

In some embodiments, the methods further comprise repeating the steps of the method for a plurality of compounds. For example, in some embodiments, the methods comprise repeating the steps of the method for at least about any of 2, 3, 4, 5, 10, 15, 20, 25, 40, 50, 75, 100, 250, 500, 1,000, 10,000, 100,000 or more compounds. In some embodiments, the method further comprises repeating the steps of the method with a plurality of concentrations of the compound.

In some embodiments, the methods described herein comprise contacting the compound with a cellular composition comprising one or more condensates or a cellular composition capable of forming one or more condensates. One of ordinary skill in the art will readily recognize that cellular processes, including the state of a condensate and components thereof, are dynamic. The methods described herein thus encompass contacting a composition, such as a cellular composition, with a compound at any point in the life cycle of the one or more condensates. For example, the methods encompass contacting a cellular composition with a compound when the condensate-associated molecule is in any location of the cell, in any quantity, or has any post-translation modification status, such as the presence, absence, or level of a phosphorylated residue. In some aspects, the methods may also encompass, e.g., contacting a cell with a compound when the one or more condensates are in any location of the cell, are present in any quantity, including being absent, are undergoing a morphological change, such as a change in size or liquidity, or are changing in composition.

In some embodiments, the cellular composition comprises one or more condensates prior to being brought into contact with the compound. In some embodiments, the method further comprises subjecting the cellular composition to a condensate-forming condition prior to contacting the compound with a cellular composition comprising one or more condensates or with a cellular composition that is capable of forming one or more condensates. In some embodiments, the cellular composition does not comprise one or more condensates prior to being brought into contact with the compound, and the method comprises subjecting the cellular composition to a condensate-forming condition to form the one or more condensates. In some embodiments, the cellular composition does not comprise one or more condensates prior to being brought into contact with the compound, and the method comprises subjecting the cellular composition to a condensate-forming condition to form the one or more condensates after the cellular composition is contacted with the compound. In some embodiments, the cellular composition does not comprise one or more condensates prior to being brought into contact with the compound, and forms one or more condensates simultaneously with contact with the compound. In some embodiments, the condensates form simultaneously and after adding the compound. In some embodiments, the cellular composition is subject to a condensate-forming condition prior to determining the characteristic associated with the one or more condensates. In some embodiments, the cellular composition comprises one or more condensates, and additional condensates of the one or more condensates form simultaneously with contacting the cellular composition with the compound. In some embodiments, the cellular composition comprises one or more condensates, and additional condensates of the one or more condensates form after contacting the cellular composition with the compound. In some embodiments, the cellular composition comprises one or more condensates, and additional condensates of the one or more condensates form simultaneously with and after contacting the cellular composition with the compound.

Accordingly, the methods described herein include contacting a cellular composition with a compound, wherein (i) the cellular composition comprises the one or more target condensates; and/or (ii) the one or more target condensates form simultaneously with and/or after contacting the cellular composition with the compound. In some embodiments, the methods described herein include contacting a cellular composition with a compound, wherein the cellular composition (i) comprises the one or more target condensates; and/or (ii) is capable of forming one or more condensates, wherein the one or more condensates form simultaneously and/or after contacting the cellular composition with the compound. In some embodiments, the methods described herein include contacting the compound with a cellular composition comprising one or more condensates or a cellular composition capable of forming one or more condensates.

Condensate-forming conditions can comprise addition of a condensate-inducing agent. In some embodiments, the method comprises subjecting the cellular composition to any one or more of: (i) an oxidative stressor; (ii) a mitochondrial electron transport chain inhibitor; (iii) a heat stressor; (iv) an osmotic stressor; (v) a hyperosmotic stressor; and (vi) glycolysis inhibition. In some embodiments, the oxidative stressor is arsenate. In some embodiments, the mitochondrial electron transport chain inhibitor is rotenone. In some embodiments, the osmotic stressor is sorbitol. In some embodiments, the glycolysis inhibition is 6-deoxyglucose in the absence of glucose. In some embodiments, the heat stressor is subjecting the cellular composition to a temperature of about 40-45° C., such as about 42° C.

In some embodiments, the reference is an experimental control. In some embodiments, the condensate is a first condensate and the reference is a second condensate. In some embodiments, the second condensate is a condensate that does not comprise the condensate-associated molecule. In some embodiments, the second condensate is a condensate that comprises the condensate-associated molecule. In some embodiments, the first condensate and the second condensate are located in different portions of the cellular composition. In some embodiments, the first condensate and the second condensate are located in different portions of a cell. In some embodiments, the first condensate and the second condensate are located in different cellular compositions. In some embodiments, the cellular composition is a first composition and the reference is a second cellular composition. In some embodiments, the reference is a cellular composition that does not contact the compound. In some embodiments, the reference is a cellular composition that was not treated with a condensate-forming condition. In some embodiments, the reference is a cellular composition that was treated with a reference compound.

In some embodiments, the reference is prepared in a manner such that a meaningful result can be assessed for the compound. For example, in some embodiments, the reference is a cellular composition, wherein the cellular composition is prepared in a similar manner as the cellular composition contacted with the compound, except the reference cellular composition is not subjected to the tested compound or the same step of contacting with the compound. In some embodiments, the reference is a cellular composition contacted with a reference compound, such as a positive or negative control compound.

Characteristics Associated with Condensates

In some embodiments, determining the characteristic associated with the one or more condensates is based on any one or more of the following: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate; and (xiii) aggregation of the condensate-associated molecule. In some embodiments, the method comprises determining a first characteristic associated with the one or more condensates and a second characteristic associated with the one or more condensates. In some embodiments, the method comprises determining a third, fourth, fifth, sixth, seventh, eighth, ninth, tenth, eleventh, twelfth, or thirteenth characteristic associated with the one or more condensates. Exemplary techniques that can be used to determine characteristics are disclosed in the Examples.

In some embodiments, the method comprises determining a first characteristic associated with the one or more condensates and a second characteristic associated with the one or more condensates. In some embodiments, the first characteristic is (i) number of condensates comprising and/or not comprising the condensate-associated molecule and the second characteristic is any one (or more, such as 2, 3, 4, 5, 6, 7, 8, 9, 10, 11, or 12) of (ii) size of the one or more condensates, (iii) location of the one or more condensates, (iv) distribution of one or more condensates, (v) surface area of the one or more condensates, (vi) composition of the one or more condensates, (vii) liquidity of the one or more condensates, (viii) solidification of the one or more condensates, (ix) dissolution of the one or more condensates, (x) presence and/or amount of fiber formation, (xi) location of the condensate-associated molecule, (xii) partitioning of the condensate-associated molecule into the condensate, and (xiii) aggregation of the condensate-associated molecule. In some embodiments, the first characteristic is (i) number of condensates comprising and/or not comprising the condensate-associated molecule and the second characteristic is (ii) size of the one or more condensates. In some embodiments, the first characteristic is (i) number of condensates comprising and/or not comprising the condensate-associated molecule and the second characteristic is (iii) location of the one or more condensates. In some embodiments, the first characteristic is (i) number of condensates comprising and/or not comprising the condensate-associated molecule and the second characteristic is (iv) distribution of one or more condensates. In some embodiments, the first characteristic is (i) number of condensates comprising and/or not comprising the condensate-associated molecule and the second characteristic is (v) surface area of the one or more condensates. In some embodiments, the first characteristic is (i) number of condensates comprising and/or not comprising the condensate-associated molecule and the second characteristic is (vi) composition of the one or more condensates. In some embodiments, the first characteristic is (i) number of condensates comprising and/or not comprising the condensate-associated molecule and the second characteristic is (vii) liquidity of the one or more condensates. In some embodiments, the first characteristic is (i) number of condensates comprising and/or not comprising the condensate-associated molecule and the second characteristic is (viii) solidification of the one or more condensates. In some embodiments, the first characteristic is (i) number of condensates comprising and/or not comprising the condensate-associated molecule and the second characteristic is (ix) dissolution of the one or more condensates. In some embodiments, the first characteristic is (i) number of condensates comprising and/or not comprising the condensate-associated molecule and the second characteristic is (x) presence and/or amount of fiber formation. In some embodiments, the first characteristic is (i) number of condensates comprising and/or not comprising the condensate-associated molecule and the second characteristic is (xi) location of the condensate-associated molecule. In some embodiments, the first characteristic is (i) number of condensates comprising and/or not comprising the condensate-associated molecule and the second characteristic is (xii) partitioning of the condensate-associated molecule into the condensate. In some embodiments, the first characteristic is (i) number of condensates comprising and/or not comprising the condensate-associated molecule and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (ii) size of the one or more condensates and the second characteristic is any one (or more, such as 2, 3, 4, 5, 6, 7, 8, 9, 10, or 11) of (iii) location of the one or more condensates, (iv) distribution of one or more condensates, (v) surface area of the one or more condensates, (vi) composition of the one or more condensates, (vii) liquidity of the one or more condensates, (viii) solidification of the one or more condensates, (ix) dissolution of the one or more condensates, (x) presence and/or amount of fiber formation, (xi) location of the condensate-associated molecule, (xii) partitioning of the condensate-associated molecule into the condensate, and (xiii) aggregation of the condensate-associated molecule. In some embodiments, the first characteristic is (ii) size of the one or more condensates and the second characteristic is (iii) location of the one or more condensates. In some embodiments, the first characteristic is (ii) size of the one or more condensates and the second characteristic is (iv) distribution of one or more condensates. In some embodiments, the first characteristic is (ii) size of the one or more condensates and the second characteristic is (v) surface area of the one or more condensates. In some embodiments, the first characteristic is (ii) size of the one or more condensates and the second characteristic is (vi) composition of the one or more condensates. In some embodiments, the first characteristic is (ii) size of the one or more condensates and the second characteristic is (vii) liquidity of the one or more condensates. In some embodiments, the first characteristic is (ii) size of the one or more condensates and the second characteristic is (viii) solidification of the one or more condensates. In some embodiments, the first characteristic is (ii) size of the one or more condensates and the second characteristic is (ix) dissolution of the one or more condensates. In some embodiments, the first characteristic is (ii) size of the one or more condensates and the second characteristic is (x) presence and/or amount of fiber formation. In some embodiments, the first characteristic is (ii) size of the one or more condensates and the second characteristic is (xi) location of the condensate-associated molecule. In some embodiments, the first characteristic is (ii) size of the one or more condensates and the second characteristic is (xii) partitioning of the condensate-associated molecule into the condensate. In some embodiments, the first characteristic is (ii) size of the one or more condensates and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (iii) location of the one or more condensates and the second characteristic is any one (or more, such as 2, 3, 4, 5, 6, 7, 8, 9, or 10) of (iv) distribution of one or more condensates, (v) surface area of the one or more condensates, (vi) composition of the one or more condensates, (vii) liquidity of the one or more condensates, (viii) solidification of the one or more condensates, (ix) dissolution of the one or more condensates, (x) presence and/or amount of fiber formation, (xi) location of the condensate-associated molecule, (xii) partitioning of the condensate-associated molecule into the condensate, and (xiii) aggregation of the condensate-associated molecule. In some embodiments, the first characteristic is (iii) location of the one or more condensates and the second characteristic is (iv) distribution of one or more condensates. In some embodiments, the first characteristic is (iii) location of the one or more condensates and the second characteristic is (v) surface area of the one or more condensates. In some embodiments, the first characteristic is (iii) location of the one or more condensates and the second characteristic is (vi) composition of the one or more condensates. In some embodiments, the first characteristic is (iii) location of the one or more condensates and the second characteristic is (vii) liquidity of the one or more condensates. In some embodiments, the first characteristic is (iii) location of the one or more condensates and the second characteristic is (viii) solidification of the one or more condensates. In some embodiments, the first characteristic is (iii) location of the one or more condensates and the second characteristic is (ix) dissolution of the one or more condensates. In some embodiments, the first characteristic is (iii) location of the one or more condensates and the second characteristic is (x) presence and/or amount of fiber formation. In some embodiments, the first characteristic is (iii) location of the one or more condensates and the second characteristic is (xi) location of the condensate-associated molecule. In some embodiments, the first characteristic is (iii) location of the one or more condensates and the second characteristic is (xii) partitioning of the condensate-associated molecule into the condensate. In some embodiments, the first characteristic is (iii) location of the one or more condensates and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (iv) distribution of one or more condensates and the second characteristic is any one (or more, such as 2, 3, 4, 5, 6, 7, 8, or 9) of (v) surface area of the one or more condensates, (vi) composition of the one or more condensates, (vii) liquidity of the one or more condensates, (viii) solidification of the one or more condensates, (ix) dissolution of the one or more condensates, (x) presence and/or amount of fiber formation, (xi) location of the condensate-associated molecule, (xii) partitioning of the condensate-associated molecule into the condensate, and (xiii) aggregation of the condensate-associated molecule. In some embodiments, the first characteristic is (iv) distribution of one or more condensates and the second characteristic is (v) surface area of the one or more condensates. In some embodiments, the first characteristic is (iv) distribution of one or more condensates and the second characteristic is (vi) composition of the one or more condensates. In some embodiments, the first characteristic is (iv) distribution of one or more condensates and the second characteristic is (vii) liquidity of the one or more condensates. In some embodiments, the first characteristic is (iv) distribution of one or more condensates and the second characteristic is (viii) solidification of the one or more condensates. In some embodiments, the first characteristic is (iv) distribution of one or more condensates and the second characteristic is (ix) dissolution of the one or more condensates. In some embodiments, the first characteristic is (iv) distribution of one or more condensates and the second characteristic is (x) presence and/or amount of fiber formation. In some embodiments, the first characteristic is (iv) distribution of one or more condensates and the second characteristic is (xi) location of the condensate-associated molecule. In some embodiments, the first characteristic is (iv) distribution of one or more condensates and the second characteristic is (xii) partitioning of the condensate-associated molecule into the condensate. In some embodiments, the first characteristic is (iv) distribution of one or more condensates and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (v) surface area of the one or more condensates and the second characteristic is any one (or more, such as 2, 3, 4, 5, 6, 7, or 8) of (vi) composition of the one or more condensates, (vii) liquidity of the one or more condensates, (viii) solidification of the one or more condensates, (ix) dissolution of the one or more condensates, (x) presence and/or amount of fiber formation, (xi) location of the condensate-associated molecule, (xii) partitioning of the condensate-associated molecule into the condensate, and (xiii) aggregation of the condensate-associated molecule. In some embodiments, the first characteristic is (v) surface area of the one or more condensates and the second characteristic is (vi) composition of the one or more condensates. In some embodiments, the first characteristic is (v) surface area of the one or more condensates and the second characteristic is (vii) liquidity of the one or more condensates. In some embodiments, the first characteristic is (v) surface area of the one or more condensates and the second characteristic is (viii) solidification of the one or more condensates. In some embodiments, the first characteristic is (v) surface area of the one or more condensates and the second characteristic is (ix) dissolution of the one or more condensates. In some embodiments, the first characteristic is (v) surface area of the one or more condensates and the second characteristic is (x) presence and/or amount of fiber formation. In some embodiments, the first characteristic is (v) surface area of the one or more condensates and the second characteristic is (xi) location of the condensate-associated molecule. In some embodiments, the first characteristic is (v) surface area of the one or more condensates and the second characteristic is (xii) partitioning of the condensate-associated molecule into the condensate. In some embodiments, the first characteristic is (v) surface area of the one or more condensates and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (vi) composition of the one or more condensates and the second characteristic is any one (or more, such as 2, 3, 4, 5, 6, or 7) of (vii) liquidity of the one or more condensates, (viii) solidification of the one or more condensates, (ix) dissolution of the one or more condensates, (x) presence and/or amount of fiber formation, (xi) location of the condensate-associated molecule, (xii) partitioning of the condensate-associated molecule into the condensate, and (xiii) aggregation of the condensate-associated molecule. In some embodiments, the first characteristic is (vi) composition of the one or more condensates and the second characteristic is (vii) liquidity of the one or more condensates. In some embodiments, the first characteristic is (vi) composition of the one or more condensates and the second characteristic is (viii) solidification of the one or more condensates. In some embodiments, the first characteristic is (vi)

composition of the one or more condensates and the second characteristic is (ix) dissolution of the one or more condensates. In some embodiments, the first characteristic is (vi) composition of the one or more condensates and the second characteristic is (x) presence and/or amount of fiber formation. In some embodiments, the first characteristic is (vi) composition of the one or more condensates and the second characteristic is (xi) location of the condensate-associated molecule. In some embodiments, the first characteristic is (vi) composition of the one or more condensates and the second characteristic is (xii) partitioning of the condensate-associated molecule into the condensate. In some embodiments, the first characteristic is (vi) composition of the one or more condensates and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (vii) liquidity of the one or more condensates and the second characteristic is any one (or more, such as 2, 3, 4, 5, or 6) of (viii) solidification of the one or more condensates, (ix) dissolution of the one or more condensates, (x) presence and/or amount of fiber formation, (xi) location of the condensate-associated molecule, (xii) partitioning of the condensate-associated molecule into the condensate, and (xiii) aggregation of the condensate-associated molecule. In some embodiments, the first characteristic is (vii) liquidity of the one or more condensates and the second characteristic is (viii) solidification of the one or more condensates. In some embodiments, the first characteristic is (vii) liquidity of the one or more condensates and the second characteristic is (ix) dissolution of the one or more condensates. In some embodiments, the first characteristic is (vii) liquidity of the one or more condensates and the second characteristic is (x) presence and/or amount of fiber formation. In some embodiments, the first characteristic is (vii) liquidity of the one or more condensates and the second characteristic is (xi) location of the condensate-associated molecule. In some embodiments, the first characteristic is (vii) liquidity of the one or more condensates and the second characteristic is (xii) partitioning of the condensate-associated molecule into the condensate. In some embodiments, the first characteristic is (vii) liquidity of the one or more condensates and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (viii) solidification of the one or more condensates and the second characteristic is any one (or more, such as 2, 3, 4, or 5) of (ix) dissolution of the one or more condensates, (x) presence and/or amount of fiber formation, (xi) location of the condensate-associated molecule, (xii) partitioning of the condensate-associated molecule into the condensate, and (xiii) aggregation of the condensate-associated molecule. In some embodiments, the first characteristic is (viii) solidification of the one or more condensates and the second characteristic is (ix) dissolution of the one or more condensates. In some embodiments, the first characteristic is (viii) solidification of the one or more condensates and the second characteristic is (x) presence and/or amount of fiber formation. In some embodiments, the first characteristic is (viii) solidification of the one or more condensates and the second characteristic is (xi) location of the condensate-associated molecule. In some embodiments, the first characteristic is (viii) solidification of the one or more condensates and the second characteristic is (xii) partitioning of the condensate-associated molecule into the condensate. In some embodiments, the first characteristic is (viii) solidification of the one or more condensates and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (ix) dissolution of the one or more condensates and the second characteristic is any one (or more, such as 2, 3, or 4) of (x) presence and/or amount of fiber formation, (xi) location of the condensate-associated molecule, (xii) partitioning of the condensate-associated molecule into the condensate, and (xiii) aggregation of the condensate-associated molecule. In some embodiments, the first characteristic is (ix) dissolution of the one or more condensates and the second characteristic is (x) presence and/or amount of fiber formation. In some embodiments, the first characteristic is (ix) dissolution of the one or more condensates and the second characteristic is (xi) location of the condensate-associated molecule. In some embodiments, the first characteristic is (ix) dissolution of the one or more condensates and the second characteristic is (xii) partitioning of the condensate-associated molecule into the condensate. In some embodiments, the first characteristic is (ix) dissolution of the one or more condensates and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (x) presence and/or amount of fiber formation and the second characteristic is any one (or more, such as 2 or 3) of (xi) location of the condensate-associated molecule, (xii) partitioning of the condensate-associated molecule into the condensate, and (xiii) aggregation of the condensate-associated molecule. In some embodiments, the first characteristic is (x) presence and/or amount of fiber formation and the second characteristic is (xi) location of the condensate-associated molecule. In some embodiments, the first characteristic is (x) presence and/or amount of fiber formation and the second characteristic is (xii) partitioning of the condensate-associated molecule into the condensate. In some embodiments, the first characteristic is (x) presence and/or amount of fiber formation and the second characteristic is (xiii) aggregation of the condensate-associated molecule.

In some embodiments, the method comprises determining a first characteristic associated with the one or more condensates and a second characteristic associated with the one or more condensates. In some embodiments, the first characteristic is (xi) location of the condensate-associated molecule and the second characteristic is (xii) partitioning of the condensate-associated molecule into the condensate and/or (xiii) aggregation of the condensate-associated molecule. In some embodiments, the first characteristic is (xi) location of the condensate-associated molecule and the second characteristic is (xii) partitioning of the condensate-associated molecule into the condensate.

In some embodiments, the method comprises determining a first characteristic associated with the one or more condensates and a second characteristic associated with the one or more condensates. In some embodiments, the first characteristic is (xii) partitioning of the condensate-associated molecule into the condensate and the second characteristic is (xiii) aggregation of the condensate-associated molecule.

In some embodiments, the compound modulates one or more (such as two, three, four, five, six, seven, eight, nine, ten, eleven, twelve, or all) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate; and (xiii) aggregation of the condensate-associated molecule.

In some embodiments, the compound modulates (i) number of condensates comprising and/or not comprising the condensate-associated molecule. In some embodiments, the compound modulates (ii) size of the one or more condensates. In some embodiments, the compound modulates (iii) location of the one or more condensates. In some embodiments, the compound modulates (iv) distribution of one or more condensates. In some embodiments, the compound modulates (v) surface area of the one or more condensates. In some embodiments, the compound modulates (vi) composition of the one or more condensates. In some embodiments, the compound modulates (vii) liquidity of the one or more condensates. In some embodiments, the compound modulates (viii) solidification of the one or more condensates. In some embodiments, the compound modulates (ix) dissolution of the one or more condensates. In some embodiments, the compound modulates (x) presence and/or amount of fiber formation. In some embodiments, the compound modulates (xi) location of the condensate-associated molecule. In some embodiments, the compound modulates (xii) partitioning of the condensate-associated molecule into the condensate. In some embodiments, the compound modulates (xiii) aggregation of the condensate-associated molecule.

In some embodiments, the compound does not modulate one or more (such as two, three, four, five, six, seven, eight, nine, ten, eleven, twelve, or all) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate; and (xiii) aggregation of the condensate-associated molecule.

In some embodiments, the compound does not modulate (i) number of condensates comprising and/or not comprising the condensate-associated molecule. In some embodiments, the compound does not modulate (ii) size of the one or more condensates. In some embodiments, the compound does not modulate (iii) location of the one or more condensates. In some embodiments, the compound does not modulate (iv) distribution of one or more condensates. In some embodiments, the compound does not modulate (v) surface area of the one or more condensates. In some embodiments, the compound does not modulate (vi) composition of the one or more condensates. In some embodiments, the compound does not modulate (vii) liquidity of the one or more condensates. In some embodiments, the compound does not modulate (viii) solidification of the one or more condensates. In some embodiments, the compound does not modulate (ix) dissolution of the one or more condensates. In some embodiments, the compound does not modulate (x) presence and/or amount of fiber formation. In some embodiments, the compound does not modulate (xi) location of the condensate-associated molecule. In some embodiments, the compound does not modulate (xii) partitioning of the condensate-associated molecule into the condensate. In some embodiments, the compound does not modulate (xiii) aggregation of the condensate-associated molecule.

In some embodiments, the compound modulates one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate; and (xiii) aggregation of the condensate-associated molecule, and does not modulate the other of the thirteen characteristics.

In some embodiments, the compound modulates a first characteristic associated with one or more condensates and does not modulate a second characteristic associated the one or more condensates, wherein the first characteristic is different from the second characteristic, and wherein the characteristics are selected from the group consisting of: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate; and (xiii) aggregation of the condensate-associated molecule, and does not modulate the other of the thirteen characteristics.

In some embodiments, the compound modulates one or more of: one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensates in a first portion of the cellular composition, such as a first portion of a cell, and does not modulate one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate in a second portion of the cellular composition, such as a second portion of a cell.

In some embodiments, the compound modulates one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate in the cytoplasm, and does not modulate one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate in the nucleus.

In some embodiments, the compound modulates one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate for a first set of one or more condensates and does not modulate one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate for a second set of one or more condensates.

In some embodiments, the compound modulates one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate in one or more stress granules and does not modulate one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate for one or more of nuclear paraspeckles, condensates formed around sites of DNA damage, P bodies, Cajal bodies, and PML bodies.

In some embodiments, the method is a method of identifying a compound that modulates one or more (such as two, three, four, five, six, seven, eight, nine, ten, eleven, twelve, or all) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate; and (xiii) aggregation of the condensate-associated molecule.

In some embodiments, the method is a method of identifying a compound that modulates (i) number of condensates comprising and/or not comprising the condensate-associated molecule. In some embodiments, the method is a method of identifying a compound that modulates (ii) size of the one or more condensates. In some embodiments, the method is a method of identifying a compound that modulates (iii) location of the one or more condensates. In some embodiments, the method is a method of identifying a compound that modulates (iv) distribution of one or more condensates. In some embodiments, the method is a method of identifying a compound that modulates (v) surface area of the one or more condensates. In some embodiments, the method is a method of identifying a compound that modulates (vi) composition of the one or more condensates. In some embodiments, the method is a method of identifying a compound that modulates (vii) liquidity of the one or more condensates. In some embodiments, the method is a method of identifying a compound that modulates (viii) solidification of the one or more condensates. In some embodiments, the method is a method of identifying a compound that modulates (ix) dissolution of the one or more condensates. In some embodiments, the method is a method of identifying a compound that modulates (x) presence and/or amount of fiber formation. In some embodiments, the method is a method of identifying a compound that modulates (xi) location of the condensate-associated molecule. In some embodiments, the method is a method of identifying a compound that modulates (xii) partitioning of the condensate-associated molecule into the condensate. In some embodiments, the method is a method of identifying a compound that modulates (xiii) aggregation of the condensate-associated molecule.

In some embodiments, the compound does not modulate one or more (such as two, three, four, five, six, seven, eight, nine, ten, eleven, twelve, or all) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate; and (xiii) aggregation of the condensate-associated molecule.

In some embodiments, the compound does not modulate (i) number of condensates comprising and/or not comprising the condensate-associated molecule. In some embodiments, the compound does not modulate (ii) size of the one or more condensates. In some embodiments, the compound does not modulate (iii) location of the one or more condensates. In some embodiments, the compound does not modulate (iv) distribution of one or more condensates. In some embodiments, the compound does not modulate (v) surface area of the one or more condensates. In some embodiments, the compound does not modulate (vi) composition of the one or more condensates. In some embodiments, the compound does not modulate (vii) liquidity of the one or more condensates. In some embodiments, the compound does not modulate (viii) solidification of the one or more condensates. In some embodiments, the compound does not modulate (ix) dissolution of the one or more condensates. In some embodiments, the compound does not modulate (x) presence and/or amount of fiber formation. In some embodiments, the compound does not modulate (xi) location of the condensate-associated molecule. In some embodiments, the compound does not modulate (xii) partitioning of the condensate-associated molecule into the condensate. In some embodiments, the compound does not modulate (xiii) aggregation of the condensate-associated molecule.

In some embodiments, the method is a method of identifying a compound that modulates one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate; and (xiii) aggregation of the condensate-associated molecule, and does not modulate the other of the thirteen characteristics.

In some embodiments, the method is a method of identifying a compound that modulates one or more of: one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensates in a first portion of the cellular composition, such as a first portion of a cell, and does not modulate one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate in a second portion of the cellular composition, such as a second portion of a cell.

In some embodiments, the method is a method of identifying a compound that modulates one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate in the cytoplasm, and does not modulate one or more (such as two, three, four, five, six, seven, eight, nine, ten, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate in the nucleus.

In some embodiments, the method is a method of identifying a compound that modulates one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate for a first set of one or more condensates and does not modulate one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate for a second set of one or more condensates.

In some embodiments, the method is a method of identifying a compound that modulates one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate in one or more stress granules and does not modulate one or more (such as two, three, four, five, six, seven, eight, nine, ten, eleven, or twelve) characteristics selected from: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates, (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the condensate for one or more of nuclear paraspeckles, condensates formed around sites of DNA damage, P bodies, Cajal bodies, and PML bodies.

In some embodiments, the determining is performed within about 60 days of the contacting of the compound, such as within about 35 days, about 28 days, about 21 days, about 14 days, about 10 days, about 7 days, about 5 days, about 3 days, about 2 days, about 1 day, about 12 hours about 5 hours, about 2 hours, about 1 hour, about 45 minutes, about 30 minutes, about 15 minutes, about 5 minutes, about 1 minute, or about 30 seconds. In some embodiments, the determining is performed after about 5 seconds of the contacting of the compound, such as, after about 15 seconds, about 30 seconds, about 1 minute, about 5 minutes, about 15 minutes, about 30 minutes, about 45 minutes, about 1 hour, about 2 hours, about 5 hours, about 12 hours, about 1 day, about 2 days, about 3 days, about 5 days, about 7 days, about 10 days, about 14 days, about 21 days, about 28 days, about 35 days, or about 60 days.

In some embodiments, the method comprises determining the characteristic before and after contacting the compound. In some embodiments, the method further comprises comparing the characteristic before and after contacting the compound.

In some embodiments, the method further comprises repeating the determining step of the method. For example, in some embodiments, the methods comprise repeating the determining step of the method at least about any of 2, 3, 4, 5, 10, or more times. In some embodiments, the method comprises performing the determining step for a first portion of the cellular composition and a second portion of the cellular composition, such as a first cell and a second cell in the cellular composition. In some embodiments, the method comprises performing the determining step for a third, fourth, fifth, sixth, or more portion of the cellular composition, such as a third, fourth, fifth, sixth, or more cell in the cellular composition. In some embodiments the method comprises performing the determining step for a first portion of a cell in the cellular composition and a second portion of a cell in the cellular composition, such as in the cytoplasm and the nucleus, or in a first organelle and a second organelle. In some embodiments, the method comprises performing the determining step for a third, fourth, fifth, sixth, or more portion of a cell in the cellular composition.

In some embodiments, the determining step of the method is repeated after an interval of time, such as about 30 seconds, about 1 minute, about 5 minutes, about 15 minutes, about 30 minutes, about 45 minutes, about 1 hour, about 2 hours, about 5 hours, about 12 hours, about 1 day, about 2 days, about 3 days, about 5 days, about 7 days, about 10 days, about 14 days, about 21 days, about 28 days, about 35 days, about 60 days, or more. In some embodiments the determining step is based on the same characteristic when repeated. In some embodiments, the method further comprises comparing the characteristic over time, such as comparing the number of condensates with one day between determinations.

Visualizing condensates may aid in determine a characteristic associated with one or more condensates. Condensates can be visualized by a variety of methods, such as microscopy, including, for example, stereoscopic microscopy, brightfield microscopy, polarizing microscopy, phase contrast microscopy, differential interference contrast microscopy, fluorescence microscopy, total internal reflection fluorescence microscopy, confocal microscopy, or multiphoton excitation microscopy. Analysis, such as counting the number of condensates or measuring the size of a condensate, can be determined by a variety of methods including manually or in an automated way, and can be done for example, from images or directly from a microscope. For ease, the condensate and/or the condensate-associated molecule may be labeled in some embodiments, such as labeled with a fluorophore. In some embodiments, the condensate-associated molecule comprises a fluorescent label, such as a fluorescent protein (e.g., GFP, RFP, YFP, etc.). In some embodiments, the method comprises contacting at least a portion of the cellular composition with a label. In some embodiments, the label is a labeled binding molecule, such as an antibody (such as a labeled secondary antibody) or biotin-binding protein. In some embodiments, the label is a stain, such as a stain specific to an organelle.

In some embodiments, the method further comprises imaging at least a portion of the cellular composition, such as a field of view. In some embodiments, the method further comprises contacting at least a portion of the cellular composition with a fixative. In some embodiments, the method further comprises contacting at least a portion of the cellular composition with a stain. In some embodiments, the method further comprises contacting at least a portion of the cellular composition with a DNA-damaging condition. In some embodiments, the DNA-damaging condition is laser irradiation.

The characteristic can be determined for a portion or all of the cellular composition. Accordingly, in some embodiments, the method comprises determining the characteristic in a portion of the cellular composition. In some embodiments, the method comprises determining the characteristic in the entire cellular composition. In some embodiments, the method comprises determining the characteristic in one or more cells in the cellular composition. In some embodiments, the method comprises determining the characteristic in a single cell in the cellular composition.

The characteristic can also be determined for a portion or all of a cell in the cellular composition. Accordingly, in some embodiments, the method comprises determining the characteristic in a portion of one or more cells in the cellular composition. In some embodiments, the method comprises determining characteristic in a portion of a single cell in the cellular composition. In some embodiments, the method comprises determining the characteristic in a cytoplasm in the cellular composition. In some embodiments, the method comprises determining the characteristic in a nucleus in the cellular composition. In some embodiments, the method comprises determining the characteristic in an organelle.

Number of Condensates

In some embodiments, the characteristic associated with the one or more condensates is based on the number of condensates comprising and/or not comprising the condensate-associated molecule. In some embodiments, the characteristic associated with the one or more condensates is based on the number of condensates comprising the condensate-associated molecule. In some embodiments, the characteristic associated with the one or more condensates is based on the number of condensates not comprising the condensate-associated molecule. Accordingly, in some embodiments, provided herein are methods of identifying a compound that modulates a characteristic associated with one or more condensates comprising a condensate-associated molecule, the method comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the number of condensates comprising and/or not comprising the condensate-associated molecule. In some embodiments, provided herein are methods of identifying a compound that modulates the number of condensates comprising and/or not comprising the condensate-associated molecule, the method comprising: (a) contacting the compound with a cellular composition comprising one or more condensates or with a cellular composition that is capable of forming one or more condensates, and (b) determining the number of condensates comprising and/or not comprising the condensate-associated molecule, wherein a modulation in the number of condensates, as compared to a reference, indicates that the compound modulates the number of condensates comprising and/or not comprising the condensate-associated molecule.

The number of condensates can be determined for a portion or all of the cellular composition. Accordingly, in some embodiments, the method comprises determining the number of condensates comprising and/or not comprising the condensate-associated molecule in a portion of the cellular composition. In some embodiments, the method comprises determining the number of condensates comprising and/or not comprising the condensate-associated molecule in the entire cellular composition. In some embodiments, the method comprises determining the number of condensates comprising and/or not comprising the condensate-associated molecule in one or more cells in the cellular composition. In some embodiments, the method comprises determining the number of condensates comprising and/or not comprising the condensate-associated molecule in a single cell in the cellular composition.

The number of condensates can also be determined for a portion or all of a cell in the cellular composition. Accordingly, in some embodiments, the method comprises determining the number of condensates comprising and/or not comprising the condensate-associated molecule in a portion of one or more cells in the cellular composition. In some embodiments, the method comprises determining the number of condensates comprising and/or not comprising the condensate-associated molecule in a portion of a single cell in the cellular composition. In some embodiments, the method comprises determining the number of condensates comprising and/or not comprising the condensate-associated molecule in the cytoplasm. In some embodiments, the method comprises determining the number of condensates comprising and/or not comprising the condensate-associated molecule in the nucleus. In some embodiments, the method comprises determining the number of condensates comprising and/or not comprising the condensate-associated molecule in an organelle.

In some embodiments, the method comprises determining the number of condensates comprising the condensate-associated molecule; determining the number of condensates not comprising the condensate-associated molecule; and comparing the number of condensates comprising the condensate-associated molecule and the number of condensate-associated molecule. In some embodiments, the method comprises determining the number of condensates comprising and/or not comprising the condensate-associated molecule in a first portion of the cellular composition, such as any portion of the cellular composition disclosed herein; determining the number of condensates comprising and/or not comprising the condensate-associated molecule in a second portion of the cellular composition, such as any portion of the cellular composition disclosed herein; and comparing the number of condensates comprising and/or not comprising the condensate-associated molecule in the first portion and the number of condensates comprising and/or not comprising the condensate-associated molecule in the second portion. In some embodiments, the method comprises determining the number of condensates comprising the condensate-associated molecule in a cytoplasm in the cellular composition; determining the number of condensates comprising the condensate-associated molecule in a nucleus in the cellular composition; and comparing the number of condensates comprising the condensate-associated molecule in the cytoplasm and the nucleus.

In some embodiments, the number of condensates comprising the condensate-associated molecule increases as compared to the reference. In some embodiments, the number of condensates comprising the condensate-associated molecule decreases as compared to the reference. In some embodiments, the number of condensates not comprising the condensate-associated molecule increases as compared to the reference. In some embodiments, the number of condensates not comprising the condensate-associated molecule decreases as compared to the reference.

In some embodiments, the number of condensates comprising and/or not comprising the condensate-associated molecule in the first portion of the cellular composition decreases compared to the reference, and the number of condensates comprising and/or not comprising the condensate-associated molecule in the second portion of the cell composition does not decrease compared to the reference. In some embodiments, the number of condensates comprising and/or not comprising the condensate-associated molecule in the first portion of the cellular composition increases compared to the reference, and the number of condensates comprising and/or not comprising the condensate-associated molecule in the second portion of the cell composition does not increase compared to the reference. In some embodiments, the first portion of the cellular composition is the cytoplasm and the second portion of the cellular composition is the nucleus, or the first portion of the cellular composition is the nucleus and the second portion of the cellular composition is the cytoplasm. In some embodiments, the number of condensates comprising the condensate-associated molecule in the cytoplasm decreases compared to the reference and the number of condensates comprising the condensate-associated molecule in the nucleus does not decrease compared to the reference. In some embodiments, the number of condensates comprising the condensate-associated molecule in the cytoplasm decreases compared to the reference and the number of condensates comprising the condensate-associated molecule in the nucleus increases compared to the reference.

In some embodiments, the number of condensates comprising and/or not comprising the condensate-associated molecule in the first portion of the cellular composition increases compared to the second portion of the cell composition, or the number of condensates comprising and/or not comprising the condensate-associated molecule in the second portion of the cell composition increases compared to the first portion of the cell composition. In some embodiments, the first portion of the cellular composition is the cytoplasm and the second portion of the cellular composition is the nucleus, or the first portion of the cellular composition is the nucleus and the second portion of the cellular composition is the cytoplasm.

Size of Condensates

In some embodiments, the characteristic associated with the one or more condensates is based on the size of the one or more condensates. Accordingly, in some embodiments, provided herein are methods of identifying a compound that modulates a characteristic associated with one or more condensates comprising a condensate-associated molecule, the methods comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the size of the one or more condensates. In some embodiments, provided herein are methods of identifying a compound that modulates the size of the one or more condensates, the method comprising: (a) contacting the compound with a cellular composition comprising one or more condensates or with a cellular composition that is capable of forming one or more condensates, and (b) determining the size of the one or more condensates, wherein a modulation of the size, as compared to a reference, indicates that the compound modulates the size of the one or more condensates. In some embodiments, the size is the average of two or more condensates.

The size of condensates can be determined for a portion or all of the cellular composition. Accordingly, in some embodiments, the method comprises determining the size of the one or more condensates in a portion of the cellular composition. In some embodiments, the method comprises determining the size of the one or more condensates in the entire cellular composition. In some embodiments, the method comprises determining the size of the one or more condensates in one or more cells in the cellular composition. In some embodiments, the method comprises determining the size of the one or more condensates in a single cell in the cellular composition.

The size of condensates can also be determined for a portion or all of a cell in the cellular composition. Accordingly, in some embodiments, the method comprises determining the size of the one or more condensates in a portion of one or more cells in the cellular composition. In some embodiments, the method comprises determining the size of the one or more condensates in a portion of a single cell in the cellular composition. In some embodiments, the method comprises determining the size of the one or more condensates in the cytoplasm. In some embodiments, the method comprises determining the size of the one or more condensates in the nucleus. In some embodiments, the method comprises determining the size of the one or more condensates in an organelle.

In some embodiments, the size of the one or more condensates increases as compared to the reference. In some embodiments, the size of the one or more condensates decreases as compared to the reference.

In some embodiments, the size of the one or more condensates in the first portion of the cellular composition decreases compared to the reference, and the size of the one or more condensates in the second portion of the cell composition does not decrease compared to the reference. In some embodiments, the size of the one or more condensates in the first portion of the cellular composition increases compared to the reference, and the size of the one or more condensates in the second portion of the cell composition does not increase compared to the reference. In some embodiments, the first portion of the cellular composition is the cytoplasm and the second portion of the cellular composition is the nucleus, or the first portion of the cellular composition is the nucleus and the second portion of the cellular composition is the cytoplasm. In some embodiments, the size of the one or more condensates in the cytoplasm decreases compared to the reference and the size of the one or more condensates in the nucleus does not decrease compared to the reference. In some embodiments, the size of the one or more condensates in the cytoplasm decreases compared to the reference and the size of the one or more condensates in the nucleus increases compared to the reference.

In some embodiments, the size of the one or more condensates in the first portion of the cellular composition increases compared to the second portion of the cell composition, or the size of the one or more condensates in the second portion of the cell composition increases compared to the first portion of the cell composition. In some embodiments, the first portion of the cellular composition is the cytoplasm and the second portion of the cellular composition is the nucleus, or the first portion of the cellular composition is the nucleus and the second portion of the cellular composition is the cytoplasm.

Location of Condensates

In some embodiments, the characteristic associated with the one or more condensates is based on the location of the one or more condensates. Accordingly, in some embodiments, provided herein are methods of identifying a compound that modulates a characteristic associated with one or more condensates comprising a condensate-associated molecule, the methods comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the location of the one or more condensates. In some embodiments, provided herein are methods of identifying a compound that modulates the location of the one or more condensates, the method comprising: (a) contacting the compound with a cellular composition comprising one or more condensates or with a cellular composition that is capable of forming one or more condensates, and (b) determining the location of the one or more condensates, wherein a modulation of the location, as compared to a reference, indicates that the compound modulates the location of the one or more condensates.

The location of condensates can be determined for a portion or all of the cellular composition. Accordingly, in some embodiments, the method comprises determining the location of the one or more condensates in a portion of the cellular composition. In some embodiments, the method comprises determining the location of the one or more condensates in the entire cellular composition. In some embodiments, the method comprises determining the location of the one or more condensates in one or more cells in the cellular composition. In some embodiments, the method comprises determining the location of the one or more condensates in a single cell in the cellular composition.

The location of condensates can also be determined for a portion or all of a cell in the cellular composition. Accordingly, in some embodiments, the method comprises determining the location of the one or more condensates in a portion of one or more cells in the cellular composition. In some embodiments, the method comprises determining the location of the one or more condensates in a portion of a single cell in the cellular composition. In some embodiments, the method comprises determining the location of the one or more condensates in the cytoplasm. In some embodiments, the method comprises determining the location of the one or more condensates in the nucleus. In some embodiments, the method comprises determining the location of the one or more condensates in an organelle.

Distribution of Condensates

In some embodiments, the characteristic associated with the one or more condensates is based on the distribution of one or more condensates, such as the spatial distribution of one or more condensates within a cell. Accordingly, in some embodiments, provided herein are methods of identifying a compound that modulates a characteristic associated with one or more condensates comprising a condensate-associated molecule, the method comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the distribution of one or more condensates. In some embodiments, provided herein are methods of identifying a compound that modulates the distribution of one or more condensates, the method comprising: (a) contacting the compound with a cellular composition comprising one or more condensates or with a cellular composition that is capable of forming one or more condensates, and (b) determining the distribution of one or more condensates, wherein a modulation in the distribution, as compared to a reference, indicates that the compound modulates the distribution of one or more condensates.

In some embodiments, the distribution of one or more condensates is based on the number of condensates comprising a condensate-associated molecule in a cellular location, such as any one or more of the cytosol, the nucleus, an organelle, or any portion thereof. In some embodiments, the distribution of one or more condensates is determined to be modulated by the compound when the number of condensates comprising a condensate-associated molecule in a cellular location, such as the cytosol or nucleus, decreases as compared to the number of condensates comprising the condensate-associated molecule in the cellular location of a reference cellular composition, such as a cellular composition not contacted with the compound or a cellular composition contacted with a control compound. In some embodiments, the distribution of one or more condensates is determined to be modulated by the compound when the number of condensates comprising a condensate-associated molecule in a cellular location, such as the cytosol or nucleus, increases as compared to the number of condensates comprising the condensate-associated molecule in the cellular location of a reference cellular composition, such as a cellular composition not contacted with the compound or a cellular composition contacted with a control compound.

In some embodiments, the distribution of one or more condensates is based on the number of condensates comprising a condensate-associated molecule in one or more portions of a cellular composition, such as one or more fields of view or one or more portions of an image of a cellular composition. In some embodiments, the distribution of one or more condensates is determined to be modulated by the compound when the number of condensates comprising a condensate-associated molecule in one or more portions of a cellular composition, such as a portion of the cytosol or nucleus, decreases as compared to the number of condensates comprising the condensate-associated molecule in one or more portions of a reference cellular composition, such as one or more portions of a cellular composition not contacted with the compound or one or more portion of a cellular composition contacted with a control compound. In some embodiments, the distribution of one or more condensates is determined to be modulated by the compound when the number of condensates comprising a condensate-associated molecule in one or more portions of a cellular composition, such as a portion of the cytosol or nucleus, increases as compared to the number of condensates comprising the condensate-associated molecule in one or more portions of a reference cellular composition, such as one or more portions of a cellular composition not contacted with the compound or one or more portion of a cellular composition contacted with a control compound.

In some embodiments, the distribution of condensates is determined by calculating the ratio (e.g., percentage, part per thousand, etc.) of condensates in a first a portion of the cellular composition and a second portion of the cellular composition. In some embodiments, the method comprises determining the number of condensates comprising the condensate-associated molecule in a first portion of the cellular composition, determining the number of condensates comprising the condensate-associated molecule in a second portion of the cellular composition, and calculating the ratio of the number of condensates comprising the condensate-associated molecule in the first and second portion of the cellular composition. In some embodiments, the first portion of the cellular composition is a first portion of a cell and the second portion of a cell, such as the cytoplasm, nucleus, or an organelle. In some embodiments, the first portion of the cellular composition is the cytoplasm and the second portion is the nucleus. In some embodiments, the ratio increases as compared to the reference, such as a cellular composition not contacted with the compound or a cellular composition contacted with a control compound. In some embodiments, the ratio decreases as compared to the reference. In some embodiments, the ratio of nuclear to cytoplasmic condensates increases as compared to the reference. In some embodiments, the ratio of nuclear to cytoplasmic condensates decreases as compared to the reference. In some embodiments, the distribution of one or more condensates is determined to be modulated by the compound when the ratio of condensates in the first portion of the cellular composition, such as the nucleus, and the second portion of the cellular composition, such as the cytosol, increases as compared to the reference. In some embodiments, the distribution of one or more condensates is determined to be modulated by the compound when the ratio of condensates in the first portion of the cellular composition, such as the nucleus, and the second portion of the cellular composition, such as the cytosol, decreases as compared to the reference.

In some embodiments, the distribution of one or more condensates is determined using an imaging technique.

Surface Area of Condensates

In some embodiments, the characteristic associated with the one or more condensates is based on the surface area of the one or more condensates. Accordingly, in some embodiments, provided herein are methods of identifying a compound that modulates a characteristic associated with one or more condensates comprising a condensate-associated molecule, the methods comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the surface area of the one or more condensates. In some embodiments, provided herein are methods of identifying a compound that modulates the surface area of the one or more condensates, the method comprising: (a) contacting the compound with a cellular composition comprising one or more condensates or with a cellular composition that is capable of forming one or more condensates, and (b) determining the surface area of the one or more condensates, wherein a modulation of the surface area, as compared to a reference, indicates that the compound modulates the surface area of the one or more condensates. In some embodiments, the surface area is the average of two or more condensates.

The surface area of condensates can be determined for a portion or all of the cellular composition. Accordingly, in some embodiments, the method comprises determining the surface area of the one or more condensates in a portion of the cellular composition. In some embodiments, the method comprises determining the surface area of the one or more condensates in the entire cellular composition. In some embodiments, the method comprises determining the surface area of the one or more condensates in one or more cells in the cellular composition. In some embodiments, the method comprises determining the surface area of the one or more condensates in a single cell in the cellular composition.

The surface area of condensates can also be determined for a portion or all of a cell in the cellular composition. Accordingly, in some embodiments, the method comprises determining the surface area of the one or more condensates in a portion of one or more cells in the cellular composition. In some embodiments, the method comprises determining the surface area of the one or more condensates in a portion of a single cell in the cellular composition. In some embodiments, the method comprises determining the surface area of the one or more condensates in the cytoplasm. In some embodiments, the method comprises determining the surface area of the one or more condensates in the nucleus. In some embodiments, the method comprises determining the surface area of the one or more condensates in an organelle.

In some embodiments, the surface area of the one or more condensates increases as compared to the reference. In some embodiments, the surface area of the one or more condensates decreases as compared to the reference.

In some embodiments, the surface area of the one or more condensates in the first portion of the cellular composition decreases compared to the reference, and the surface area of the one or more condensates in the second portion of the cell composition does not decrease compared to the reference. In some embodiments, the surface area of the one or more condensates in the first portion of the cellular composition increases compared to the reference, and the surface area of the one or more condensates in the second portion of the cell composition does not increase compared to the reference. In some embodiments, the first portion of the cellular composition is the cytoplasm and the second portion of the cellular composition is the nucleus, or the first portion of the cellular composition is the nucleus and the second portion of the cellular composition is the cytoplasm. In some embodiments, the surface area of the one or more condensates in the cytoplasm decreases compared to the reference and the surface area of the one or more condensates in the nucleus does not decrease compared to the reference. In some embodiments, the surface area of the one or more condensates in the cytoplasm decreases compared to the reference and the surface area of the one or more condensates in the nucleus increases compared to the reference.

In some embodiments, the surface area of the one or more condensates in the first portion of the cellular composition increases compared to the second portion of the cell composition, or the surface area of the one or more condensates in the second portion of the cell composition increases compared to the first portion of the cell composition. In some embodiments, the first portion of the cellular composition is the cytoplasm and the second portion of the cellular composition is the nucleus, or the first portion of the cellular composition is the nucleus and the second portion of the cellular composition is the cytoplasm.

Composition of Condensates

In some embodiments, the characteristic associated with the one or more condensates is based on the composition of the one or more condensates. Accordingly, in some embodiments, provided herein are methods of identifying a compound that modulates a characteristic associated with one or more condensates comprising a condensate-associated molecule, the methods comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the composition of the one or more condensates. In some embodiments, provided herein are methods of identifying a compound that modulates the composition of the one or more condensates, the method comprising: (a) contacting the compound with a cellular composition comprising one or more condensates or with a cellular composition that is capable of forming one or more condensates, and (b) determining the composition of the one or more condensates, wherein a modulation of the composition, as compared to a reference, indicates that the compound modulates the composition of the one or more condensates.

In some embodiments, the composition of the condensate is determined by detecting the presence of one or more macromolecules comprised in the condensate, measuring the amount of one or more macromolecules comprised in the condensate, calculating the ratio of one macromolecule to a second macromolecule comprised in the condensate, and/or comparing amount of one or more macromolecules comprised in the condensate and the size and/or surface area of the condensate. In some embodiments, the composition of the condensate is determined by detecting the presence of one or more macromolecules comprised in the condensate, such as 1, 2, 3, 4, 5, 6, 7, or more macromolecules. In some embodiments, the composition of the condensate is determined by measuring the amount of one or more macromolecules comprised in the condensate, such as 1, 2, 3, 4, 5, 6, 7, or more macromolecules. In some embodiments, the composition of the condensate is determined by calculating the ratio of one macromolecule to a second macromolecule comprised in the condensate. In some embodiments, the composition of the condensate is determined by comparing amount of one or more macromolecules comprised in the condensate and the size and/or surface area of the condensate, such as 1, 2, 3, 4, 5, 6, 7, or more macromolecules. In some embodiments, the macromolecule is the condensate-associated molecule. In some embodiments, the macromolecule is a polynucleotide or polypeptide. In some embodiments, the macromolecule is a polypeptide. In some embodiments, the macromolecule is a wild-type polypeptide. In some embodiments, the macromolecule is a mutant polypeptide. In some embodiments, the macromolecule is FUS, EWSR1, TIAL1, PABPC1, or G3BP1, or a mutant thereof.

The composition of condensates can be determined for a portion or all of the cellular composition. Accordingly, in some embodiments, the method comprises determining the composition of the one or more condensates in a portion of the cellular composition. In some embodiments, the method comprises determining the composition of the one or more condensates in the entire cellular composition. In some embodiments, the method comprises determining the composition of the one or more condensates in one or more cells in the cellular composition. In some embodiments, the method comprises determining the composition of the one or more condensates in a single cell in the cellular composition.

The composition of condensates can also be determined for a portion or all of a cell in the cellular composition. Accordingly, in some embodiments, the method comprises determining the composition of the one or more condensates in a portion of one or more cells in the cellular composition. In some embodiments, the method comprises determining the composition of the one or more condensates in a portion of a single cell in the cellular composition. In some embodiments, the method comprises determining the composition of the one or more condensates in the cytoplasm. In some embodiments, the method comprises determining the composition of the one or more condensates in the nucleus. In some embodiments, the method comprises determining the composition of the one or more condensates in an organelle.

Liquidity of Condensates

In some embodiments, the characteristic associated with the one or more condensates is based on the liquidity of the one or more condensates. Accordingly, in some embodiments, provided herein are methods of identifying a compound that modulates a characteristic associated with one or more condensates comprising a condensate-associated molecule, the methods comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the liquidity of the one or more condensates. In some embodiments, provided herein are methods of identifying a compound that modulates the liquidity of the one or more condensates, the method comprising: (a) contacting the compound with a cellular composition comprising one or more condensates or with a cellular composition that is capable of forming one or more condensates, and (b) determining the liquidity of the one or more condensates, wherein a modulation in the liquidity, as compared to a reference, indicates that the compound modulates the liquidity of the one or more condensates. In some embodiments, the liquidity is based on a measurement accounting for two or more condensates, e.g., the average or distribution of liquidity of two or more condensates.

The liquidity of condensates can be determined for one or more condensates in a portion or all of the cellular composition. Accordingly, in some embodiments, the method comprises determining the liquidity of the one or more condensates in a portion of the cellular composition, such as one or more fields of view or one or more portions of an image of a cellular composition. In some embodiments, the method comprises determining the liquidity of the one or more condensates in the entire cellular composition. In some embodiments, the method comprises determining the liquidity of the one or more condensates in one or more cells in the cellular composition. In some embodiments, the method comprises determining the liquidity of the one or more condensates in a single cell in the cellular composition. In some embodiments, the method comprises determining the liquidity of the one or more condensates in a portion of one or more cells in the cellular composition. In some embodiments, the method comprises determining the liquidity of the one or more condensates in a portion of a single cell in the cellular composition. In some embodiments, the method comprises determining the liquidity of the one or more condensates in the cytoplasm. In some embodiments, the method comprises determining the liquidity of the one or more condensates in the nucleus. In some embodiments, the method comprises determining the liquidity of the one or more condensates in an organelle.

In some embodiments, the liquidity of one or more condensates is determined to be modulated by the compound when the liquidity of the one or more condensates increases as compared to the reference, including reference condensates. In some embodiments, the liquidity of one or more condensates is determined to be modulated by the compound when the liquidity of the one or more condensates decreases as compared to the reference, including reference condensates. In some embodiments, the liquidity of the one or more condensates in the first portion of the cellular composition decreases compared to the reference, and the liquidity of the one or more condensates in the second portion of the cell composition does not decrease compared to the reference. In some embodiments, the liquidity of the one or more condensates in the first portion of the cellular composition increases compared to the reference, and the liquidity of the one or more condensates in the second portion of the cell composition does not increase compared to the reference. In some embodiments, the first portion of the cellular composition is the cytoplasm and the second portion of the cellular composition is the nucleus, or the first portion of the cellular composition is the nucleus and the second portion of the cellular composition is the cytoplasm. In some embodiments, the liquidity of the one or more condensates in the cytoplasm decreases compared to the reference and the liquidity of the one or more condensates in the nucleus does not decrease compared to the reference. In some embodiments, the liquidity of the one or more condensates in the cytoplasm decreases compared to the reference and the liquidity of the one or more condensates in the nucleus increases compared to the reference.

In some embodiments, the liquidity of the one or more condensates in the first portion of the cellular composition increases compared to the second portion of the cell composition, or the liquidity of the one or more condensates in the second portion of the cell composition increases compared to the first portion of the cell composition. In some embodiments, the first portion of the cellular composition is the cytoplasm and the second portion of the cellular composition is the nucleus, or the first portion of the cellular composition is the nucleus and the second portion of the cellular composition is the cytoplasm.

In some embodiments, the liquidity of the one or more condensates is assessed via one or more of the following droplet size, surface tension, a phase diagram, equilibrium state, droplet coarsening, and hardening.

In some embodiments, the liquidity of one or more condensates is determined using an imaging technique.

Solidification of Condensates

In some embodiments, the characteristic associated with the one or more condensates is based on the solidification of the one or more condensates. Accordingly, in some embodiments, provided herein are methods of identifying a compound that modulates a characteristic associated with one or more condensates comprising a condensate-associated molecule, the methods comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the solidification of the one or more condensates. In some embodiments, provided herein are methods of identifying a compound that modulates the solidification of the one or more condensates, the method comprising: (a) contacting the compound with a cellular composition comprising one or more condensates or with a cellular composition that is capable of forming one or more condensates, and (b) determining the solidification of the one or more condensates, wherein a modulation in the solidification, as compared to a reference, indicates that the compound modulates the solidification of the one or more condensates. In some embodiments, the solidification is based on a measurement accounting for two or more condensates, e.g., the average or distribution of solidification of two or more condensates.

The solidification of condensates can be determined for one or more condensates, or a product thereof, in a portion or all of the cellular composition. Accordingly, in some embodiments, the method comprises determining the solidification of the one or more condensates in a portion of the cellular composition, such as one or more fields of view or one or more portions of an image of a cellular composition. In some embodiments, the method comprises determining the solidification of the one or more condensates in the entire cellular composition. In some embodiments, the method comprises determining the solidification of the one or more condensates in one or more cells in the cellular composition. In some embodiments, the method comprises determining the solidification of the one or more condensates in a single cell in the cellular composition. In some embodiments, the method comprises determining the solidification of the one or more condensates in a portion of one or more cells in the cellular composition. In some embodiments, the method comprises determining the solidification of the one or more condensates in a portion of a single cell in the cellular composition. In some embodiments, the method comprises determining the solidification of the one or more condensates in the cytoplasm. In some embodiments, the method comprises determining the solidification of the one or more condensates in the nucleus. In some embodiments, the method comprises determining the solidification of the one or more condensates in an organelle.

In some embodiments, the solidification of one or more condensates, or a product thereof, is determined to be modulated by the compound when the solidification of the one or more condensates increases as compared to the reference, including reference condensates or a product thereof. In some embodiments, the solidification of one or more condensates is determined to be modulated by the compound when the solidification of the one or more condensates decreases as compared to the reference, including reference condensates. In some embodiments, the solidification of the one or more condensates in the first portion of the cellular composition decreases compared to the reference, and the solidification of the one or more condensates in the second portion of the cell composition does not decrease compared to the reference. In some embodiments, the solidification of the one or more condensates in the first portion of the cellular composition increases compared to the reference, and the solidification of the one or more condensates in the second portion of the cell composition does not increase compared to the reference. In some embodiments, the first portion of the cellular composition is the cytoplasm and the second portion of the cellular composition is the nucleus, or the first portion of the cellular composition is the nucleus and the second portion of the cellular composition is the cytoplasm. In some embodiments, the solidification of the one or more condensates in the cytoplasm decreases compared to the reference and the solidification of the one or more condensates in the nucleus does not decrease compared to the reference. In some embodiments, the solidification of the one or more condensates in the cytoplasm decreases compared to the reference and the solidification of the one or more condensates in the nucleus increases compared to the reference.

In some embodiments, the solidification of the one or more condensates in the first portion of the cellular composition increases compared to the second portion of the cell composition, or the solidification of the one or more condensates in the second portion of the cell composition increases compared to the first portion of the cell composition. In some embodiments, the first portion of the cellular composition is the cytoplasm and the second portion of the cellular composition is the nucleus, or the first portion of the cellular composition is the nucleus and the second portion of the cellular composition is the cytoplasm.

In some embodiments, the compound modulates the liquid-to-gel transition of the one or more condensates as compared to a reference. In some embodiments, the compound modulates the liquid-to-gel transition of the one or more condensates and does not modulate the gel-to-solid transition of the one or more condensates as compared to a reference. In some embodiments, the compound modulates the gel-to-solid transition of the one or more condensates as compared to a reference. In some embodiments, the compound modulates the gel-to-solid transition of the one or more condensates and does not modulate the liquid-to-gel transition of the one or more condensates as compared to a reference.

In some embodiments, the solidification of the one or more condensates is assessed via one or more of the following droplet size, surface tension, a phase diagram, equilibrium state, droplet coarsening, hardening, and fiber and/or aggregate formation.

In some embodiments, the solidification of one or more condensates is determined using an imaging technique. In some embodiments, the solidification of one or more condensates is determined by measuring the formation of an aggregate or a fiber. In some embodiments, the solidification of one or more condensates is determined using a filtration-based technique.

Dissolution of Condensates

In some embodiments, the characteristic associated with the one or more condensates is based on the dissolution of the one or more condensates. Accordingly, in some embodiments, provided herein are methods of identifying a compound that modulates a characteristic associated with one or more condensates comprising a condensate-associated molecule, the method comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the dissolution of the one or more condensates. In some embodiments, provided herein are methods of identifying a compound that modulates the dissolution of the one or more condensates, the method comprising: (a) contacting the compound with a cellular composition comprising one or more condensates or with a cellular composition that is capable of forming one or more condensates, and (b) determining the dissolution of the one or more condensates, wherein a modulation in the dissolution, as compared to a reference, indicates that the compound modulates the dissolution of the one or more condensates. In some embodiments, the dissolution is based on a measurement accounting for two or more condensates, e.g., the average or distribution of dissolution of two or more condensates.

The dissolution of condensates can be determined for one or more condensates in a portion or all of the cellular composition. Accordingly, in some embodiments, the method comprises determining the dissolution of the one or more condensates in a portion of the cellular composition. In some embodiments, the method comprises determining the dissolution of the one or more condensates in the entire cellular composition. In some embodiments, the method comprises determining the dissolution of the one or more condensates in one or more cells in the cellular composition. In some embodiments, the method comprises determining the dissolution of the one or more condensates in a single cell in the cellular composition. In some embodiments, the method comprises determining the dissolution of the one or more condensates in a portion of one or more cells in the cellular composition. In some embodiments, the method comprises determining the dissolution of the one or more condensates in a portion of a single cell in the cellular composition. In some embodiments, the method comprises determining the dissolution of the one or more condensates in the cytoplasm. In some embodiments, the method comprises determining the dissolution of the one or more condensates in the nucleus. In some embodiments, the method comprises determining the dissolution of the one or more condensates in an organelle.

In some embodiments, the dissolution of one or more condensates is determined to be modulated by the compound when the dissolution of the one or more condensates increases as compared to the reference. In some embodiments, the dissolution of one or more condensates is determined to be modulated by the compound when the dissolution of the one or more condensates decreases as compared to the reference. In some embodiments, the dissolution of the one or more condensates in the first portion of the cellular composition decreases compared to the reference, and the dissolution of the one or more condensates in the second portion of the cell composition does not decrease compared to the reference. In some embodiments, the dissolution of the one or more condensates in the first portion of the cellular composition increases compared to the reference, and the dissolution of the one or more condensates in the second portion of the cell composition does not increase compared to the reference. In some embodiments, the first portion of the cellular composition is the cytoplasm and the second portion of the cellular composition is the nucleus, or the first portion of the cellular composition is the nucleus and the second portion of the cellular composition is the cytoplasm. In some embodiments, the dissolution of the one or more condensates in the cytoplasm decreases compared to the reference and the dissolution of the one or more condensates in the nucleus does not decrease compared to the reference. In some embodiments, the dissolution of the one or more condensates in the cytoplasm decreases compared to the reference and the dissolution of the one or more condensates in the nucleus increases compared to the reference.

In some embodiments, the dissolution of the one or more condensates in the first portion of the cellular composition increases compared to the second portion of the cell composition, or the dissolution of the one or more condensates in the second portion of the cell composition increases compared to the first portion of the cell composition. In some embodiments, the first portion of the cellular composition is the cytoplasm and the second portion of the cellular composition is the nucleus, or the first portion of the cellular composition is the nucleus and the second portion of the cellular composition is the cytoplasm.

In some embodiments, the method comprises subjecting a cellular composition to a condensate-forming condition prior to contacting the compound with a cellular composition. In some embodiments, the dissolution is assessed via one or more of the number of condensates, the size of condensates, such as the reduction in size, the disappearance of condensates.

In some embodiments, the dissolution of one or more condensates is determined using an imaging technique.

Presence and/or Amount of Fiber Formation

In some embodiments, the characteristic associated with the one or more condensates is based on the presence and/or amount of fiber formation. In some embodiments, the characteristic associated with the one or more condensates is based on the presence of fiber formation. In some embodiments, the characteristic associated with the one or more condensates is based on the amount of fiber formation. Accordingly, in some embodiments, provided herein are methods of identifying a compound that modulates a characteristic associated with one or more condensates comprising a condensate-associated molecule, the method comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the presence and/or amount of fiber formation. In some embodiments, provided herein are methods of identifying a compound that modulates the presence and/or amount of fiber formation, the method comprising: (a) contacting the compound with a cellular composition comprising one or more condensates or with a cellular composition that is capable of forming one or more condensates, and (b) determining the presence and/or amount of fiber formation, wherein a modulation of the presence and/or amount of fiber formation, as compared to a reference, indicates that the compound modulates the presence and/or amount of fiber formation.

Fiber formation can be detected and measured by a variety of methods, such as by using a microscope to visualize a fiber and/or a fiber binding assay, such as a fiber binding assay described in the Examples.

The presence and/or amount of fiber formation can be determined for a portion or all of the cellular composition. Accordingly, in some embodiments, the method comprises determining the presence and/or amount of fiber formation in a portion of the cellular composition. In some embodiments, the method comprises determining the presence and/or amount of fiber formation in the entire cellular composition. In some embodiments, the method comprises determining the presence and/or amount of fiber formation in one or more cells in the cellular composition. In some embodiments, the method comprises determining the presence and/or amount of fiber formation in a single cell in the cellular composition.

The presence and/or amount of fiber formation can also be determined for a portion or all of a cell in the cellular composition. Accordingly, in some embodiments, the method comprises determining the presence and/or amount of fiber formation in a portion of one or more cells in the cellular composition. In some embodiments, the method comprises determining the presence and/or amount of fiber formation in a portion of a single cell in the cellular composition. In some embodiments, the method comprises determining the presence and/or amount of fiber formation in the cytoplasm. In some embodiments, the method comprises determining the presence and/or amount of fiber formation in the nucleus. In some embodiments, the method comprises determining the presence and/or amount of fiber formation in an organelle.

In some embodiments, the amount of fiber formation increases as compared to the reference. In some embodiments, the amount of fiber formation decreases as compared to the reference.

In some embodiments, the amount of fiber formation in the first portion of the cellular composition decreases compared to the reference, and the amount of fiber formation in the second portion of the cell composition does not decrease compared to the reference. In some embodiments, the amount of fiber formation in the first portion of the cellular composition increases compared to the reference, and the amount of fiber formation in the second portion of the cell composition does not increase compared to the reference. In some embodiments, the first portion of the cellular composition is the cytoplasm and the second portion of the cellular composition is the nucleus, or the first portion of the cellular composition is the nucleus and the second portion of the cellular composition is the cytoplasm. In some embodiments, the amount of fiber formation in the cytoplasm decreases compared to the reference and the amount of fiber formation in the nucleus does not decrease compared to the reference. In some embodiments, the amount of fiber formation in the cytoplasm decreases compared to the reference and the amount of fiber formation in the nucleus increases compared to the reference.

In some embodiments, the amount of fiber formation in the first portion of the cellular composition increases compared to the second portion of the cell composition, or the amount of fiber formation in the second portion of the cell composition increases compared to the first portion of the cell composition. In some embodiments, the first portion of the cellular composition is the cytoplasm and the second portion of the cellular composition is the nucleus, or the first portion of the cellular composition is the nucleus and the second portion of the cellular composition is the cytoplasm.

Location of Condensate-Associated Molecules

In some embodiments, the characteristic associated with the one or more condensates is based on the location of the one or more condensates. Accordingly, in some embodiments, provided herein are methods of identifying a compound that modulates a characteristic associated with one or more condensates comprising a condensate-associated molecule, the method comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the location of the one or more condensates. In some embodiments, provided herein are methods of identifying a compound that modulates the location of the one or more condensates, the method comprising: (a) contacting the compound with a cellular composition comprising one or more condensates or with a cellular composition that is capable of forming one or more condensates, and (b) determining the location of the one or more condensates, wherein a modulation in the location, as compared to a reference, indicates that the compound modulates the location of the one or more condensates.

The location of condensates can be determined for a portion or all of the cellular composition. Accordingly, in some embodiments, the method comprises determining the location of the one or more condensates in a portion of the cellular composition. In some embodiments, the method comprises determining the location of the one or more condensates in the entire cellular composition. In some embodiments, the method comprises determining the location of the one or more condensates in one or more cells in the cellular composition. In some embodiments, the method comprises determining the location of the one or more condensates in a single cell in the cellular composition.

The location of condensates can also be determined for a portion or all of a cell in the cellular composition. Accordingly, in some embodiments, the method comprises determining the location of the one or more condensates in a portion of one or more cells in the cellular composition. In some embodiments, the method comprises determining the location of the one or more condensates in a portion of a single cell in the cellular composition. In some embodiments, the method comprises determining the location of the one or more condensates in the cytoplasm. In some embodiments, the method comprises determining the location of the one or more condensates in the nucleus. In some embodiments, the method comprises determining the location of the one or more condensates in an organelle.

In some embodiments, the location of one or more condensates is determined using an imaging technique.

Partitioning of the Condensate-Associated Molecule into Condensates

In some embodiments, the characteristic associated with the one or more condensates is based on the partitioning of the condensate-associated molecule into the one or more condensates. Accordingly, in some embodiments, provided herein are methods of identifying a compound that modulates a characteristic associated with one or more condensates comprising a condensate-associated molecule, the method comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the partitioning of the condensate-associated molecule into the one or more condensates. In some embodiments, provided herein are methods of identifying a compound that modulates the partitioning of the condensate-associated molecule into the one or more condensates, the method comprising: (a) contacting the compound with a cellular composition comprising one or more condensates or with a cellular composition that is capable of forming one or more condensates, and (b) determining the partitioning of the condensate-associated molecule into the one or more condensates, wherein a modulation of the partitioning, as compared to a reference, indicates that the compound modulates the partitioning of the condensate-associated molecule into the one or more condensates.

The partitioning of condensate-associated molecules into condensates can be determined for a portion or all of the cellular composition. Accordingly, in some embodiments, the method comprises determining the partitioning of the condensate-associated molecule into the one or more condensates in a portion of the cellular composition. In some embodiments, the method comprises determining the partitioning of the condensate-associated molecule into the one or more condensates in the entire cellular composition. In some embodiments, the method comprises determining the partitioning of the condensate-associated molecule into the one or more condensates in one or more cells in the cellular composition. In some embodiments, the method comprises determining the partitioning of the condensate-associated molecule into the one or more condensates in a single cell in the cellular composition.

The partitioning of condensate-associated molecules into condensates can also be determined for a portion or all of a cell in the cellular composition. Accordingly, in some embodiments, the method comprises determining the partitioning of the condensate-associated molecule into the one or more condensates in a portion of one or more cells in the cellular composition. In some embodiments, the method comprises determining the partitioning of the condensate-associated molecule into the one or more condensates in a portion of a single cell in the cellular composition. In some embodiments, the method comprises determining the partitioning of the condensate-associated molecule into the one or more condensates in the cytoplasm. In some embodiments, the method comprises determining the partitioning of the condensate-associated molecule into the one or more condensates in the nucleus. In some embodiments, the method comprises determining the partitioning of the condensate-associated molecule into the one or more condensates in an organelle.

In some embodiments, the partitioning of the condensate-associated molecule into the one or more condensates increases as compared to the reference. In some embodiments, the partitioning of the condensate-associated molecule into the one or more condensates decreases as compared to the reference.

In some embodiments, the partitioning of the condensate-associated molecule into the one or more condensates in the first portion of the cellular composition decreases compared to the reference, and the partitioning of the condensate-associated molecule into the one or more condensates in the second portion of the cell composition does not decrease compared to the reference. In some embodiments, the partitioning of the condensate-associated molecule into the one or more condensates in the first portion of the cellular composition increases compared to the reference, and the partitioning of the condensate-associated molecule into the one or more condensates in the second portion of the cell composition does not increase compared to the reference. In some embodiments, the first portion of the cellular composition is the cytoplasm and the second portion of the cellular composition is the nucleus, or the first portion of the cellular composition is the nucleus and the second portion of the cellular composition is the cytoplasm. In some embodiments, the partitioning of the condensate-associated molecule into the one or more condensates in the cytoplasm decreases compared to the reference and the partitioning of the condensate-associated molecule into the one or more condensates in the nucleus does not decrease compared to the reference. In some embodiments, the partitioning of the condensate-associated molecule into the one or more condensates in the cytoplasm decreases compared to the reference and the partitioning of the condensate-associated molecule into the one or more condensates in the nucleus increases compared to the reference.

In some embodiments, the partitioning of the condensate-associated molecule into the one or more condensates in the first portion of the cellular composition increases compared to the second portion of the cell composition, or the partitioning of the condensate-associated molecule into the one or more condensates in the second portion of the cell composition increases compared to the first portion of the cell composition. In some embodiments, the first portion of the cellular composition is the cytoplasm and the second portion of the cellular composition is the nucleus, or the first portion of the cellular composition is the nucleus and the second portion of the cellular composition is the cytoplasm.

Aggregation of the Condensate-Associated Molecule

In some embodiments, the characteristic associated with the one or more condensates is based on the aggregation of the condensate-associated molecule. Accordingly, in some embodiments, provided herein are methods of identifying a compound that modulates a characteristic associated with one or more condensates comprising a condensate-associated molecule, the methods comprising: (a) contacting the compound with a cellular composition comprising one or more condensates or with a cellular composition that is capable of forming one or more condensates, and (b) determining the characteristic associated with the one or more condensates, wherein a modulation in the characteristic, as compared to a reference, indicates that the compound modulates the characteristic associated with the one or more condensates, wherein the characteristic is the modulation of the aggregation of the condensate-associated molecule. In some embodiments, provided herein are methods of identifying a compound that modulates the aggregation of the condensate-associated molecule, the methods comprising: (a) contacting the compound with a cellular composition comprising one or more condensates or with a cellular composition that is capable of forming one or more condensates, and (b) determining the aggregation of the condensate-associated molecule, wherein a modulation of the aggregation, as compared to a reference, indicates that the compound modulates the aggregation of the condensate-associated molecule.

The aggregation of condensate-associated molecules can be determined for a portion or all of the cellular composition. Accordingly, in some embodiments, the method comprises determining the aggregation of the condensate-associated molecule in a portion of the cellular composition. In some embodiments, the method comprises determining the aggregation of the condensate-associated molecule in the entire cellular composition. In some embodiments, the method comprises determining the aggregation of the condensate-associated molecule in one or more cells in the cellular composition. In some embodiments, the method comprises determining the aggregation of the condensate-associated molecule in a single cell in the cellular composition.

The aggregation of condensate-associated molecules can also be determined for a portion or all of a cell in the cellular composition. Accordingly, in some embodiments, the method comprises determining the aggregation of the condensate-associated molecule in a portion of one or more cells in the cellular composition. In some embodiments, the method comprises determining the aggregation of the condensate-associated molecule in a portion of a single cell in the cellular composition. In some embodiments, the method comprises determining the aggregation of the condensate-associated molecule in the cytoplasm. In some embodiments, the method comprises determining the aggregation of the condensate-associated molecule in the nucleus. In some embodiments, the method comprises determining the aggregation of the condensate-associated molecule in an organelle.

In some embodiments, the aggregation of the condensate-associated molecule increases as compared to the reference. In some embodiments, the aggregation of the condensate-associated molecule decreases as compared to the reference.

In some embodiments, the aggregation of the condensate-associated molecule in the first portion of the cellular composition decreases compared to the reference, and the aggregation of the condensate-associated molecule in the second portion of the cell composition does not decrease compared to the reference. In some embodiments, the aggregation of the condensate-associated molecule in the first portion of the cellular composition increases compared to the reference, and the aggregation of the condensate-associated molecule in the second portion of the cell composition does not increase compared to the reference. In some embodiments, the first portion of the cellular composition is the cytoplasm and the second portion of the cellular composition is the nucleus, or the first portion of the cellular composition is the nucleus and the second portion of the cellular composition is the cytoplasm. In some embodiments, the aggregation of the condensate-associated molecule in the cytoplasm decreases compared to the reference and the aggregation of the condensate-associated molecule in the nucleus does not decrease compared to the reference. In some embodiments, the aggregation of the condensate-associated molecule in the cytoplasm decreases compared to the reference and the aggregation of the condensate-associated molecule in the nucleus increases compared to the reference.

In some embodiments, the aggregation of the condensate-associated molecule in the first portion of the cellular composition increases compared to the second portion of the cell composition, or the aggregation of the condensate-associated molecule in the second portion of the cell composition increases compared to the first portion of the cell composition. In some embodiments, the first portion of the cellular composition is the cytoplasm and the second portion of the cellular composition is the nucleus, or the first portion of the cellular composition is the nucleus and the second portion of the cellular composition is the cytoplasm.

Compounds

"Compound" used herein refers to any agent. In some embodiments, the compound is a small molecule, a polypeptide, a lipid, or a nucleic acid. In some embodiments, the compound is an approved compound, such as a compound approved for medical treatment by the United States Food and Drug Administration. In some embodiments, the compound is a novel compound. In some embodiments, the compound is charged. In some embodiments, the compound is hydrophobic. In some embodiments, the compound is hydrophilic. In some embodiments, the compound is a small molecule. In some embodiments, the small molecule is an alkaloid, a glycoside, a phenazine, a phenol, a polyketide, a terpene, or a tetrapyrrole. In some embodiments, the compound is an antibody. In some embodiments, the compound is a nucleic acid. In some embodiments, the compound is RNA, such as a siRNA, miRNA, or mRNA. In some embodiments, the compound is a non-naturally occurring compound. In some embodiments, the compound is a naturally occurring compound. When a plurality of candidate compounds are used for screening, the plurality of candidate compounds can be of the same type or of different types.

In some embodiments, the compound is capable of selectively interacting non-covalently with a biomolecule (particularly a protein or nucleic acid) under conditions prevailing in a live cell, wherein said compound and said biomolecule form a complex having a dissociation constant kd of $10^{-4}$ mol/l or less. In some embodiments, the compound has a molecular mass of more than 160 Da but less than 1000 Da, particularly less than 700 Da, more particularly less than 500 Da, and the compound comprises up to five hydrogen bond donators, up to ten hydrogen bond acceptors and is characterized by an octanol-water partition coefficient log P of below 5.6. These are the so-called "Lipinski" rules of 5 (originally, referring to molecules between 160 and 500 Da) for drug-like compounds. It is understood that any of these embodiments may apply and be combined with any compound (including the preceding paragraph) as described herein.

Cells and Condensates

In some embodiments, the cellular composition comprises a microorganism or an animal cell. In some embodiments, the cellular composition comprises a human cell. In some embodiments, the cellular composition comprises a neuron. In some embodiments, the cellular composition comprises a cancer cell. In some embodiments, the cellular composition comprises a cell that is or is derived from induced pluripotent stem cells (iPS cells), HeLa cells, or HEK293 cells. In some embodiments, the cellular composition comprises a condensate that is dysregulated. In some embodiments, the cellular composition comprises a cell comprising a mutation associated with a disease. In some embodiments, the cellular composition comprises a cell having one or more features of a neurodegenerative or proliferative disease. In some embodiments, the cellular composition comprises a cell expressing a protein that is labeled with a fluorescent protein. In some embodiments, the protein is a protein known to concentrate in a condensate. In some embodiments, the condensate-associated molecule is labeled, such as by attachment or fusion to a fluorescent protein.

In some embodiments, a cell in the cellular composition expresses the condensate-associated molecule. In some embodiments, expression may include any of gene duplication, transcription, and translation. In some embodiments, the condensate-associated molecule is a polynucleotide, such as a RNA, wherein the condensate-associated molecule is transcribed in a cell in a cellular composition. In some embodiments, the condensate-associated molecule is a polypeptide, such as a protein, wherein the condensate-associated molecule is translated in a cell in a cellular composition. In some embodiments, the condensate-associated molecule is heterologous to the cell.

Many condensates are well known in the art. Examples of known condensates include cleavage bodies, p-granules, histone locus bodies, multivesicular bodies, neuronal RNA granules, nuclear gems, nuclear pores, nuclear speckles, nuclear stress bodies, a nucleolus, Oct1/PTF/transcription (OPT) domains, paraspeckles, perinucleolar compartments, PML nuclear bodies, PML oncogenic domains, polycomb bodies, processing bodies, Sam68 nuclear bodies, stress granules, or splicing speckles. Numerous more condensates are known to form, but have not yet been described. Many condensates can be identified using microscopy. In some embodiments, the methods further comprise identifying the one or more condensates. In some embodiments, the one or more condensates are cellular condensates. In some embodiments, the one or more condensates are within one or more cells in the cellular composition. In some embodiments, the one or more condensates are one or more stress granules. In some embodiments, the first set of one or more condensates are one or more stress granules. In some embodiments, the second set of one or more condensates are one or more nuclear paraspeckles, condensates formed around sites of DNA damage, P bodies, Cajal bodies, and PML bodies.

In some embodiments, the condensate is selected from the group consisting of a stress granule, P body, Cajal body, PML body, paraspeckle, e.g., a nuclear paraspeckle, DNA damage foci condensate, cleavage body, p-granule, histone locus body, multivesicular body, neuronal RNA granule, nuclear gem, nuclear pore, nuclear stress body, nucleolus, Oct1/PTF/transcription (OPT) domain, perinucleolar compartment, PML oncogenic domain, polycomb body, processing body, Sam68 nuclear body, and splicing speckle. Exemplary condensates are discussed in, e.g., Banani et al., *Nat Rev Mol Cell Biol,* 18, 2017, "Biomolecular condensates: organizers of cellular biochemistry;" Brangwynne et al., *Science,* 324, 2009, "Germline P granules are liquid droplets that localize by controlled dissolution/condensation;" Patel et al., *Cell,* 162, 2015, "A Liquid-to-Solid Phase Transition of the ALS Protein Accelerated by Disease Mutation;" Alberti, S., *Current Biology,* 27, R1089-R1107, 2017, "Phase Separation in Biology."

Condensate-Associated Molecules

In some embodiments, the condensate-associated molecule is a polynucleotide or polypeptide. In some embodiments, the condensate-associated molecule is a polypeptide. In some embodiments, the condensate-associated molecule is a wild-type polypeptide. In some embodiments, the condensate-associated molecule is a mutant polypeptide. In some embodiments, the condensate-associated molecule is FUS, EWSR1, TIAL1, PABPC1, or G3BP1, or a mutant thereof. In some embodiments, the condensate-associated molecule is FUS.

Additional Assays

In some embodiments, the methods further comprises assessing the compound by one or more additional assays, such as one or more of a second cell-based assay, a biochemical assay, and an in vivo assay.

In some embodiments, the biochemical assay method is a method of identifying a compound that modulates a characteristic associated with a condensate.

In some embodiments, the biochemical assay method comprises (a) admixing the compound and a precursor molecule to form a reaction composition, (b) subjecting the reaction composition to a condensate-forming condition, wherein, if formed, the condensate comprises the precursor molecule; and (c) determining the characteristic associated with the condensate, wherein a modulation in the characteristic, as compared to a reference, identifies the compound as a compound that modulates the characteristic. In some embodiments, the condensate-forming condition is a reduced salt concentration. In some embodiments, the method is repeated with different a different condensate-forming condition.

In some embodiments, the biochemical assay method comprises (a) admixing the compound and the condensate comprising a precursor molecule to form a reaction composition; and (b) determining the characteristic associated with the condensate, wherein a modulation in the characteristic, as compared to a reference, identifies the compound as a compound that modulates the characteristic. In some embodiments, the biochemical assay method further comprises subjecting the reaction composition to an aging condition after admixing the compound and the condensate to form the reaction composition. In some embodiments, the aging condition is: incubation, shaking, and/or heat.

In some embodiments, determining the characteristic associated with the condensate is based on any one or more of the following: (i) number of condensates; (ii) size of the condensate; (iii) partitioning of the precursor molecule into the condensate; (iv) surface area of the condensate; (v) composition of the condensate; (vii) liquidity of the condensate; (viii) solidification of the condensate; (ix) aggregation of the precursor molecule; (x) dissolution of the condensate; and (xi) presence and/or amount of fiber formation.

In some embodiments, the precursor molecule is a polypeptide. In some embodiments, the precursor molecule is a wildtype polypeptide. In some embodiments, the precursor molecule is a mutant polypeptide. In some embodiments, the polypeptide is selected from the group consisting of: FUS, EWSR1, TIAL1, PABPC1, and G3BP1.

In some embodiments, the biochemical assay the method further comprises imaging the reaction composition after subjecting the reaction composition to the condensate-forming condition. In some embodiments, the reaction composition comprises the compound and the precursor molecule at a fixed ratio. In some embodiments, the biochemical assay method is repeated with two or more different ratios of the compound and the precursor molecule.

In some embodiments, the reference is a reaction composition that does not comprise the compound.

EXEMPLARY EMBODIMENTS

Among the provided embodiments are:

Embodiment 1. A compound for use in a method for preventing or a neurodegenerative disease associated with the formation of stress granules, wherein said compound is selected from
  lipoic acid
  lipoamide,
  dihydrolipoic acid, and
  dihydrolipoamide.

Embodiment 2. The compound for use in a method for preventing or a neurodegenerative disease associated with the formation of stress granules according to embodiment 1, comprising the dosage regimen:
  administering a daily dose of 600 mg to 1,600 mg of said compound.

Embodiment 3. The compound for use in a method for preventing or a neurodegenerative disease associated with the formation of stress granules according to embodiment 1 or 2, wherein said neurodegenerative disease associated with the formation of stress granules is amyotrophic lateral sclerosis.

Embodiment 4. A pharmaceutical composition for use in a method for preventing or treating a neurodegenerative associated with the formation of stress granules comprising a compound according to any one of embodiments 1 to 3.

Embodiment 5. The pharmaceutical composition for use in a method for preventing or treating amyotrophic lateral sclerosis according to embodiment 4, wherein said pharmaceutical composition is formulated for oral application.

Embodiment 6. The pharmaceutical composition according embodiment 4 or 5, wherein said neurodegenerative disease associated with the formation of stress granules is amyotrophic lateral sclerosis.

Embodiment 7. A dosage form for use in a method for preventing or treating amyotrophic lateral sclerosis comprising a compound according to any one of embodiments 1, particularly administered at a dosage as specified in embodiment 2.

Embodiment 8. The dosage form according to embodiment 7, wherein said dosage form is formulated for oral application.

Embodiment 9. The dosage form according embodiment 7 or 8, wherein said neurodegenerative disease associated with the formation of stress granules is amyotrophic lateral sclerosis.

Embodiment 10. A method for treating or preventing a neurodegenerative disease associated with the formation of stress granules comprising administering a compound according to embodiment 1 to a patient in need thereof.

Embodiment 11. The method for treating or preventing a neurodegenerative disease according to embodiment 10, wherein said compound is administered in a daily dose of 600 mg to 1,600 mg.

Embodiment 12. The method for treating or preventing a neurodegenerative disease according to embodiment 10 or 11, wherein said compound is administered orally.

Embodiment 13. The method for treating or preventing a neurodegenerative disease according to any one of embodiments 10 to 12, said neurodegenerative disease associated with the formation of stress granules is amyotrophic lateral sclerosis.

Embodiment 14. A method for reducing or inhibiting the formation of stress granules in a cell comprising the use of a compound selected from
  lipoic acid
  lipoamide,
  dihydrolipoic acid, and
  dihydrolipoamide,
  a heterotricyclic compound, particularly an anthraquinone or anthraquinone derivative such as 1,4-dihydroxyanthraquinone, an acridine or acridine derivative such as quinacrine or aminoacridine or mitoxantrone;
  a tetracyclic compound, and
  a surfactant, particularly cetylpyridium chloride.

Further Exemplary Embodiments

Also among the provided embodiments are:

E1. A method of identifying a compound that modulates a characteristic associated with one or more condensates comprising a condensate-associated molecule, the method comprising: (a) contacting the compound with a cellular composition comprising one or more condensates or a cellular composition capable of forming one or more condensates, and (b) determining the characteristic associated with the one or more condensates, wherein a modulation in the characteristic, as compared to a reference, indicates that the compound modulates the characteristic associated with the one or more condensates.

E2. The method of embodiment E1, wherein determining the characteristic associated with the one or more condensates is based on any one or more of the following: (i) number of condensates comprising and/or not comprising the condensate-associated molecule; (ii) size of the one or more condensates; (iii) location of the one or more condensates; (iv) distribution of one or more condensates; (v) surface area of the one or more condensates; (vi) composition of the one or more condensates; (vii) liquidity of the one or more condensates; (viii) solidification of the one or more condensates; (ix) dissolution of the one or more condensates; (x) presence and/or amount of fiber formation; (xi) location of the condensate-associated molecule; (xii) partitioning of the condensate-associated molecule into the one or more condensates; and (xiii) aggregation of the condensate-associated molecule.

E3. The method of embodiment E1 or E2, wherein the one or more condensates are within one or more cells in the cellular composition.

E4. The method of any one of embodiments E1-E3, further comprising subjecting the cellular composition to a condensate-forming condition prior to step (b).

E5. The method of any one of embodiments E1-E3, further comprising subjecting the cellular composition to a condensate-forming condition prior to step (a).

E6. The method of embodiment E4 or E5, wherein the condensate-forming condition is any one or more of: (i) an oxidative stressor; (ii) a mitochondrial electron transport chain inhibitor; (iii) a heat stressor; (iv) an osmotic stressor; (v) a hyperosmotic stressor; and (vi) glycolysis inhibition.

E7. The method of any one of embodiments E1-E6, wherein the condensate-associated molecule is a polypeptide.

E8. The method of any one of embodiments E1-E7, wherein the condensate-associated molecule is a wildtype polypeptide.

E9. The method of any one of embodiments E1-E7, wherein the condensate-associated molecule is a mutant polypeptide.

E10. The method of any one of embodiments E1-E9, wherein the condensate-associated molecule is selected from the group consisting of: FUS, EWSR1, TIAL1, PABPC1, and G3BP1.

E11. The method of any one of embodiments E1-E10, wherein a cell in the cellular composition expresses the condensate-associated molecule.

E12. The method of any one of embodiments E1-E11, wherein the cellular composition comprises a HeLA, iPSC, or iPSC MN cell.

E13. The method of any one of embodiments E1-E12, further comprising imaging at least a portion of the cellular composition.

E14. The method of any one of embodiments E1-E13, further comprising contacting at least a portion of the cellular composition with a fixative.

E15. The method of any one of embodiments E1-E14, further comprising contacting at least a portion of the cellular composition with a stain.

E16. The method of any one of embodiments E1-E15, further comprising contacting at least a portion of the cellular composition with a DNA-damaging condition.

E17. The method of embodiment E16, wherein the DNA-damaging condition is laser irradiation.

E18. The method of any one of embodiments E1-E17, wherein the reference is a second condensate.

E19. The method of any one of embodiments E1-E17, wherein the reference is a second cellular composition.

E20. The method of any one of embodiments E1-E19, further comprising assessing the identified compound using a second cell-based assay.

E21. The method of any one of embodiments E1-E20, further comprising assessing the identified compound using a biochemical assay.

E22. The method of any one of embodiments E1-E21, further comprising assessing the identified compound using an in vivo assay.

E23. A method of identifying a compound useful for treating a disease, the method comprising identifying a compound according to any one of the methods of embodiments E1-E22.

E24. The method of embodiment E23, wherein the disease is a neurodegenerative disease.

E25. The method of embodiment E24, wherein the neurodegenerative disease is ALS.

E26. The method of any one of the preceding embodiments E1 to E25, wherein the condensate is a non-membrane-encapsulated compartment formed by phase separation of one or more of proteins and other macromolecules, particularly DNA and/or RNA.

E27. The method of E27, wherein the condensate is selected from the group consisting of a stress granule, a P body, a Cajal body, a promyelocytic leukemia protein (PML) body, a paraspeckle, e.g., a nuclear paraspeckle, a DNA damage foci condensate, a cleavage body, a p-granule, a histone locus body, a multivesicular body, a neuronal RNA granule, a nuclear gem, a nuclear pore, a nuclear stress body, a nucleolus, an Oct1/PTF/transcription (OPT) domain, a perinucleolar compartment, a PML oncogenic domain, a polycomb body, a processing body, a Sam68 nuclear body, and a splicing speckle.

Those skilled in the art will recognize that several embodiments are possible within the scope and spirit of the disclosure of this application. The invention is further illustrated by the following examples and figures, from which further embodiments and advantages can be drawn. These examples are meant to illustrate the invention but not to limit its scope.

EXAMPLES

Example 1

Screening for Compounds Using FUS as a Model LCD/RBP Stress Granule Protein

Figure 1B:
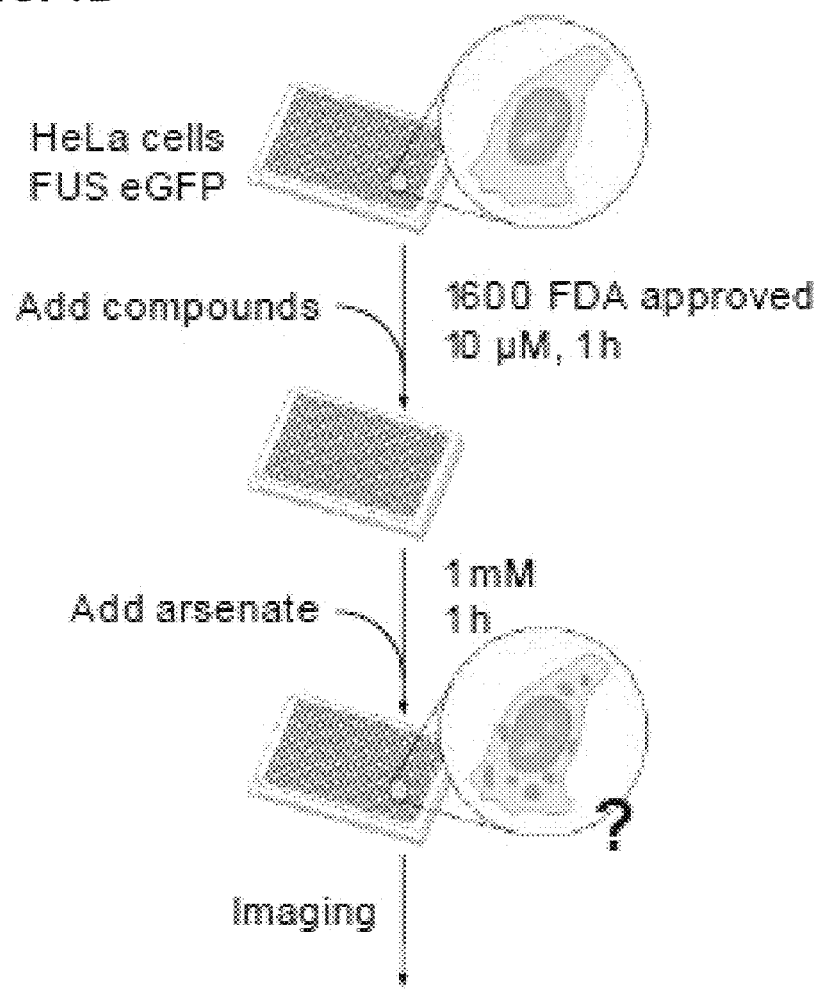

The inventors developed a cell-based screen using a HeLa cell line that stably expresses GFP-tagged FUS at near-endogenous levels. While not required for stress granule formation, FUS is a well-characterised protein with a domain structure typical of stress granule proteins. In the absence of cellular stress, FUS-GFP primarily localizes to the nucleus, where it is partially excluded from the nucleolus and localises to small puncta called paraspeckles (FIG. 1A). These are nuclear droplets implicated in retaining RNA in the nucleus for rapid stress response. Cells were pre-treated with 10 µM compound from a compound library for 1 h, then the cells were stressed with 1 mM potassium arsenate (still in the presence of compound) (FIG. 1B) and monitored FUS localization to stress granules. Arsenate disrupts antioxidant responses by reacting with thiol groups, blocks the tricarboxylic acid (TCA) cycle by reacting with the thiols in vital lipoyl moieties and causes general oxidative damage. In untreated stressed cells, FUS is partly exported to the cytoplasm where, in combination with other proteins and mRNA, it phase separates to form liquid-like stress granules surrounded by cytoplasm depleted in FUS (FIG. 1A).

Figure 1C:
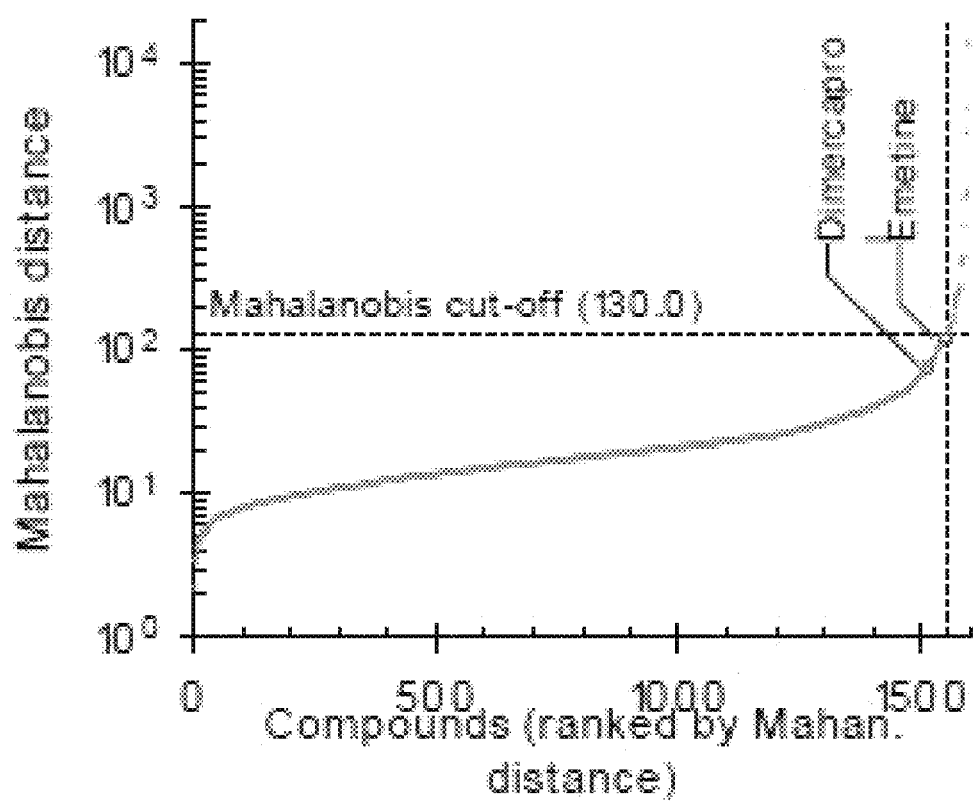

Many compounds affected stress granule formation. Multi-parameter image analysis, including cytoplasmic puncta number, nuclear puncta number, and nuclear/cytoplasm partition, was used to rank compounds by strength of effect on FUS localisation in stressed cells (FIG. 1C). The two compounds in the library expected to give a reduction of stress granules did so. These were the polysome stabilising compound emetine, which prevents release of mRNA, and the heavy metal chelating compound dimercaprol (which should sequester the stressor). Edaravone, thought to be an antioxidant and used as an ALS therapeutic in Japan and the US, had no effect on FUS localization in arsenate-stressed cells. Novel hit classes which tended to have a large effect on FUS localisation, typically reducing stress granule number, included cardiac glycosides, heterotri- and tetracyclic compounds (anthraquinones and acridines), surfactants, and benzimidazoles.

Figure 1D:
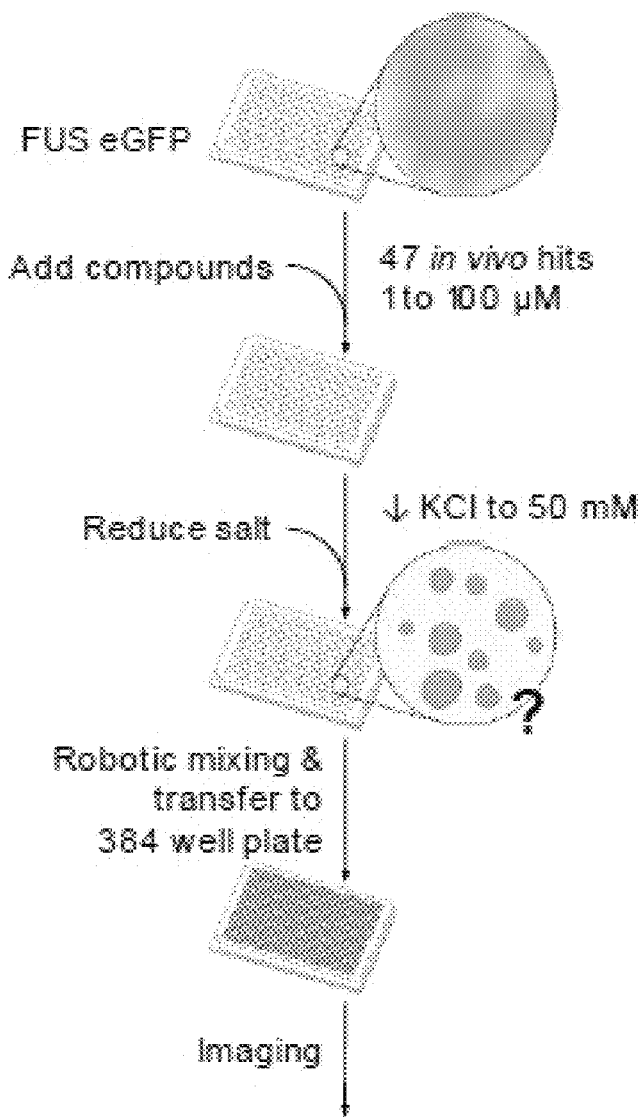
Figure 1E:
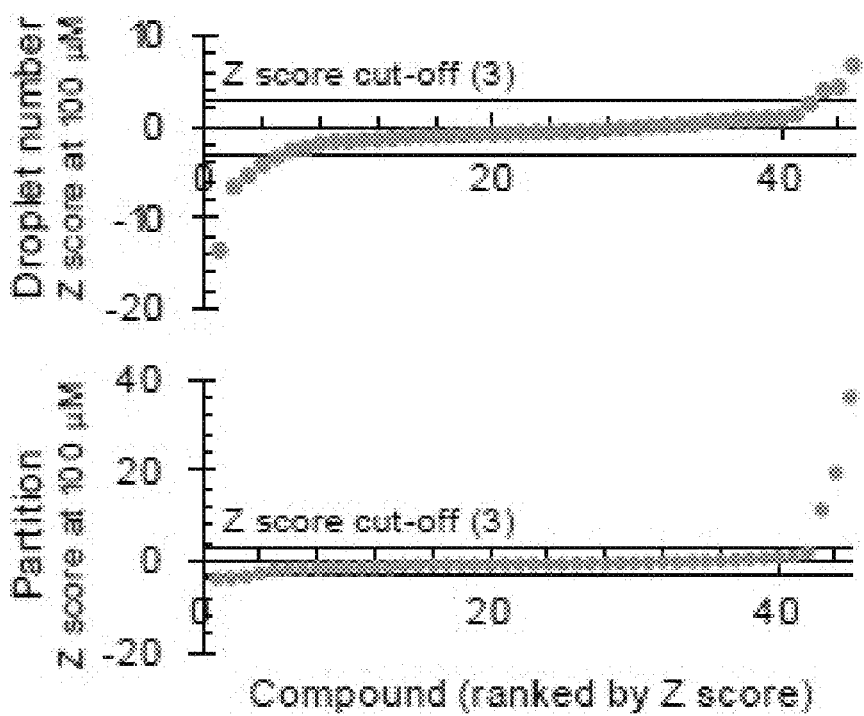
Figure 1F:
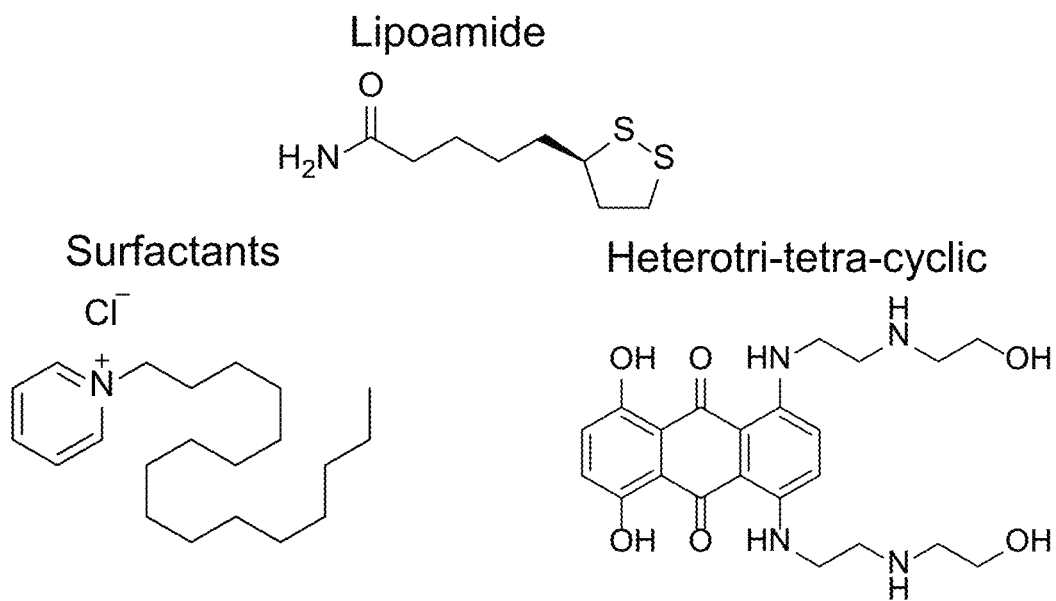

Compounds that can directly interact with FUS were of primary interest, therefore the inventors performed a follow up screen for action of compounds on FUS droplet formation in vitro (FIG. 1D). The inventors analysed the top 47 strongest hits from the cell-based screen. Hits were identified by the effect on number of FUS droplets formed and the partition of FUS into the droplets formed under low salt conditions in vitro in the presence of 1 mM DTT to mimic the reducing intracellular environment (FIG. 1E). Of these 47 compounds 7 significantly affected FUS in vitro (FIG. 1E) and this identified three compound classes as directly affecting FUS droplet formation. Surfactants, heterotri- and tetracyclic compounds and lipoamide, of which the latter two are plausible therapeutics (FIG. 1F).

Figure 1G:
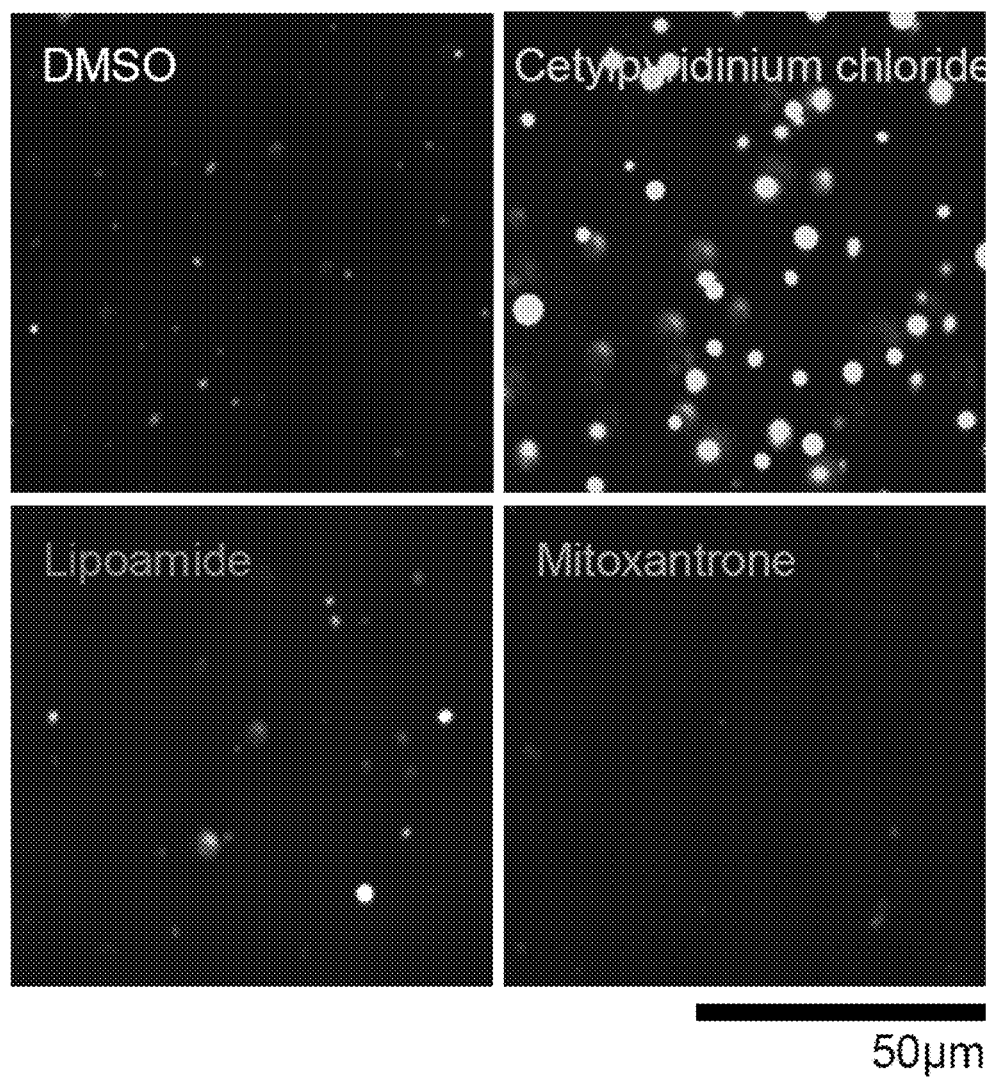

In this non-equilibrium snapshot, the heterotri- and tetracyclic compounds tended to reduce condensate formation in a dose-dependent manner and the resulting droplets were smaller. In contrast, surfactants and lipoamide tended to increase condensate droplet number, partition into droplets and the droplets were larger (FIGS. 1E and 1G). Surfactants are not plausible therapeutics as they will permeabalise cell membranes, and were present in the library due to their use as topical antiseptics.

Stress granule formation is associated with an export of FUS from the nucleus, typical of LCD/RBP-containing stress granule proteins. Persistent stress granules or stress granule protein is likely to give a harmful loss of nuclear function, including reduction of the FUS DNA damage response. Restoration of the nuclear localization of such proteins would likely be beneficial.

Figure 2A:
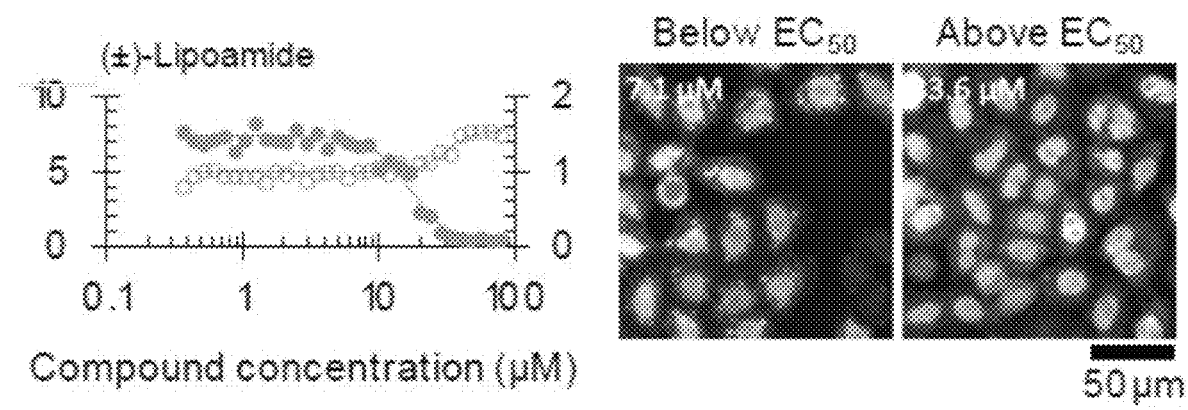
Figure 2B:
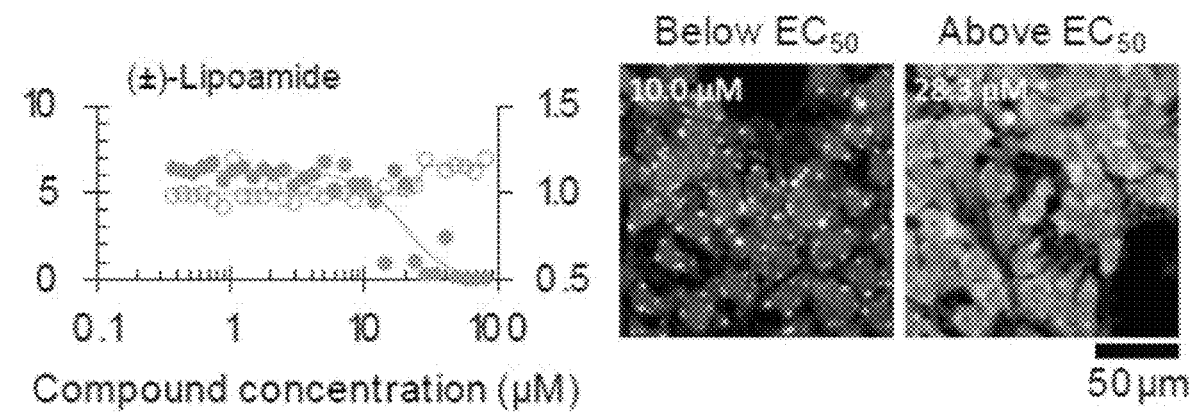
Figure 10A:
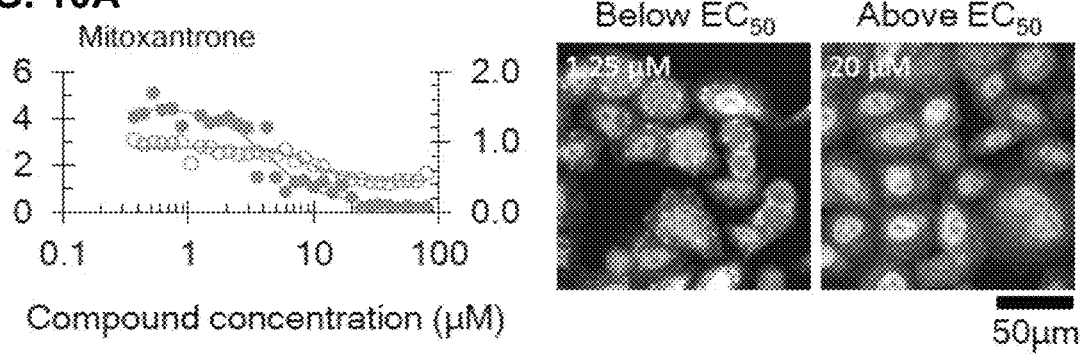
Figure 10B:
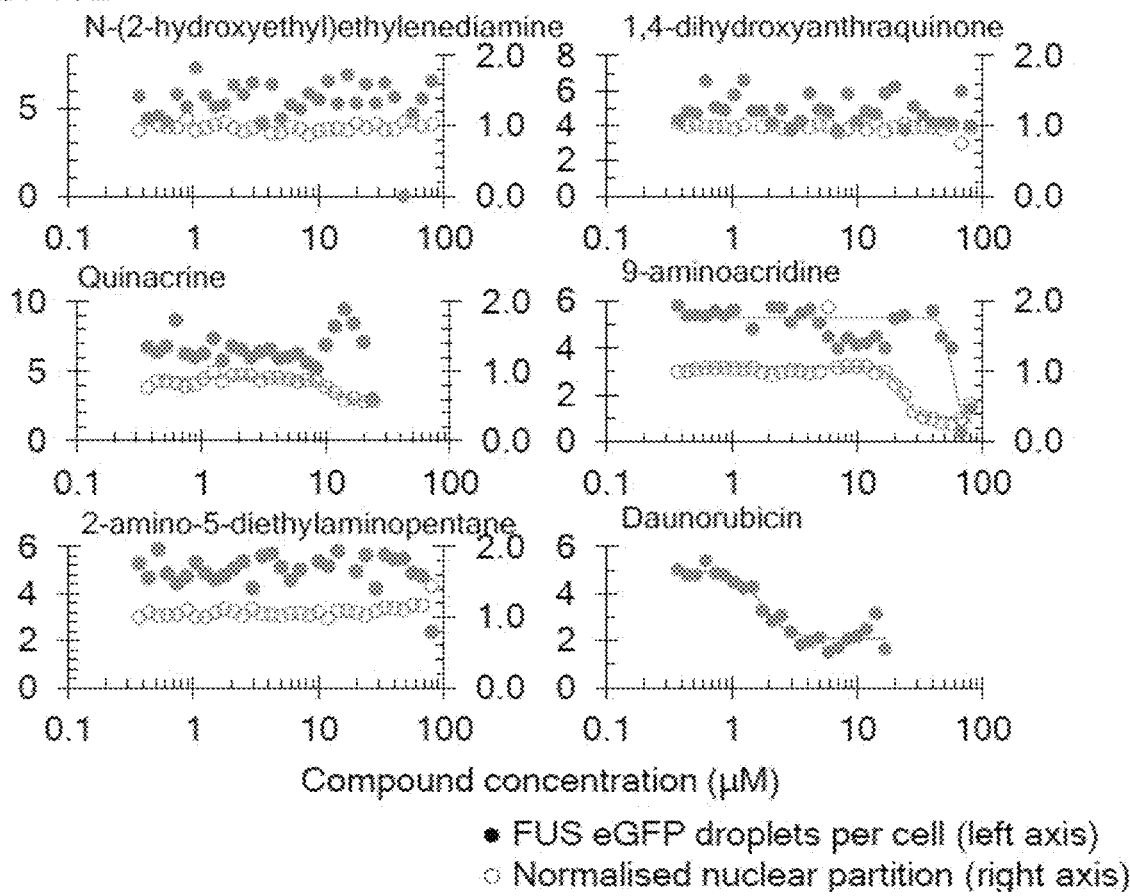

Accordingly, the dose dependent activity of lipoamide, lipoic acid and related compounds was analyzed. In HeLa cells expressing FUS GFP, a dose response analysis showed lipoamide both reducing the number of stress granules, and increased nuclear/cytoplasm FUS partition, with a similar $EC_{50}$ (FIG. 2A). Not all hits had this behavior, for example mitoxantrone (a heterotricyclic anthraquinone) decreased nuclear/cytoplasm FUS partition while reducing stress granule number (FIGS. 10A-10C). The inventors confirmed these key activities of lipoamide using an induced pluripotent stem cell (iPSC) line expressing FUS GFP under arsenate stress. This also showed lipoamide reduced stress granule number and restored a nuclear FUS location (FIG. 2B). Lipoamide therefore seems to reverse both FUS export from the nucleus and incorporation into stress granules in response to stress. It was later shown that lipoic acid has the same effect (see below). Return of FUS to the nucleus is likely beneficial, mimicking the unstressed cell state, indicating lipoamide is a more promising candidate.

Lipoamide is related to lipoic acid, which is a naturally occurring compound. Lipoic acid has two stereoisomers, of which R-(+)-lipoic acid naturally occurs in cells and is synthesised in the mitochondrion while S-(−)-lipoic acid is not. The mixture of both isomers is racemic lipoic acid or (+)-lipoic acid. It is present at very low free concentrations in the cell, and is normally covalently bonded to proteins as a lipoyl moiety via a secondary amide. This bound form is similar to lipoamide. These compounds are dithoils and the thiols of the lipoyl moiety are used by several enzymes (including one feeding into and one in the tricarboxylic acid (TCA) cycle) as hydrogen carriers. The R-(+) isomer can be interconverted between the oxidized (dithiol) and reduced (cyclic disulphide) state in cells by dihydrolipoamide dehydrogenase, and it is thought these compounds are antioxidants although evidence for direct action as an antioxidant is disputed. Importantly, lipoic acid and lipoamide are both are non-toxic and lipoic acid has well-characterised pharmacokinetics: It is non-toxic and 1,600 mg orally gives plasma concentrations of 8 to 30 µM in humans. This is extremely promising as the concentrations on the order of 10 µM used for characterization ex vivo can be achieved in humans-lipoic acid has a long history of use in diabetic neuropathy therapy at doses around 600 mg/day. Taken together, lipoamide and lipoic acid dissolve stress granules, return FUS to the nucleus in stressed cells, directly interact with FUS, and are low toxicity. As such, they are plausible to use as therapeutics.

Figure 2C:
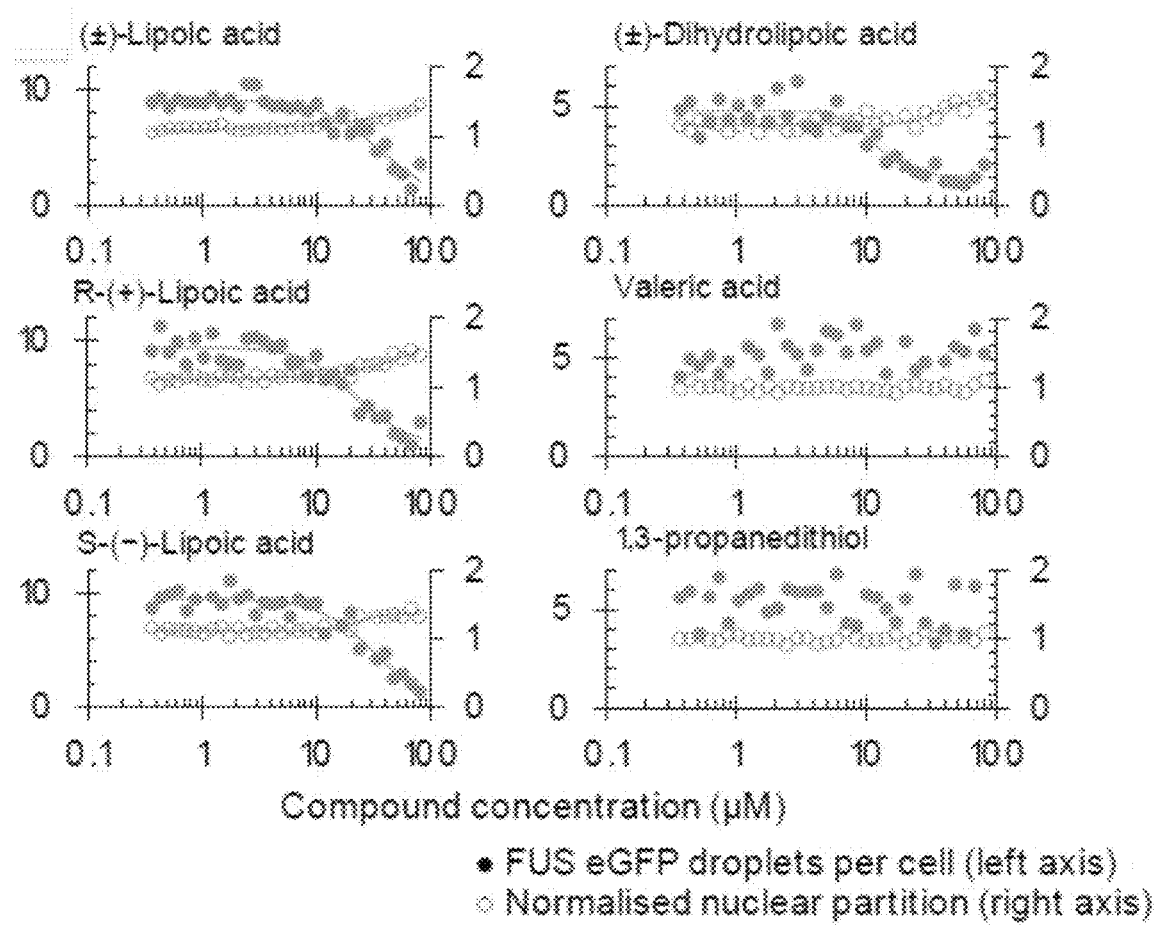

Lipoamide/Lipoic Acid Action Appears Independent of Enzymatic or Antioxidant Roles Activity of lipoamide in the follow-up in vitro screen (FIGS. 1D-1E) indicates it has direct effect on phase separation of a stress granule protein. Therefore, the inventors sought to exclude more mundane mechanisms such as stressor sequestration, enzymatic effects or antioxidant activity, for activity in the cell-based screen. The inventors tested this using lipoamide and lipoic acid-related compounds (FIGS. 2C-2D).

The screen was carried out with arsenate stress, which likely causes general oxidative damage, disrupts antioxidant responses by reacting with thiol groups and blocks the TCA cycle by reacting with the thiols in vital lipoyl moieties. To determine to what extent direct arsenate reaction with lipoic acid, antioxidant effects and enzymatic/glycolysis effects contribute to lipoic acid compound activity the dose dependent activity of (±)-lipoic acid, (±)-lipoamide, (±)-dihydrolipoic acid, 1,3-propanedithiol, and R-(+) and S-(−)-lipoic acid in HeLa cells expressing FUS-GFP was analyzed (FIGS. 2C-2D). All except 1,3-propanedithiol had comparable $EC_{50}$ reducing stress granule number following 1 h 1 mM arsenate stress.

This indicates lipoic acid is not active by supporting glycolysis, as free lipoamide is not a normal component of cell metabolism and should not be competent as a coenzyme/addition to an apoenzyme by lipoate-protein ligase. It also indicates lipoic acid is not directly acting as an antioxidant as the reduced (dihydrolipoic acid) form should be more active than the oxidized (lipoic acid), although could be supplementing a redox cycle involving dihydrolipoamide dehydrogenase (where only the naturally-occurring R-(+) isomer is likely to be active). We also note that menadione (pro-vitamin K and a classic antioxidant) did not reduce stress granule number in the primary HeLa cell screen. Arsenate reacts with thiols, so 1,3-propanedithiol and dihydrolipoic acid should be equally capable of direct chemical inactivation of arsenate stress, but 1,3-propanedithol had no effect up to 100 μM. Furthermore, the lipoic acid $EC_{50}$ indicates it would have to inactivate arsenate at a ~1:50 stoichiometry. Finally, any enzymatic role in the activity of lipoic acid, either as a lipoyl moiety supporting glycolysis or through antioxidant effects and recycling by dihydrolipoamide dehydrogenase, should be specific to the naturally occurring R-(+)-lipoic acid. However S-(−)-lipoic acid had very similar activity.

Together this indicates some other mechanism of action; perhaps a stress signalling mechanism or a direct affect on the physical chemistry of stress granule protein phase separation.

Lipoamide/Lipoic Acid Reverse Stress Granule Formation Caused by Several Types of Cellular Stress The cell-based screen was performed by pre-treating cells with compounds prior to arsenate stress, analyzing only FUS. To gain insight into the breadth of action of lipoamide and lipoic acid, and gain further insight into possible mechanism, their action on HeLa cells was comprehensively characterised.

Figure 3A:
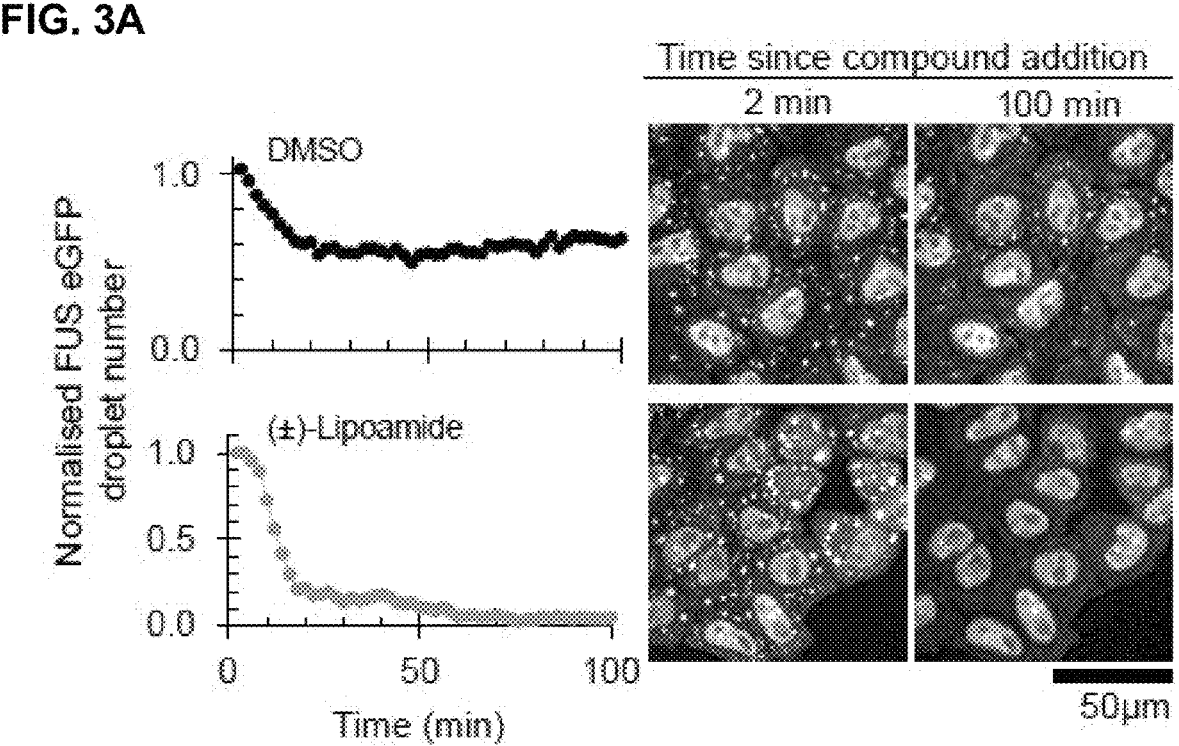
FIGS. 3A-3D show the pattern of effect of lipoamide and lipoic acid on different stresses under different regimes informs likely mechanisms of action.

To determine if lipoic acid can lead to dissolution of existing stress granules the inventors pre-stressed HeLa cells expressing FUS-GFP cells then treated them with lipoamide. Time-lapse microscopy showed addition of fresh medium with 10 μM lipoamide and 1 mM arsenate dissolved 80-90% of cytoplasmic FUS droplets within 20 minutes while fresh medium with 1 mM arsenate slightly reduced stress granule number (FIG. 3A). This response is likely too rapid to represent a transcription/translation response.

Figure 3B:
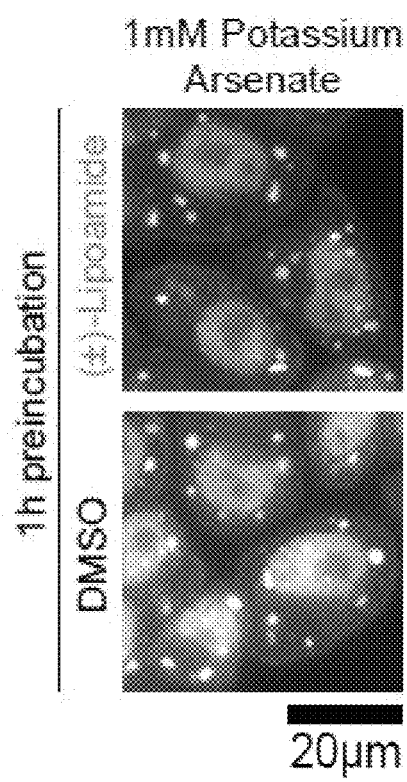

To test if treatment of cells with lipoamide can give a persistent resistance to stress granule formation in the absence of continued lipoamide treatment 1 h pre-treatment of HeLa cells with 10 μM lipoamide followed by 1 h arsenate stress without lipoamide was tested. This did not prevent stress granule formation, indicating no persistent lipoamide-induced cellular adaptation to resist stress (FIG. 3B).

Figure 3C:
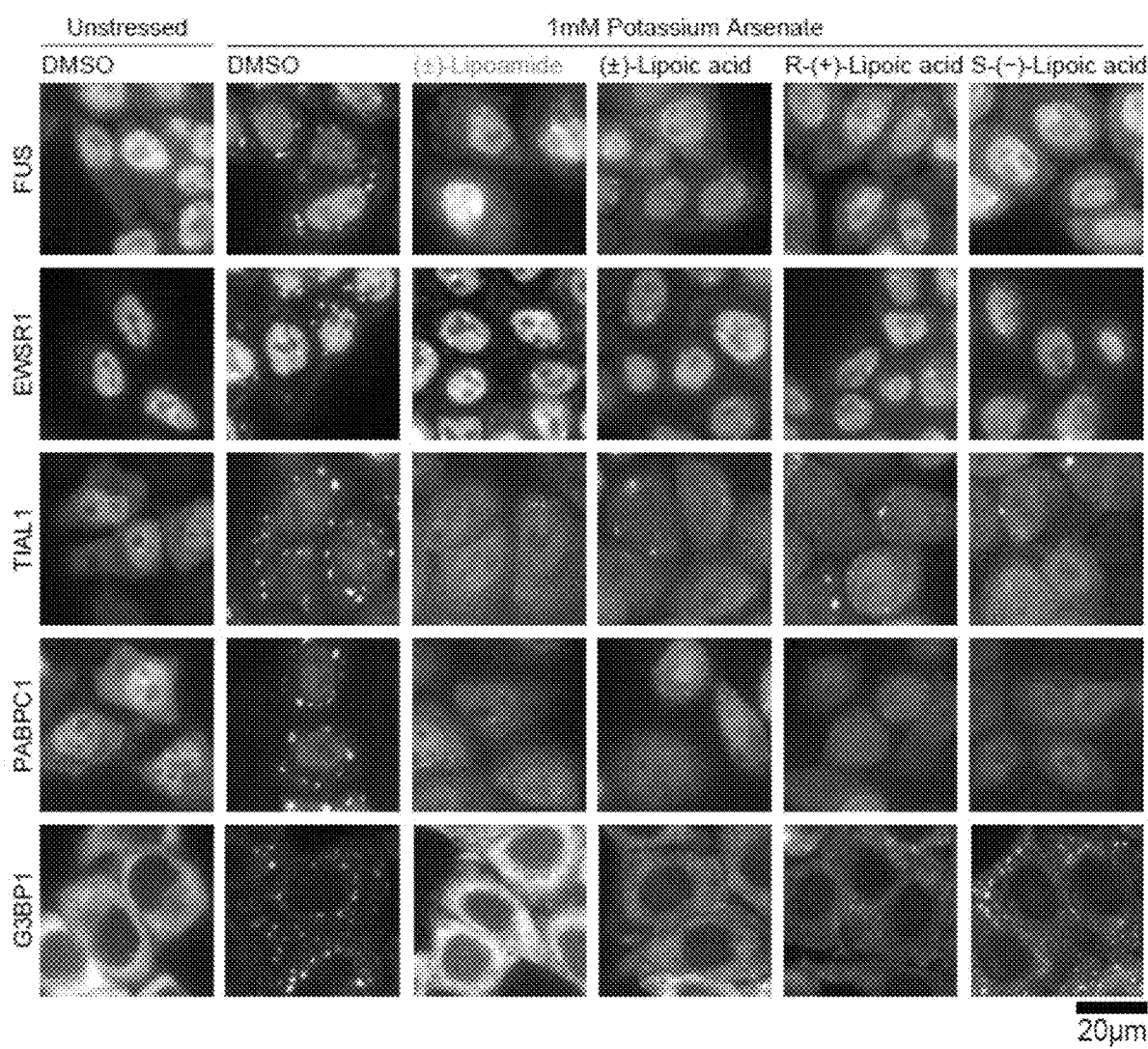

It was anticipated that a useful therapeutic would prevent all PLD-containing stress granule proteins from localising to stress granules. The inventors used 1 mM arsenate to stress a panel of HeLa cell lines expressing GFP fusions of stress granule proteins (EWSR1, TIAL1, PABPC1, G3BP1) with either no treatment or 10 μM lipoic acid or lipoamide. All proteins localised to stress granules in the absence of treatment, and not in the presence of racemic, S-(−)- or R-(+)-lipoic acid or lipoamide (FIG. 3C). As FUS is not required for stress granule formation this suggests FUS is not the only nor necessarily a primary target of lipoamide or lipoic acid in cells. Instead all LCD/RBP proteins are affected, and one vital for stress granule formation may be the target. This is a promising property for neurodegenerative disease therapy as many stress granule associated proteins are associated with different diseases and suggests a possible therapeutic effect on pathology arising from mutation of other stress granule proteins.

Figure 3D:
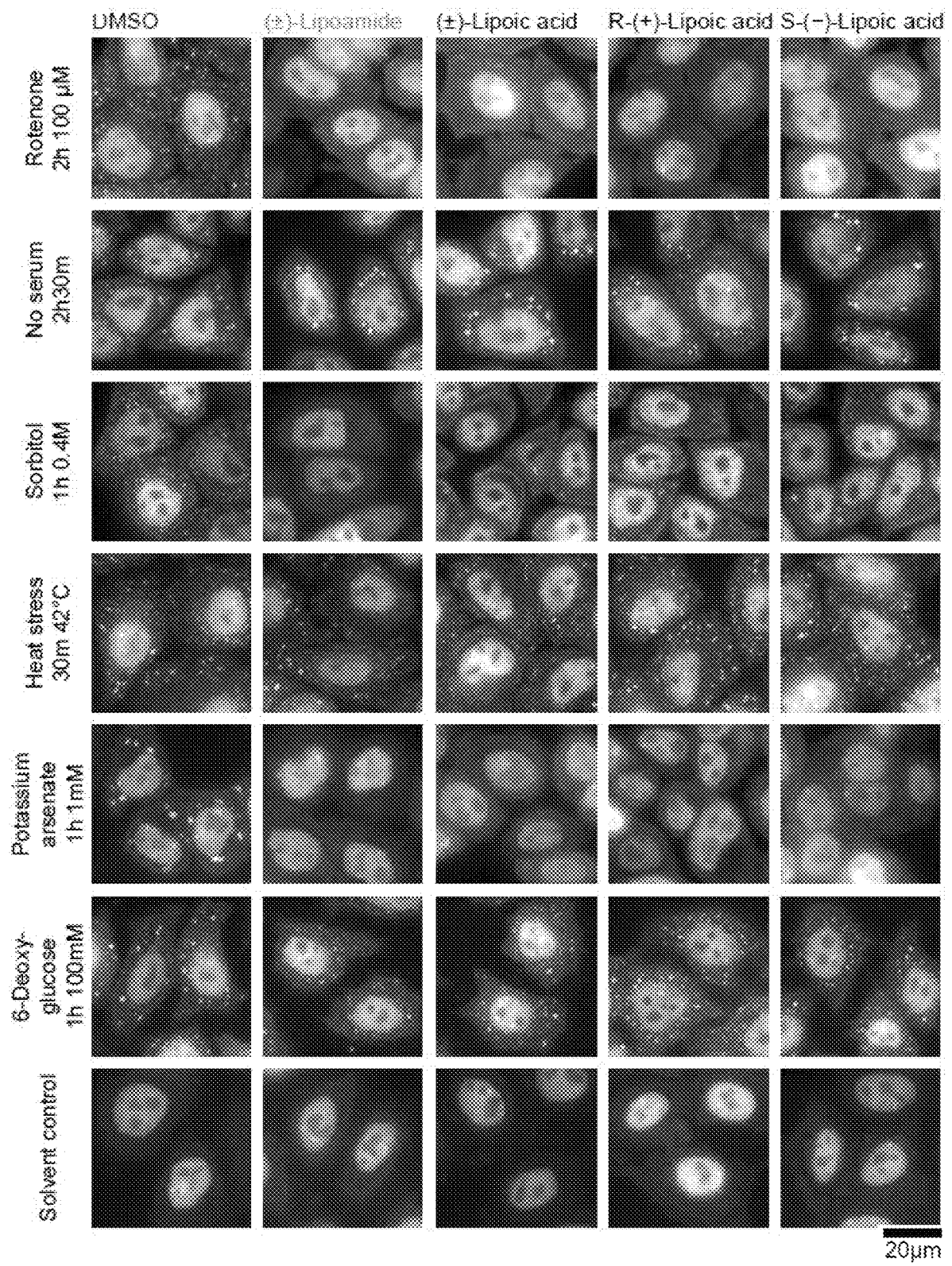

The stressor, arsenate, will react with the thiol groups of lipoamide. Therefore, to exclude the possibility that lipoamide is acting only by removing the stressor, so it was further tested whether lipoic acid can prevent stress granule formation triggered by other stresses than arsenate (an oxidative) stress: Mitochondrial electron transport chain inhibition (rotenone), heat stress (42° C.), hyperosmotic stress (sorbitol, a non-metabolisable sugar), glycolysis inhibition (6-deoxyglucose in the absence of glucose) or serum starvation. 10 μM racemic lipoamide or racemic, R-(+) or S-(−)-lipoic acid all reduced stress granule formation in HeLa cells with mitochondrial, hyperosmotic or arsenate stress (FIG. 3D). These compounds therefore do not affect stress granules formed following all stresses, but are not specific to arsenate stress.

Together, these data show lipoamide and lipoic acid completely inhibit stress granule formation under several stresses. Their pattern of action on different proteins and different stresses is consistent with compound action on phase separation of a vital LCD stress granule protein like TIA1 or a step in stress granule formation signalling shared by particular stresses.

Lipoamide does not Affect Other Cytoplasmic or Nuclear Liquid-Like Compartments

Stress granules are one of several, similar, cytoplasmic RNA-containing liquid-like compartments. Notably this also includes processing bodies (P-bodies). Several stress granule proteins also form nuclear bodies: nuclear paraspeckles, and foci at the sites of DNA damage. There are also many other nuclear liquid-like compartments. It was then asked whether lipoamide also affected these other bodies, using a panel of cell lines expressing GFP fusions. For this analysis, mitoxantrone was included as a representative of the heterotri-/tetracyclic compound class of hits (FIG. 1F). An overly-broad effect on liquid-like compartments would likely cause side-effects for a therapeutic.

Figure 4A:
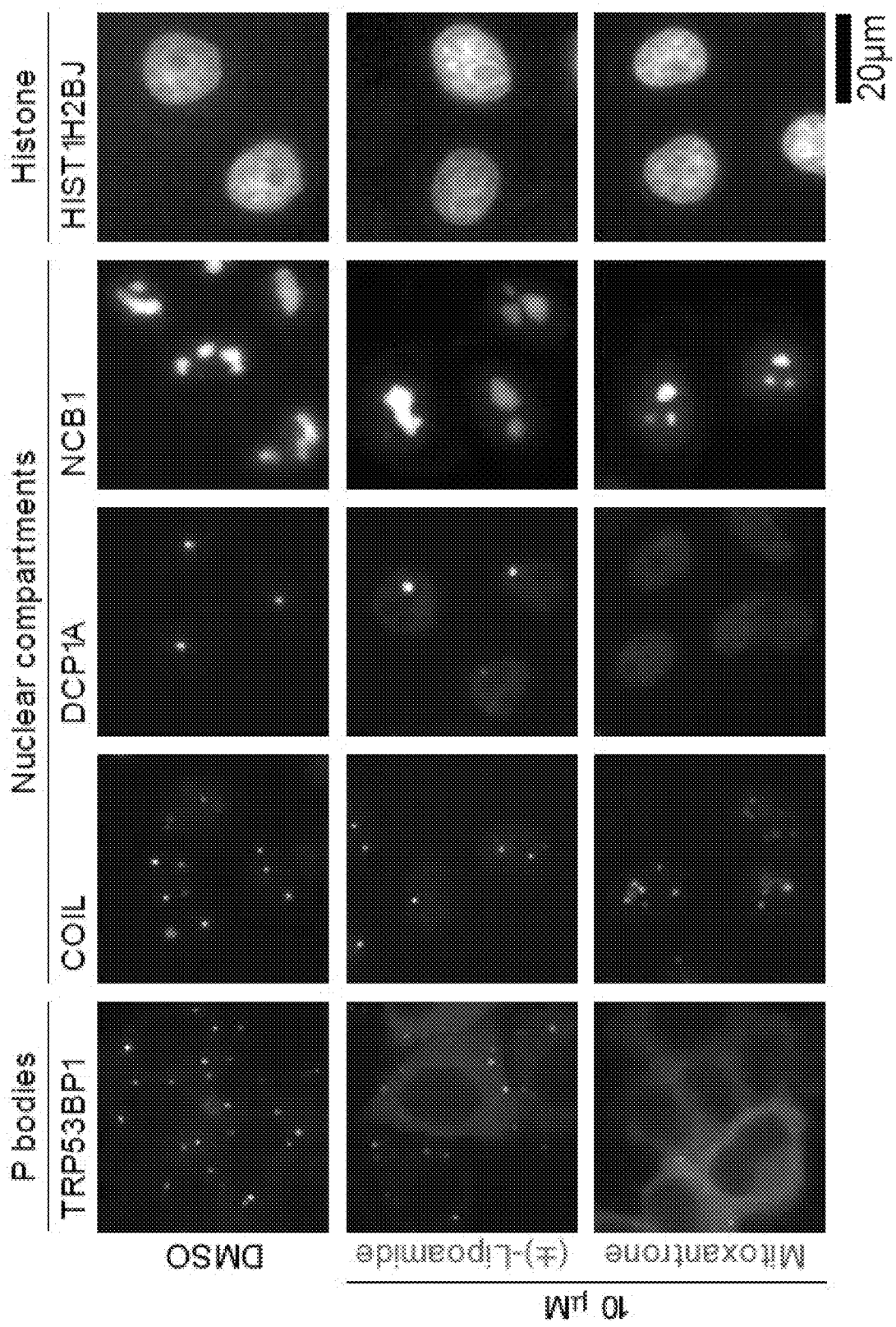
FIGS. 4A-4B show the lipoamide does not dissolve nuclear FUS compartments and other nuclear compartments.
Figure 4B:
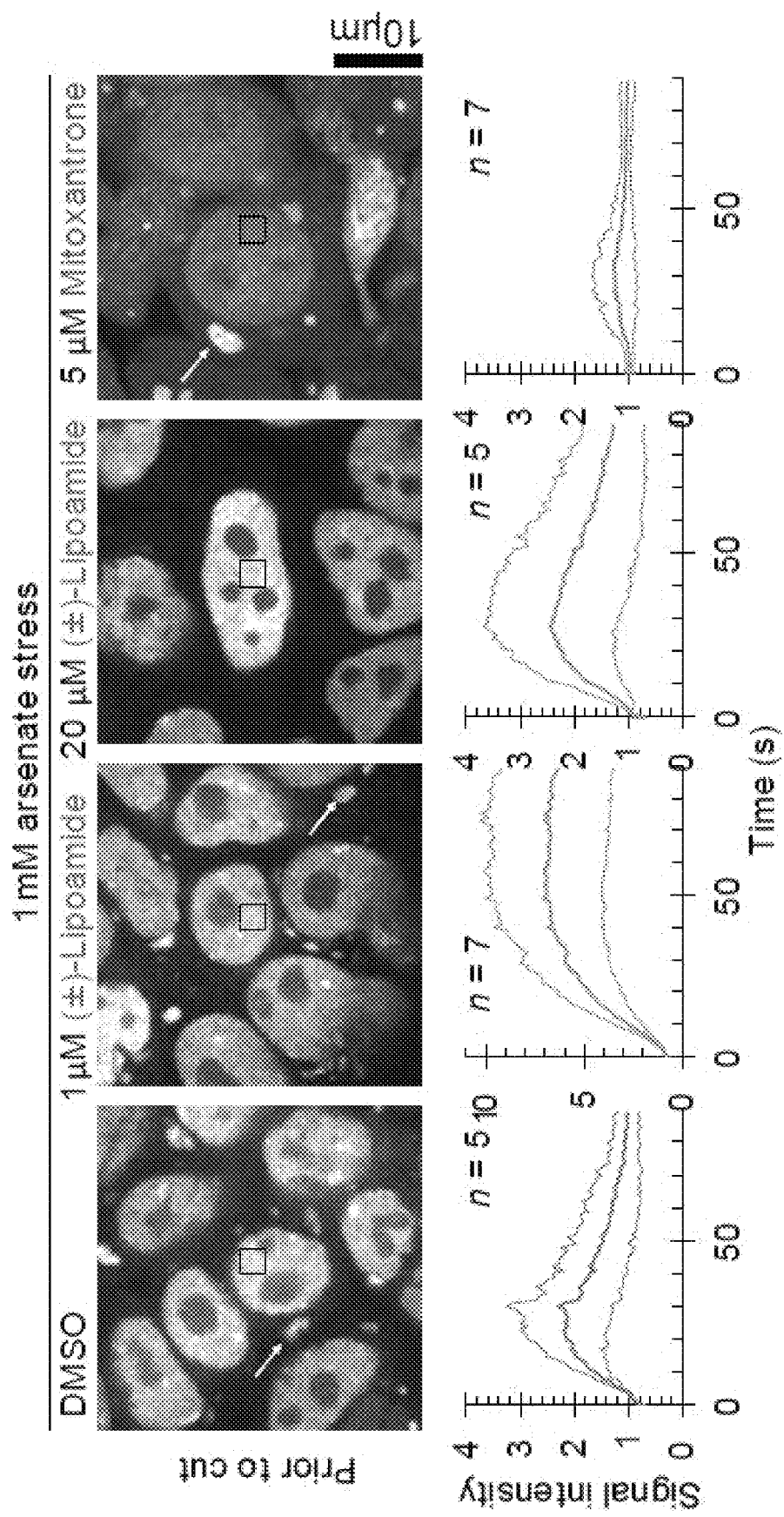

Lipoamide under conditions that would dissolve stress granules did not affect the localization of RNA processing body (P-body, cytoplasmic), PML bodies (nuclear) or DNA damage focus (nuclear) proteins (FIG. 4A). In contrast, mitoxantrone affected all of these compartments to some extent (FIG. 4B). The action of lipoamide is therefore specific to the signaling and/or physical chemistry driving stress granule formation, stress granule phase separation, and/or a specific signaling route. Stress granules normally form and dissolve rapidly in comparison to many other compartments.

FUS is recruited to sites of DNA damage, and a potential mechanism contributing to ALS pathogenesis is reduced DNA damage response due to sequestration of FUS in the cytoplasm in stress granules. Strong association of FUS nuclear localization (NLS) mutations (e.g., P525L) with familial ALS mutations supports this hypothesis. The inventors therefore tested whether lipoamide affect FUS recruitment to sites of DNA damage induced by focused UV laser irradiation site, using arsenate-stressed iPSCs expressing FUS GFP (FIG. 4B). 20 μM lipoamide (which dissolves stress granule) had no significant effect on FUS GFP recruitment to sites of DNA damage. 1 μM lipoamide (which did not affect stress granules), increased recruitment of FUS GFP to sites of DNA damage, likely to be beneficial. In contrast, mitoxantrone blocked recruitment of FUS GFP to sites of DNA damage, at concentrations which were not sufficient to dissolve cytoplasmic FUS droplets. The action of lipoamide is therefore specific to cytoplasmic FUS liquid-like compartments, a therapeutically useful feature.

Lipoamide/Lipoic Acid Directly Interact with FUS to Reduce Fibre Formation and Hardening The inventors selected lipoic acid and lipoamide for further characterization as lipoamide affected FUS droplet formation in vitro (FIGS. 1D-1E). It caused formation of larger droplets, similar to the effect of the surfactants in the library. This suggested more rapid Ostwald's ripening/coarsening, perhaps driven by increased surface tension. Continuing with FUS as a well-characterised phase-separating stress granule protein, we tested whether there were other effects of lipoic acid or lipoamide on phase separation in vitro.

Figure 5A:
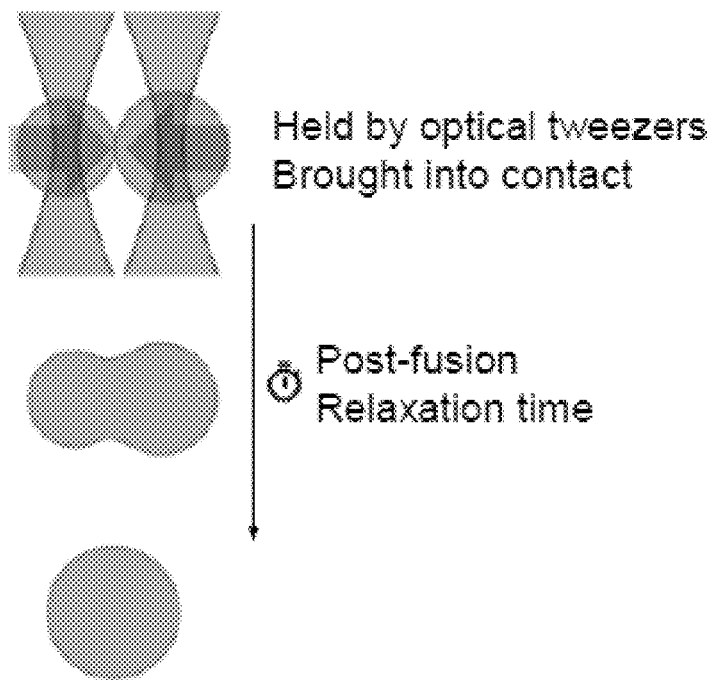
FIGS. 5A-5E show that lipoamide and lipoic acid affect FUS condensate properties and ALS-associated mutant FUS solidification in vitro.
Figure 5B:
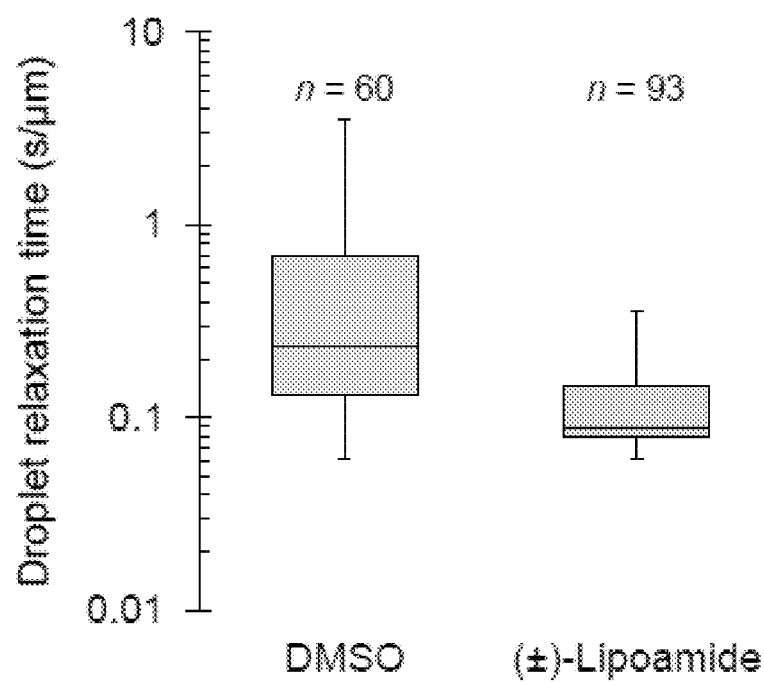
Figure 5C:
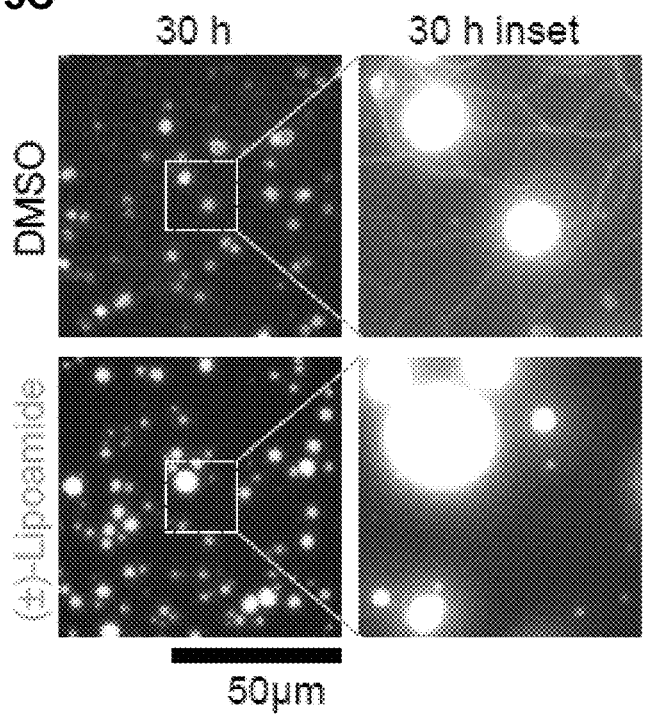
Figure 5D:
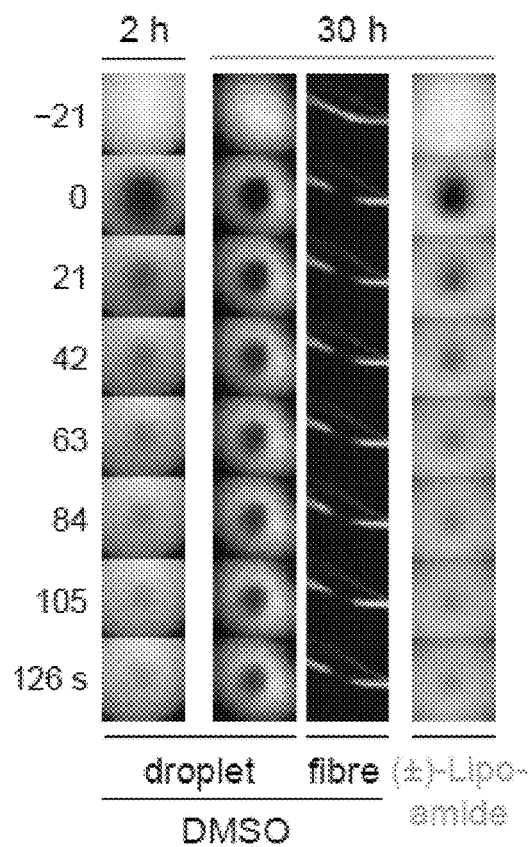
Figure 5E:
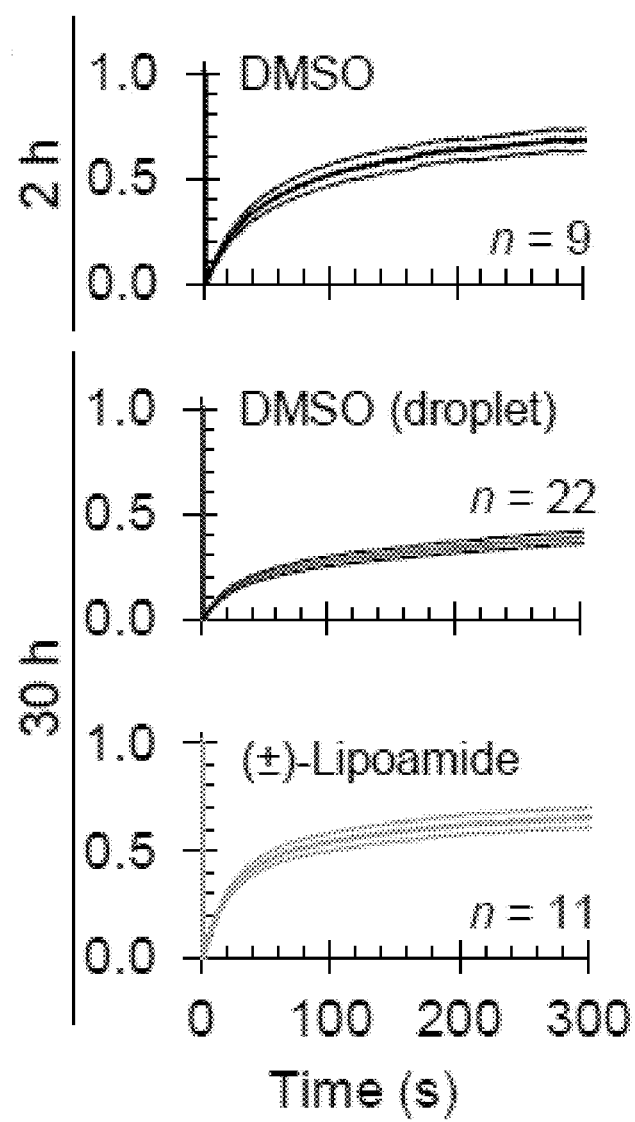

Lipoamide effect on FUS eGFP condensate liquidity (surface tension and viscosity) was determined. Here, condensate droplets were brought together by optical tweezers and the rate of fusion and relaxation to a sphere was measured (FIG. 5A). Lipoamide increased the liquidity by a factor of three (FIG. 5B). Together, the combined result of in vitro analyses suggests that the observed (FIG. 1E) increases in droplet size and number arise from faster generation of larger droplets, due to increased liquidity, followed by sedimentation of the larger droplets (see materials and methods for more details). As lipoamide/lipoic acid did not cause dissolution of FUS droplets in vitro we were able to examine the effect of lipoamide and lipoic acid on fibre formation and hardening, initially analysing FUS condensates formed under conditions of (dextran-induced) crowding (FIGS. 5C-5E).

Figure 6A:
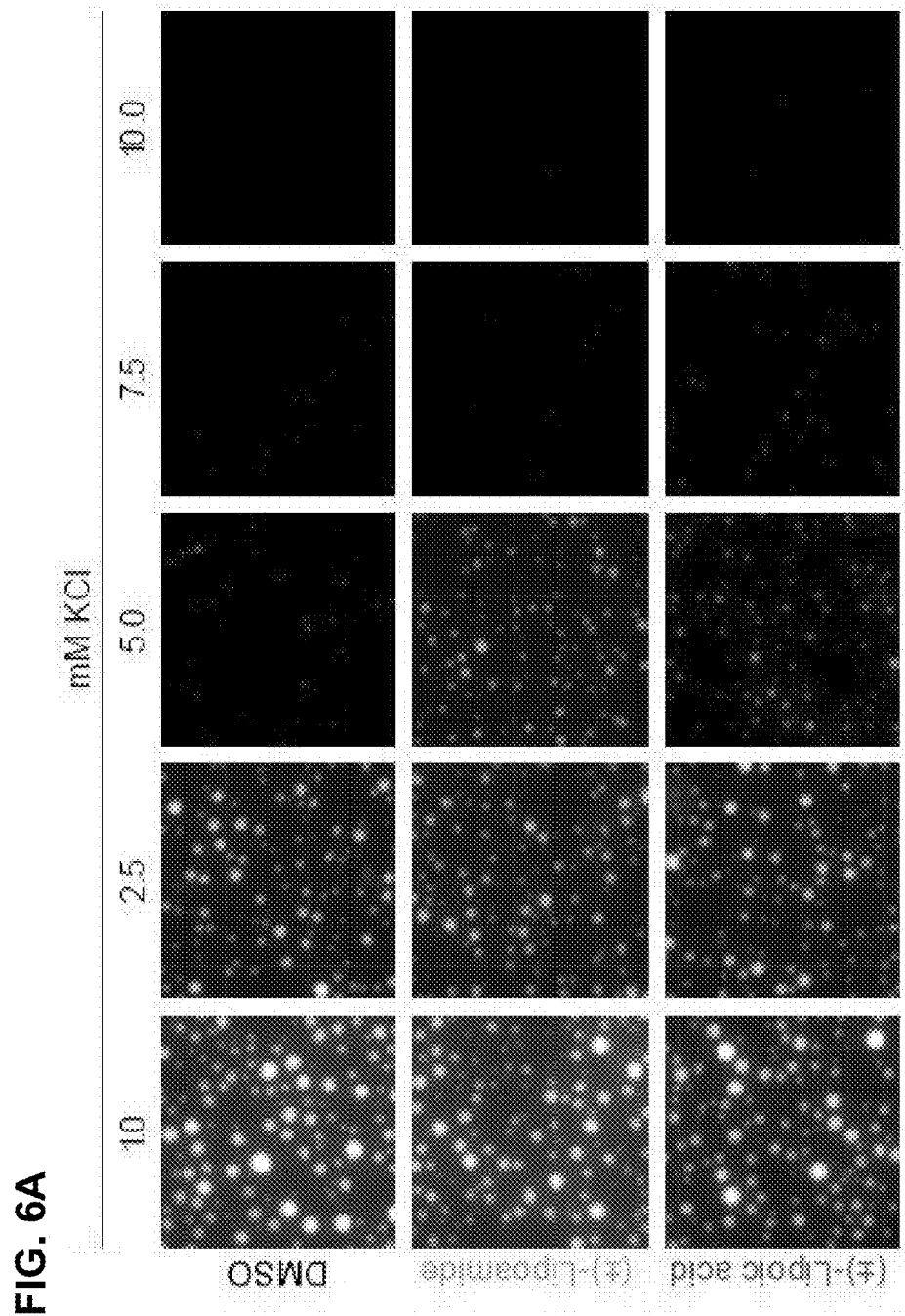
FIGS. 6A-6D show that lipoamide and lipoic acid directly alter FUS phase separation and FUS G156E solidification in vitro.

It was determined if lipoic acid or lipoamide affected the conditions under which FUS would phase separate in vitro. The inventors saw only a subtle effect of 100 µM lipoic acid or lipoamide, slightly increasing the minimum KCl concentration at which phase separation would occur (FIG. 6A). This suggests little to no effect of lipoic acid or lipoamide on the chemical potential of the system, which would give an altered phase diagram and equilibrium state. Instead the compounds affect coarsening which is a change in the kinetics of reaching the equilibrium state.

Figure 6B:
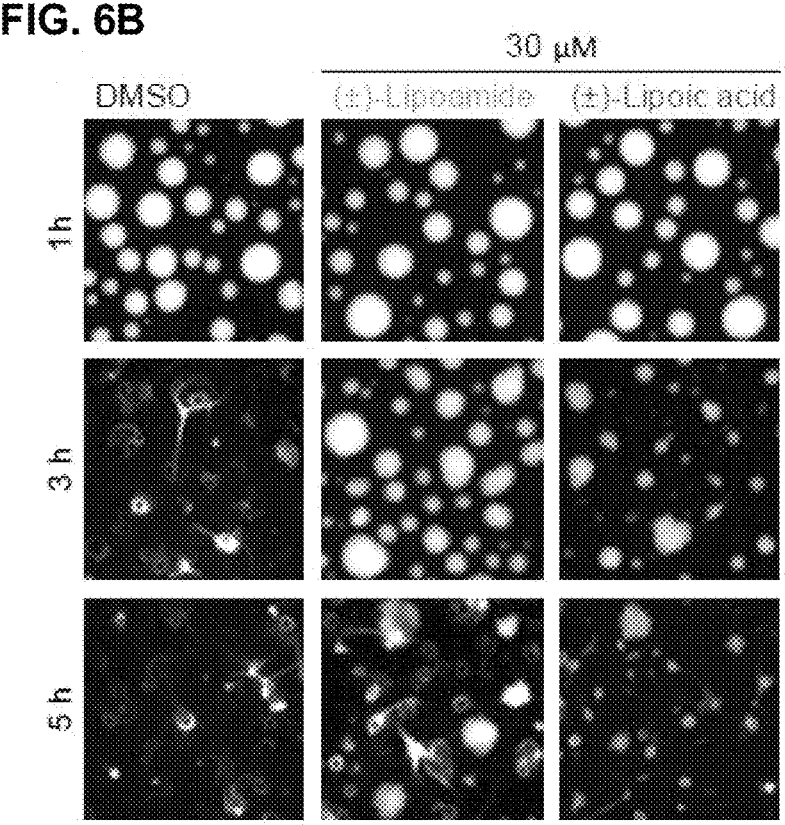
Figure 6C:
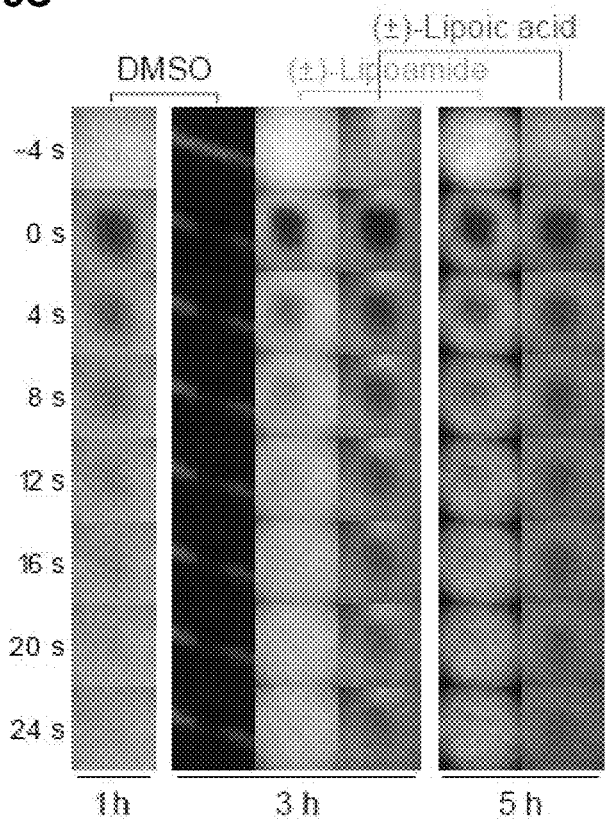

Therefore, hardening and fibre formation, another kinetic phenomenon, were analysed. In vitro FUS droplets 'age' over time, first hardening then tending to form amyloid/prion-like fibres. This is accelerated for G156E FUS, a mutation associated with familial ALS. 30 µM lipoic acid and lipoamide both delayed fibre formation of G156E FUS (FIG. 6B). Furthermore, both compounds delayed hardening of FUS droplets with droplets retaining large mobile fractions of FUS (FIG. 6C). This occurred in the presence of 1 mM DTT, a ~1:30 excess of a reducing agent, strongly suggesting a non-antioxidant mechanism of lipoic acid/lipoamide.

The prevention of hardening and more rapid coarsening indicates direct interaction of FUS to increase 'liquidity' at concentrations attained in cells. This may allow more ready dissolution of stress granules, and may reduce FUS (and other PLD-containing stress granule) aggregation in vivo. The inventors first tested this for iPSCs in vitro using a filter binding assay to detect insoluble FUS aggregates. This showed that lipoamide reduced the quantity of insoluble FUS, either wild-type or P525L, in arsenate-stressed cells (FIGS. 11B-11C).

The in vitro data identified that the mechanism of lipoamide action requires transient and weak interactions between the lipoamide and FUS within the granules are required. Capturing this interaction is a challenging prospect for the conventional tools of structural biology. For this mechanism to be relevant inside cells, it is necessary for lipoamide access the interior of the cells in an unmodified form, at sufficiently high concentrations to have an effect. Lipoamide and lipoic acid have physical effects on FUS, but required high quantities of compound relative to protein, for example 100 µM lipoamide with 2.8 µM FUS (FIG. 6A). As cytoplasmic FUS concentrations are low µM, an accumulation of compound must occur in the cells for this to be plausible: It must enter the cell, become concentrated, and not be metabolised. A signalling mechanism would not require any of these.

Finally, mechanistic detail was analyzed at the sub-molecular level by using NMR of the FUS prion-like N-terminal LCD to determine putative sites of lipoamide interaction. The LCD is able to phase separate to form condensates in vitro and the individual residues can be resolved and assigned in a $^1$H-$^{15}$N heteronuclear single quantum coherence spectrum. $^1$H-$^{15}$N analyses reveal a change in environment of individual residues as indicated by their corresponding chemical shifts. The magnitude of chemical shift changes were compared with and without both lipoamide or mitoxantrone. Whilst there were no single, clear sites of interaction of lipoamide with the FUS LCD mitoxantrone caused weak shifts across the LCD consistent with a weak interaction with tyrosine residues. This suggests lipoamide does not act by direct high affinity protein binding. This leaves several possibilities: Perhaps lipoamide interacts with the FUS LCD only when phase separated, potentially reducing viscosity, or interacts with the condensate phase boundary, perhaps increasing surface tension. Such interactions may reduce formation or expansion of aggregated forms of FUS involved in condensate hardening and reduced liquidity.

Lipoamide Becomes Greatly Concentrated in Cells

Figure 7A:
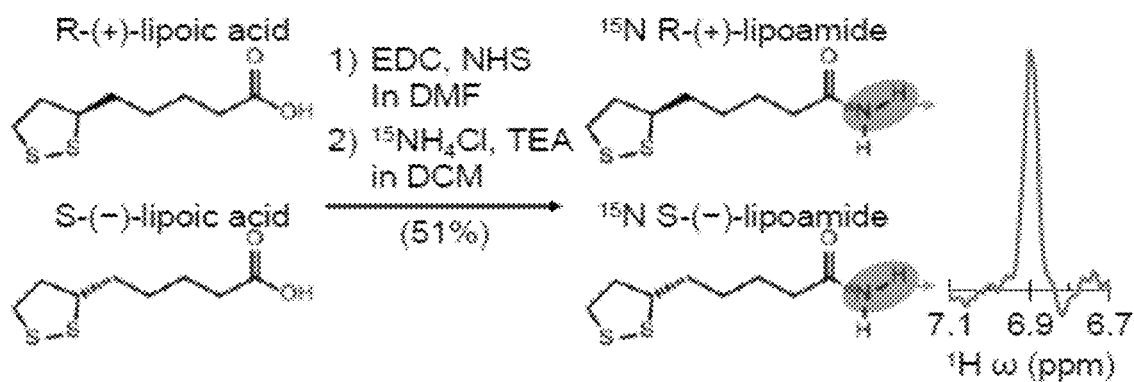
FIGS. 7A-7D show lipoamide accumulates to high concentrations in cells without being metabolised.

The concentration of lipoamide relative to protein required for an effect on condensate liquidity in vitro was higher than the $EC_{50}$ on cells, on the order of 100 µM lipoamide with 1 µM FUS (FIGS. 1D-1E, FIGS. 5A-5E). In cells, FUS concentrations are high for a protein (low µM)[41] and the cellular $EC_{50}$ was on the order of 10 µM (FIG. 2A, FIG. 3D). We also saw inverse effects of lipoamide on FUS-containing condensates in vitro (more, larger condensates) and in cells (fewer stress granules). To reconcile this difference and to understand the relevance of the effects in vitro in cells, we wanted to know the actual concentrations of compounds in cells. In principle, isotopic labelling allows direct monitoring of isotopically-labelled compounds even in complex environment through appropriate spectroscopy. To use this approach, $^{15}$N-labelled lipoamide (FIG. 7A) was synthesised. Solution state NMR experiments were then used to quantitatively detect the $NH_2$ protons covalently attached to $^{15}$N in cells to determine lipoamide concentration from the complex mixture inside cells, while also revealing any chemical modification of the amide group (manifesting as chemical shift changes or spectral alterations) (FIGS. 13A-13H).

Figure 7B:
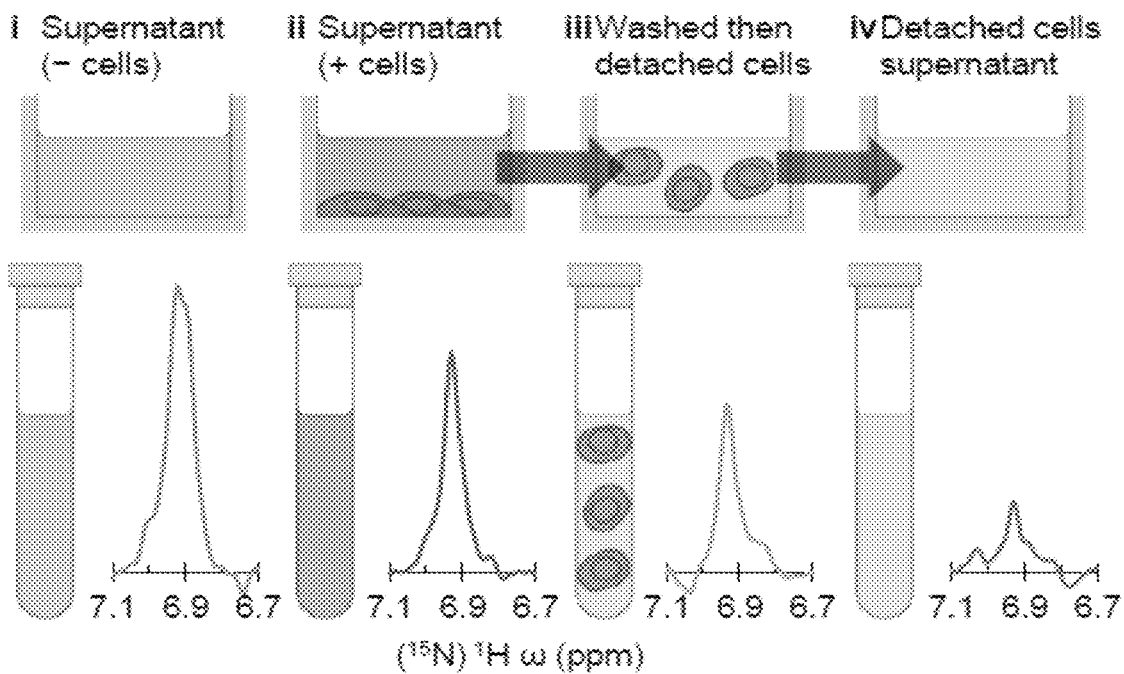
Figure 7C:
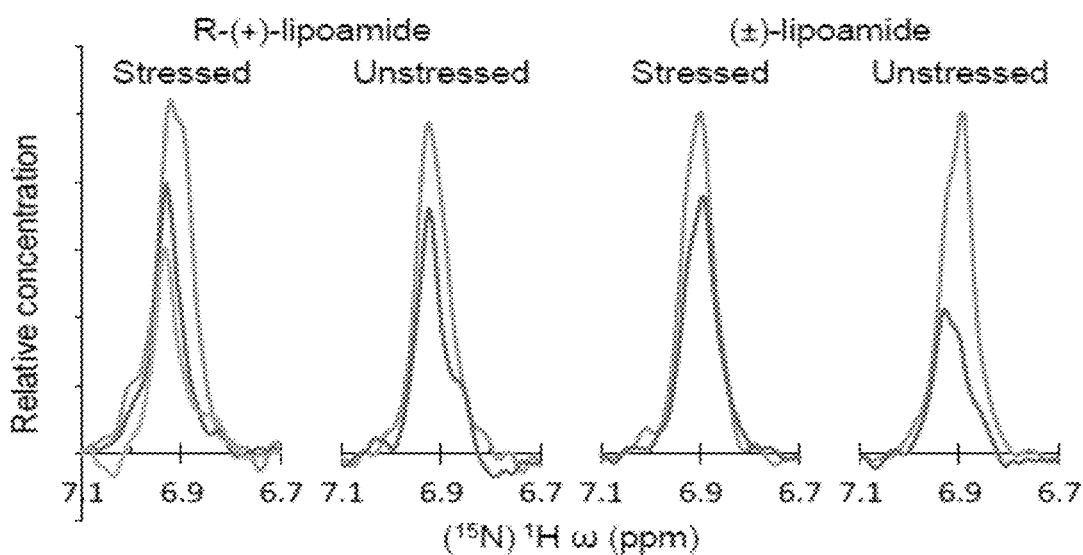
Figure 7D:
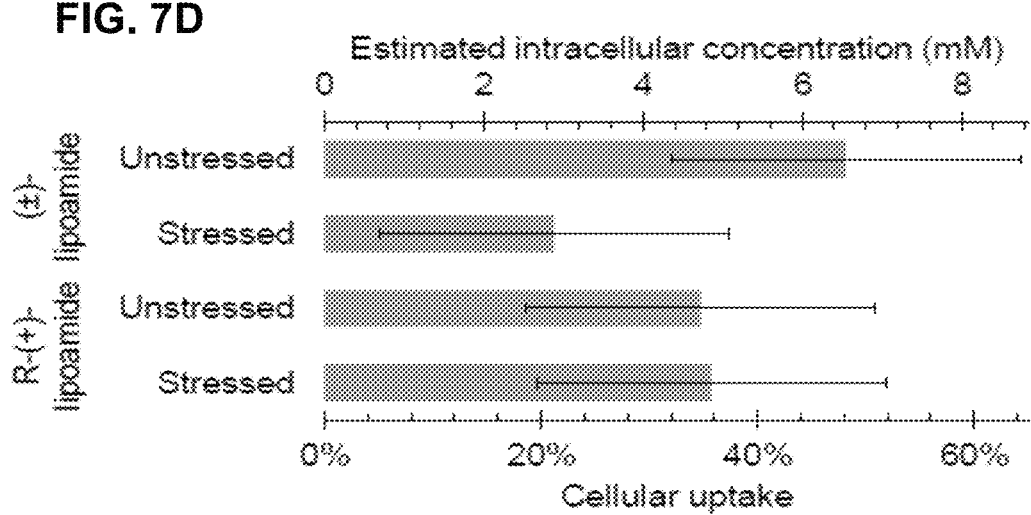

Uptake of $^{15}$N lipoamide by cells from the medium was quantified by NMR following incubation of lipoamide at 37° C. for 1 h either in the absence or presence of HeLa cells (FIG. 7B). Cellular uptake was determined by calculating the difference between medium incubated with cells or without cells for combinations of either R-(+) or (±)-lipoamide and either unstressed or stressed cells (FIG. 7C). For one sample, stressed cells with R-(+)-lipoamide, we confirmed that strong signal from the cell fraction was consistent with uptake of a large proportion of lipoamide (FIG. 7C). Both R-(+) and ±-lipoamide measurements indicated uptake of 35±11% (n=3 and 2, respectively) of the lipoamide present in the medium. No significant difference was observed either for uptake of R-(+) compared to (±)-lipoamide or stressed compared to unstressed cells (FIG. 7D).

There was no evidence for metabolism or any other chemical modification of lipoamides: the NMR signal from the cell sample indicated that lipoamide was present in an unmodified form in the cells (FIG. 7B).

Figures 13A, 13B, 13C:
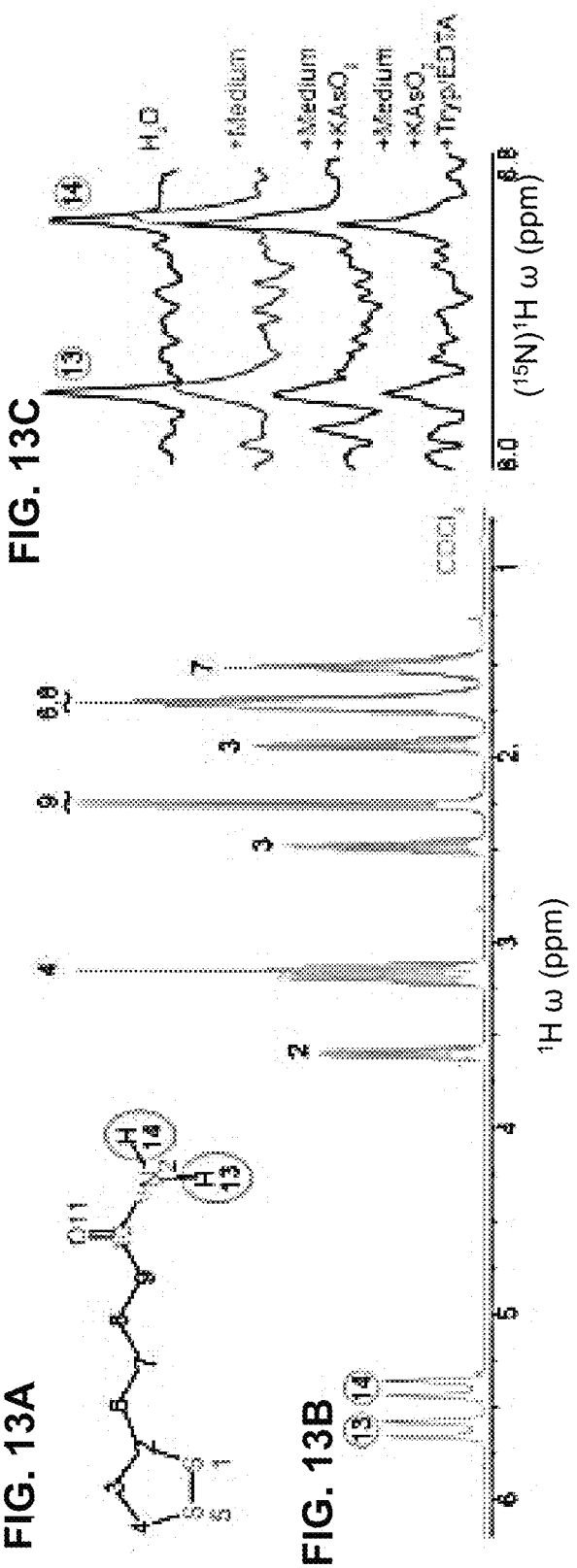
FIGS. 13A-13H show characterisation of $^{15}N$ Lipoamide by the $^1H$ NMR.
Figure 13F:
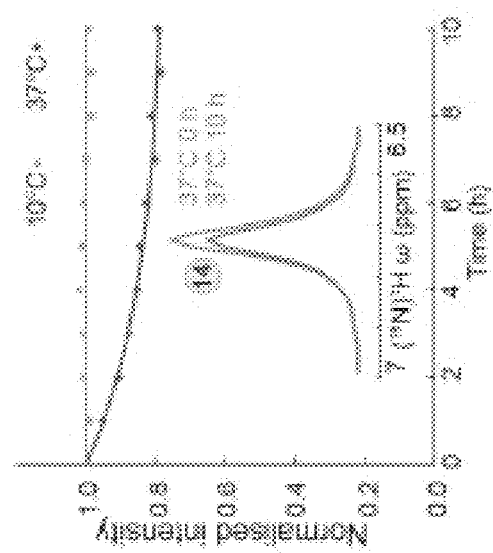
Figure 13E:
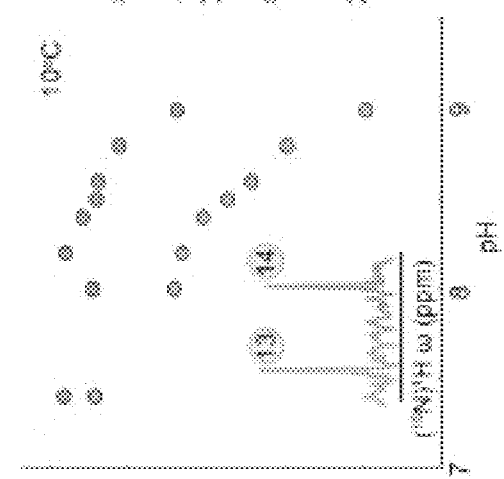
Figure 13D:
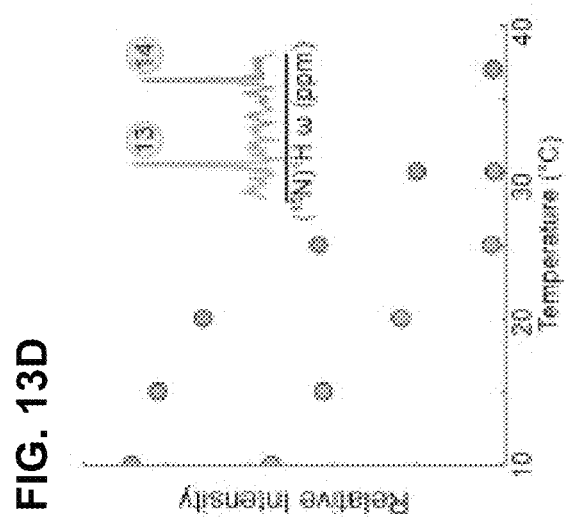
Figure 13G:
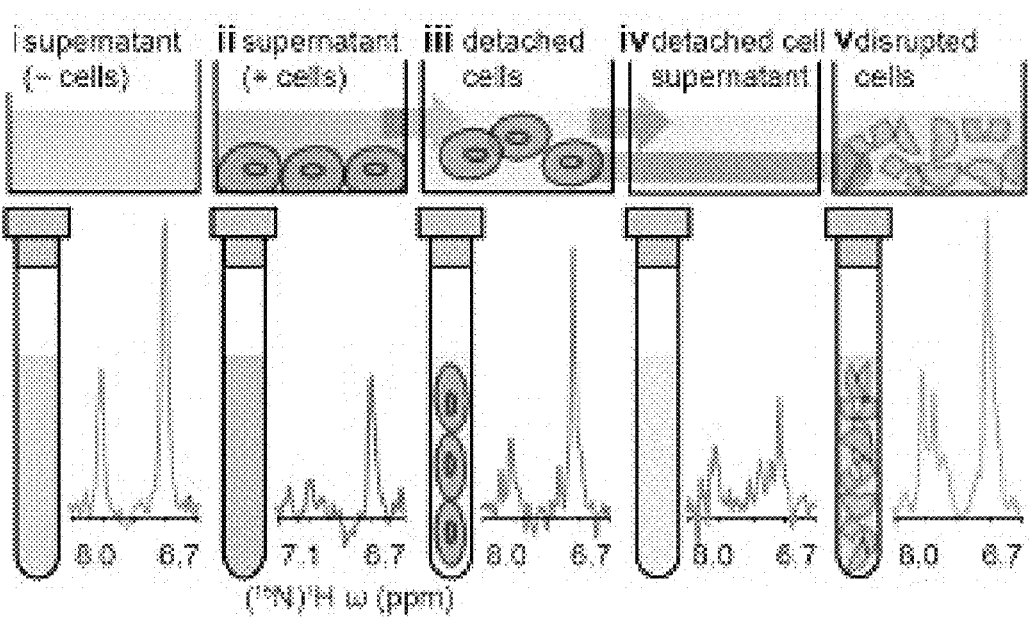
Figure 13H:
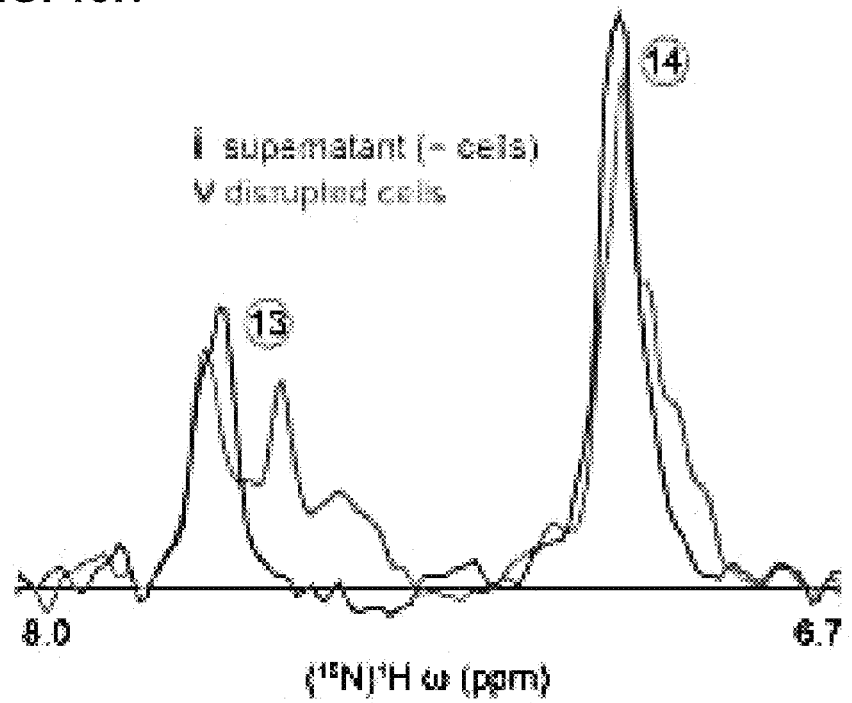

Approximate intracellular $^{15}$N lipoamide concentration can be calculated from percentage uptake, number of cells and their volume (Supplementary Methods)—these indicated an average intracellular concentration of 5.0±1.6 mM (FIG. 7D), markedly higher than that attained in vitro under optimal conditions of H$_2$O with 1% v/v DMSO. Therefore, lipoamide is readily taken up by HeLa cells (reaching concentrations comparable to abundant cellular metabolites. It is present in a chemically unmodified form (FIGS. 13G-13H). This concentration is one order of magnitude higher than those seen to affect FUS GFP condensates in vitro indicating a physicochemical effect in cells is plausible.

Lipoamide/Lipoic Acid Prevents Stress Granule Protein Aggregation In Vivo

Figure 11A:
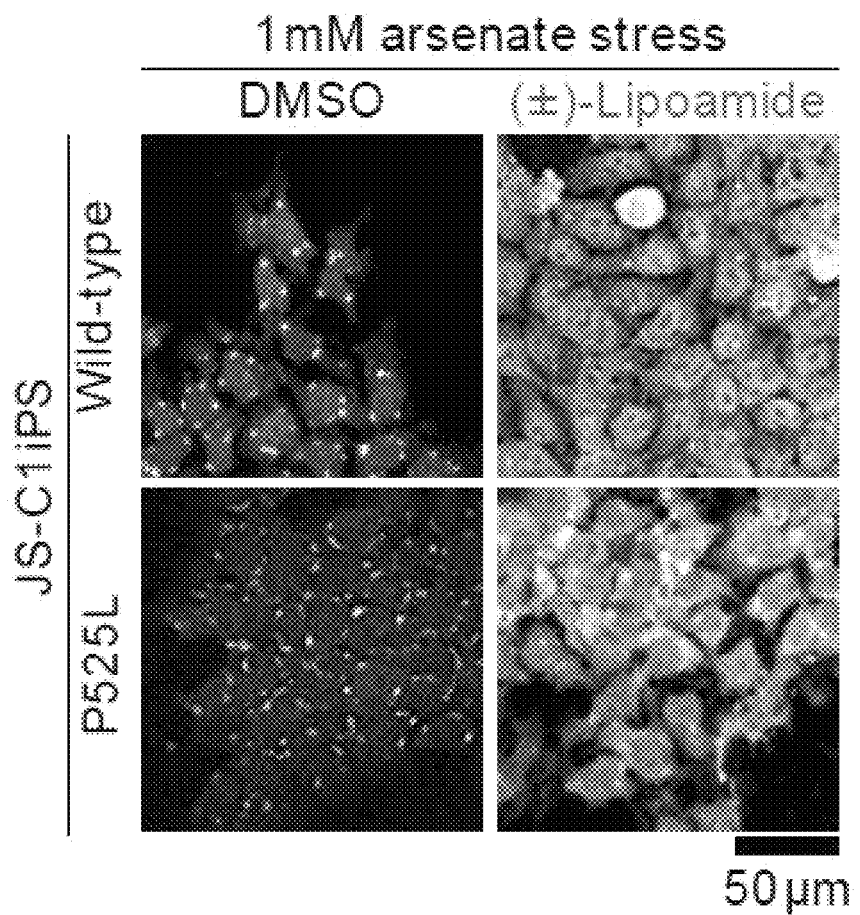
FIGS. 11A-11C show that lipoamide reduces wild-type and P525L FUS intracellular aggregates in iPS cells.
Figure 11B:
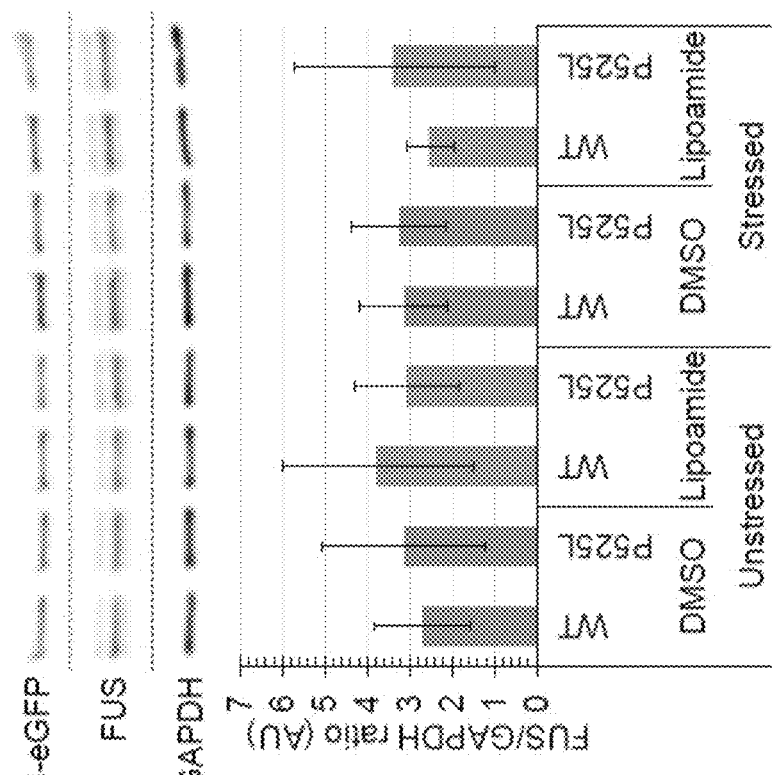
Figure 11C:
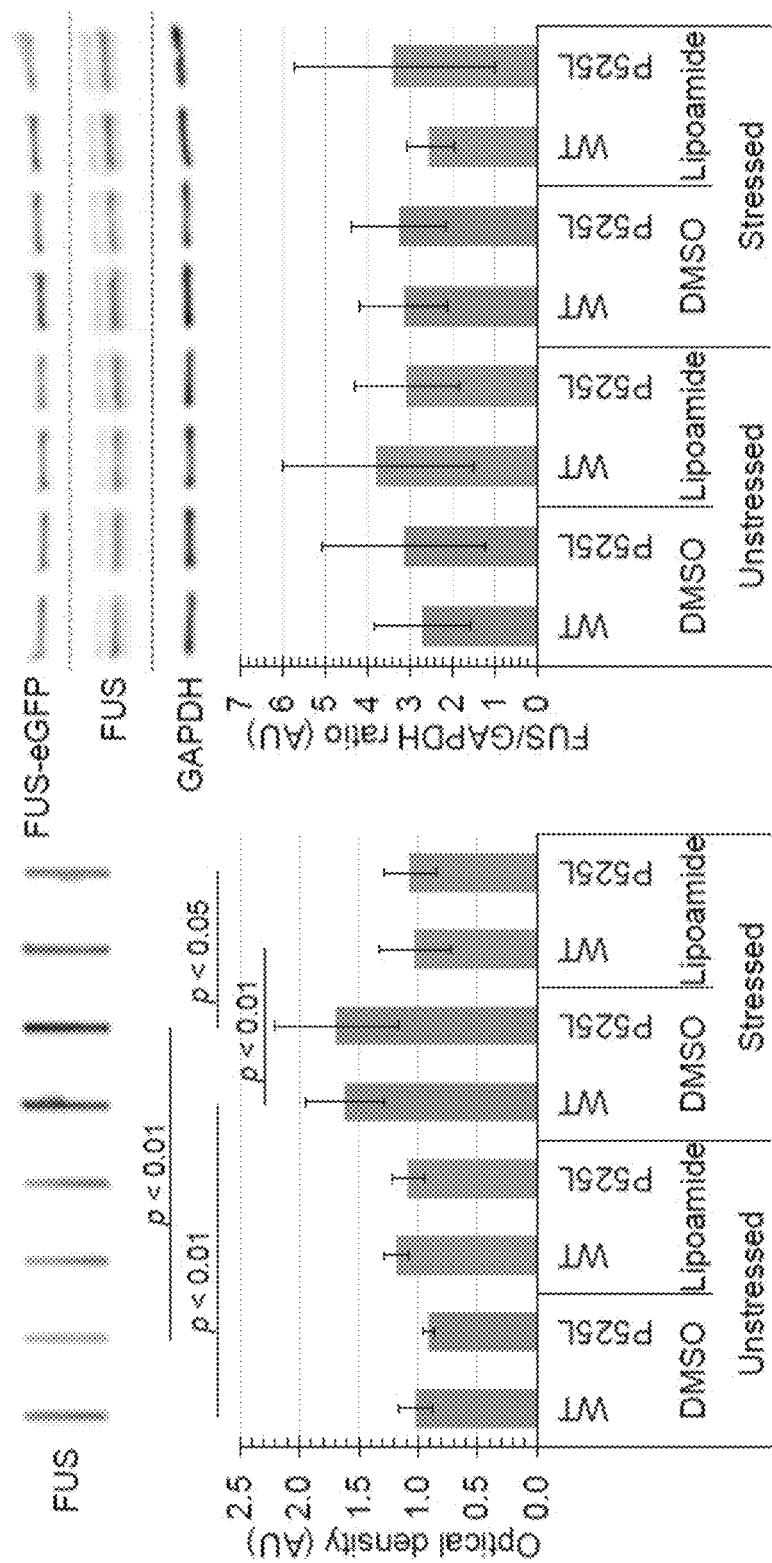

As lipoamide and lipoic acid had a large effect on FUS aggregation in vitro we used a filter-trap retention assay (in which aggregated protein from cell lysate tends to be retained on a membrane) to test whether lipoamide had a beneficial effect on spontaneous aggregation of wild-type or P525L FUS GFP in iPSCs (FIGS. 11A-11C). Both cell lines had evidence for some FUS aggregation, which was reduced following treatment with lipoamide (FIG. 11B).

Lipoic Acid Prevents Persistent Stress Granule/Aggregations In Vivo

To look for evidence of in vivo effects of lipoic acid on stress granule formation and protein aggregation the inventors turned to *Caenorhabditis elegans*. In *C. elegans*, ageing or chronic stress are associated with aggregation of stress granule proteins (including the orthologs of TIAL1 and PABC1). This likely has parallels with ALS pathogenesis. Therefore, it was tested whether lipoic acid prevents solidification of stress granules. *C. elegans* grown in liquid culture with R-(+) or S-(−)-lipoic acid all showed a dose-dependent decrease in the proportion of animals with aggregation of PAB-1, a stress granule protein with an LCD/RBP structure and the ortholog of PABC1. At the highest concentration tested (2 mM) there was some toxicity leading to 6 to 8% worm death. Testing of lipoamide was not possible due to precipitation in the worm culture medium.

To investigate whether the action of lipoic acid is specific to RBPs with an LCD, the aggregation of two globular proteins KIN-19 and RHO-1 was tested, which have been previously shown to aggregate with age in *C. elegans*. Neither protein has an RNA-binding domain or LCD. No effect of 1.5 mM lipoic acid on RHO-1 aggregation was found. There was a mild decrease in KIN-19 aggregation but higher toxicity of 1.5 mM lipoic acid.

Lipoic acid therefore can affect stress granule solidification on longer timespans on the timescale of an organism lifespan correlating with its behaviour on short time scales in vitro. The lipoic acid behaviour is consistent with direct interaction with stress granule proteins to reduce stress granule formation and/or stress granule protein aggregation.

Lipoic Acid and Lipoamide Recovers Neuron and Organism FUS-Associated Defects

Figure 8A:
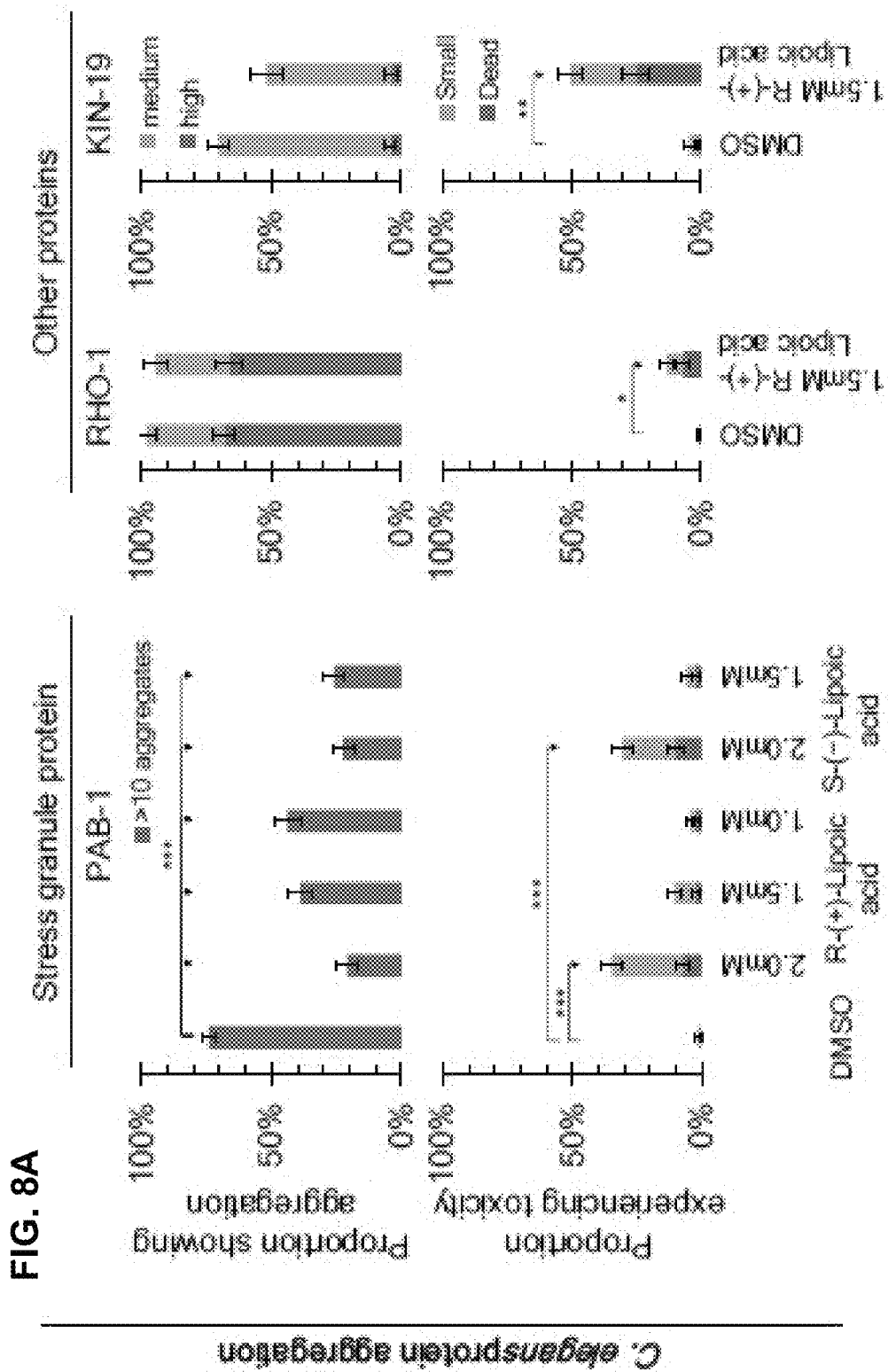
Figure 8E:
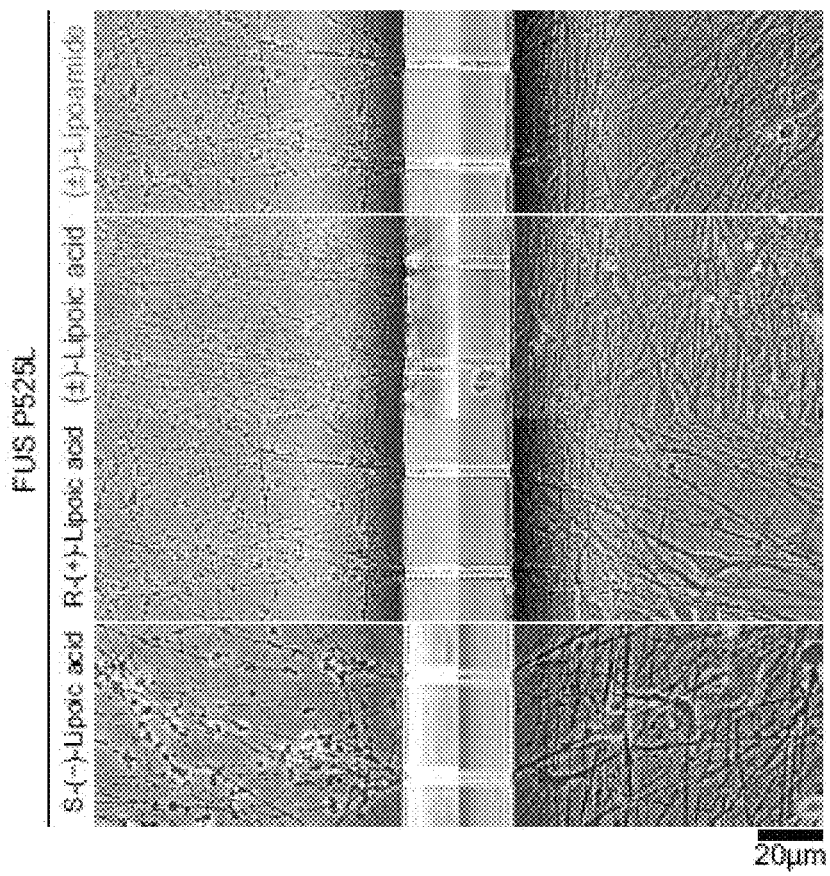
Figure 8F:
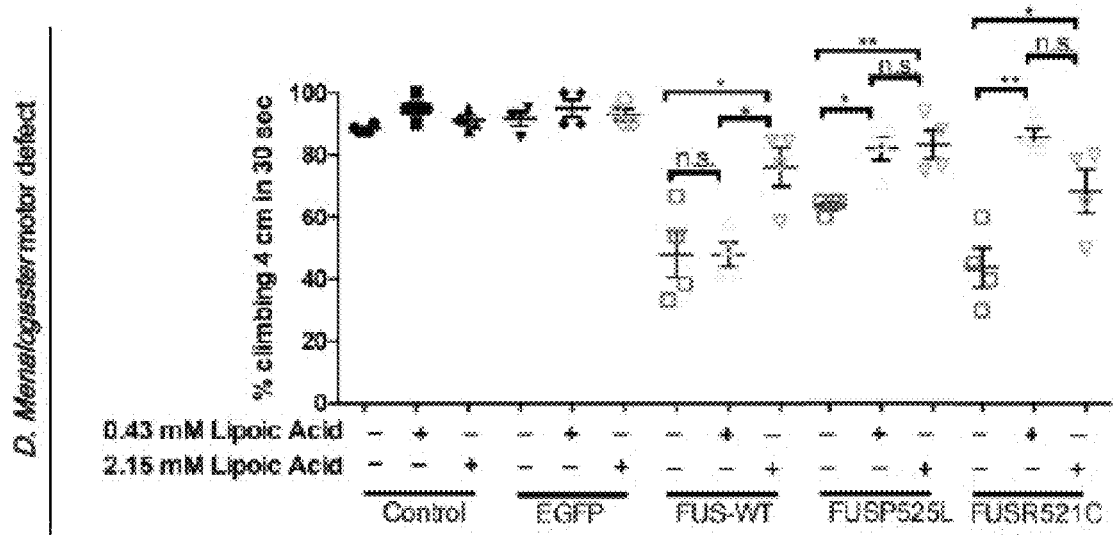
Figure 8G:
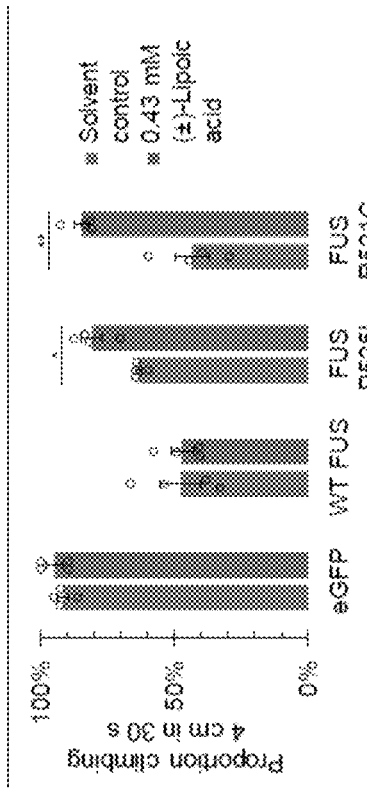
Figure 8H:
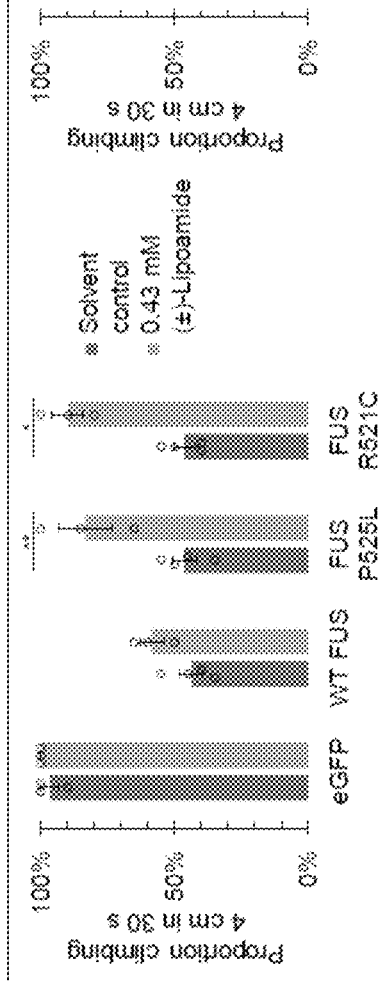
Figure 12B:
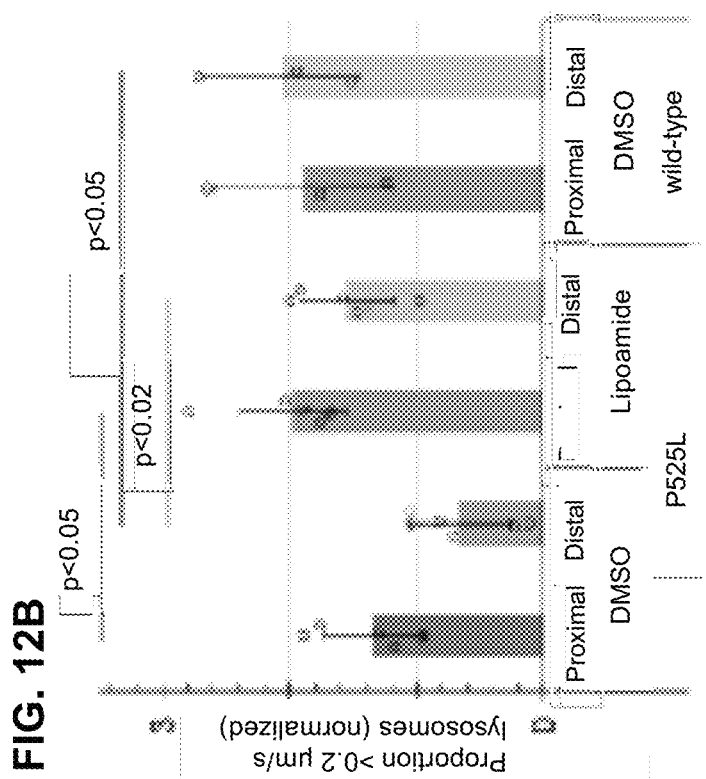
FIGS. 12A-12B show that lipoamide recovers axonal transport defects caused by expression of FUS P525L in motor neurons.
Figure 12A:
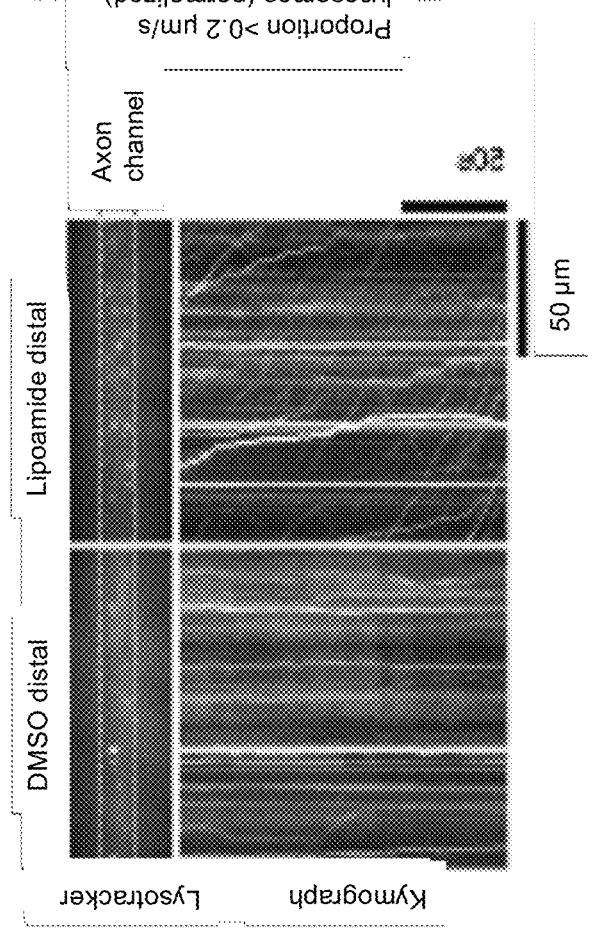

In humans, one cause of familial ALS is FUS mutation, particularly in the C terminal NLS. P525L is one such mutation, and iPSC-derived motor neurons (iPSC MNs) expressing P525L from ALS patients show defects consistent with motor neuron defects in the patient. iPSC MNs can be grown through silicone channels, positioning the soma on one side with the axons protruding through the channels to the far side. Such cultures can be maintained for long periods (>60 days). However, when expressing P525L FUS, the axons die back within this time period without exogenous cell stressors, although P525L FUS MNs have a greater propensity to form stress granules. This is similar to axon retraction leading to motor dysfunction in patients. Therefore whether lipoamide or lipoic acid was able to improve these phenotypes was tested. FUS P525L neurons initially appear morphologically normal (FIG. 8D, FIG. 9) but by 60 days in culture died-back axonal material has accumulated around the exit of neurons from the silicone channels (FIG. 8D, FIG. 9). Inclusion of 2 µM lipoic acid or lipoamide in the culture medium prevented such die back. It is thought defective axonal transport leads to axon dieback. To test this the inventors analysed transport of lysosomes within the axons of iPS MNs expressing P525L FUS with or without lipoamide in comparison to iPS MNs expressing WT FUS (FIGS. 12A-12B). Lipoamide recovered axonal transport in P525L FUS iPS MNs to the same level as WT neurons. In these assays the inventors have not used a treatment to induce formation of stress granules in the iPSC MNs, although in iPSCs P525L FUS has a greater propensity to form them (FIG. 8A). As no stressor is needed to induce axon die back, so it is suggested that lipoic acid either helps the iPSC MNs handle stochastic stress in culture or recovering an intrinsic defect caused by P525L.

It was further tested whether lipoic acid could have a similar beneficial effect on motor neurons in vivo using a fly model. *Drosophila melanogaster* has a FUS ortholog, cabeza, which is required for normal neuron development. Cabeza has a shorter N terminal PLD than FUS and expression of human FUS in *D. melanogaster* causes motor defects, including a reduced ability to climb. Expression of P525L or R521C human FUS (both of which are NLS mutants) causes even more severe motor defects. Food supplementation with lipoic acid recovered the motor defect in a dose-dependent manner, restoring the ability to climb 4 cm in 30 s from ~50% to >80%. This significant restoration of the flies' ability to climb. Lipoic acid is therefore capable of recovering motor neuron defects caused by FUS.

Discussion

Stress granules are implicated as a key site in ALS pathogenesis. They are formed by protein liquid-liquid phase separation, driven by multivalent weak interactions. This is unlike strong enzyme-substrate or protein-protein interactions typically targeted by drugs. Therefore, it was unclear whether it would be possible to identify drug-like compounds that interfere with phase separation, although conceptually plausible. The inventors searched for compounds that affected stress granule formation by direct interaction with LCD-containing stress granule proteins, focusing FUS as a well-characterised model protein. This approach identified lipoamide and the related compound lipoic acid. These compounds have a long and complex history as bioactive molecules and potential therapeutics for several conditions, but have no unambiguous mechanism of action. Here, it was shown that lipoamide can directly alter the properties of phase separated FUS droplets, reduce stress granule formation in cells, reduce aggregation of FUS in vitro and in cells, reduce aggregation of stress granule proteins in animals and recover phenotypes in neurons and animals arising from FUS mutants associated with familial ALS.

Figure 6D:
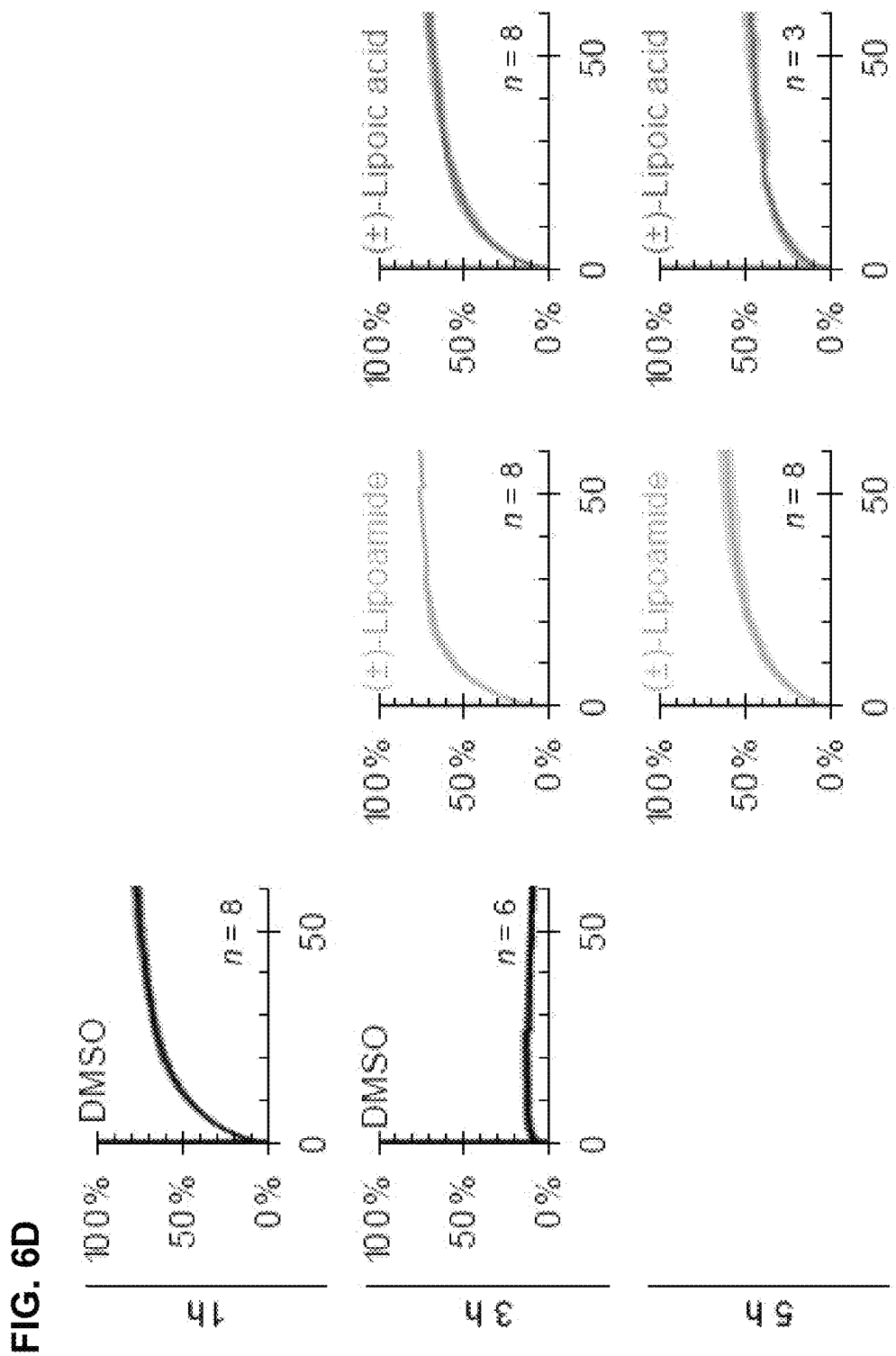

The investigations underlying the present invention were focused on lipoamide rather than lipoic acid, as the more potent hit in vitro. The evidences indicate a physicochemical mechanism of action is plausible. Lipoamide accumulates at high concentrations in cells, and at these concentrations (using FUS as a model in vitro) affects the liquidity of phase separated droplets. In cells lipoamide completely dissolves stress granules formed under some stresses (FIG. 3D), but not other non-membrane bound liquid like compartments—this includes compartments formed by the same proteins in different regions of the cell (nuclear paraspeckles and around sites of DNA damage) or formed by other proteins (P bodies, Cajal bodies and PML bodies) (FIGS. 4A-4B). Lipoamide also reduces solidification of these phase separated compartments, in vitro (FIGS. 6B-6D), in cells and seemingly in whole animals (FIG. 8A). Lipoamide affects FUS behaviour in vitro, but FUS is not required for stress granule formation in cells. It is therefore likely that lipoamide is also interacting with FUS-like proteins (other LCD/RBP containing proteins) in cells which are vital for stress granule formation. However, the precise nature of the interaction of FUS or other LCD-containing stress granule proteins remained unclear.

In cells, lipoamide caused dissolution of stress granules formed under several cellular stresses (FIGS. 3A-3D), while in vitro lipoamide did not cause dissolution of FUS condensate droplets (FIGS. 5A-5E), appearing to affect the kinetics rather than thermodynamics of FUS phase separation. One likely reason is that lipoamide accumulates to remarkably high concentrations in cells (FIGS. 7A-7D) where it is likely reduced but is not otherwise metabolised (FIGS. 13A-13H). The estimated cellular concentration (approximately 5 mM) is one order of magnitude higher than was able to be reach in vitro (300 µM), and much higher than the concentration necessary to increase the liquidity and reduce the hardening of phase separated FUS in vitro (FIGS. 5A-5E). It is possible that 5 mM lipoamide would dissolve FUS condensate droplets in vitro. There are also other potential explanations. Firstly, higher liquidity of stress granules could make them more sensitive to cellular stress granule dissolving factors. Secondly, that cells have stress granule, cytoplasm and nuclear environments, making it a more complex three phase system (perhaps related to the lipoamide effect on FUS nuclear/cytoplasm partition, FIGS. 2A-2D). Finally, lipoamide has a strong effect on the solidification of FUS (FIGS. 5A-5E), and this is thought to be driven in part by LCD-LCD interactions that are not required for phase separation in vitro. If LCD-LCD interactions are more important for phase separation inside cells then this may manifest as an increased sensitivity stress granules to lipoamide relative to FUS in vitro.

The cellular target of lipoamide or lipoic acid could not be unambiguously confirmed. While these compounds alter the properties of FUS condensates in vitro, FUS is not vital for stress granule formation. Therefore FUS cannot be the only cellular target. Many stress granule proteins are FUS-like with LCD domains and were affected in cells by treatment, including G3BP1, which is thought to nucleate stress granules (FIGS. 3A-3D).

Lipoamide and lipoic acid may be affecting a shared property of several FUS-like stress granule proteins or a key vital stress granule protein. If a physical chemistry mechanism is correct, it is theorized lipoamide modulates transient and weak interactions between FUS molecules to modulate condensate properties instead of having a single binding site. It is perhaps unsurprising that NMR was unable to detect an interaction despite a clear effect on the physical properties of FUS condensates in vitro (FIGS. 5A-5E, FIGS. 6A-6D). The caveats are that this assay concerned only the FUS LCD in the non-phase separated phase-lipoamide could interact with other regions of FUS such as the RNA binding domain absent in this assay.

The precise mechanisms of ALS pathogenesis are still unclear, but building on the hypothesis that stress granules are the crucible of ALS pathogenesis it is plausible lipoamide and lipoic acid would be potential therapeutics. The usefulness of lipoamide/lipoic acid depends on whether stress granule formation promotes ALS pathogenesis, or is part of a vital cellular response to stress. Similarly, whether stress granule protein aggregation is a means of sequestering a harmful protein, or whether it is intrinsically harmful. The inventors therefore characterized the potential of lipoamide and lipoic acid for treating ALS-like disease, primarily characterized lipoic acid as it has known pharmacokinetics and toxicology in humans, despite the slightly lower potency in vitro. It was shown lipoic acid reduces stress granule protein aggregation in C. elegans, a hallmark of aging in this organism, and a phenomenon with general similarity to aggregation of LCD-containing proteins in ALS pathology (FIG. 8A). The inventors also tested two models of ALS caused by mutations in FUS, and saw lipoic acid rescued defects in axon stability in neurons in vitro and motor control in D. melanogaster caused by expression of FUS mutants associated with ALS pathogenesis (FIG. 8C). Lipoic acid has previously shown some efficacy in SOD1 animal models of ALS and our work shows efficacy in models of stress granule protein-driven ALS pathogenesis through a novel mechanism of action. In people, a 600 mg daily dose of lipoic acid gives plasma concentrations of 8 to 30 µM, comparable to the concentrations used in our cell-based assays, meaning lipoic acid has surprising plausibility as a therapeutic.

Lipoic acid is a naturally occurring metabolite, and lipoamide is closely related. Despite being related to a naturally occurring metabolite, there was no evidence of metabolism of lipoamide. Both are viewed as antioxidants, indeed lipoamide has briefly been considered in prion-associated disease as an antioxidant, but activity was independent of lipoic acid redox state on cells, and lipoic acid and lipoamide were active in vitro in the presence of an excess of reducing agent. This suggests a non-enzymatic/non-metabolic and non-redox effect, leaving alteration of phase separation as a plausible mechanism; especially given lipoamide accumulates to high concentrations in cells. This is unlike, for example, prevention of stress granule formation by small molecule inhibition of eIF2α phosphorylation by ISRIB. Although the detailed mode of action is not clear, it is likely a different mode of action to 'traditional' compounds targeting a strong, specific, enzyme-substrate or protein-protein interaction.

In general terms, the success of the used screen shows that compounds can be found, which target the physical chemistry of proteins and demonstrates this overall screening approach is viable. This is important in diseases including ALS and others; many different LCD-containing proteins are implicated, and many different mutations are associated with familial ALS. It is not feasible to target each separately. Instead, compounds can be found which keep classes of protein in more liquid states or more soluble in the cytoplasm. This points to a new class of drug-those that affect the physical chemistry of a non-membrane bound compartment, or physicochemical drugs.

Stress granules form by phase separation of proteins within the cytoplasm and a few small molecules have previously been identified which modulate phase separation (notably 1,6-hexanediol), however lipoic acid and lipoamide have far more plausibility as a therapeutic. Concentrations of 1,6-hexanediol between 1 to 10% (several hundred mM) are required for in vitro or cellular activity, and this is rapidly toxic. The molecules we identified in our screen (both heterotri- and tetracyclic compounds and lipoamide and related compounds) were active in vitro (FIGS. 1A-1G, and 5A-5E) and on cells (FIGS. 1A-1G, 2A-2D, and 10A-10C) at vastly lower concentrations (tens to hundreds of µM), three to four orders of magnitude lower than 1,6-hexanediol. The effect of lipoamide on stress granules is also specific, in the sense that lipoamide did not affect other membraneless liquid like compartments in cells—it did not affect nuclear compartments formed by FUS (FIG. 4B) or formed by other proteins either in the cytoplasm or nucleus (FIG. 4A) and was well-tolerated by HeLa, iPS and motor neuron cells in culture.

As an aside, the anti-cancer drug mitoxantrone was potent at disrupting many non-membrane bound compartments. Mitoxantrone induces DNA damage, ascribed to a role as a topoisomerase inhibitor through DNA binding, however it seemed to disrupt rather than increase numbers of non-membrane bound DNA damage repose compartments-perhaps a physicochemical mechanism also contributes here.

It is interesting that lipoic acid is a natural metabolite. Recent data has identified another metabolite, ATP, as a hydrotropes with property of keeping proteins soluble. Perhaps the solution to preventing aberrant protein aggregation in disease compartments is to support the cell's ability to maintain a dissolving environment. Future screens may identify more such molecules.

Methods

Stable Kyoto HeLa BAC cell lines expressing proteins with a C-terminal GFP fluorescent marker were generated using BAC recombineering. This gives near-endogenous expression level of the fusion protein. In these lines, GFP is part of a modified localisation and affinity purification (LAP) tag, providing a short linker. HeLa cells were grown in high glucose DMEM supplemented with 10% FCS. Cultures were supplemented with 1% penicillin-streptomycin, and maintained under Geneticin (Gibco, 400 µg/ml) selection at 37° C. with 5% $CO_2$.

Human iPS cells lines, derived from three different donors, expressing FUS with a C-terminal GFP fluorescent marker were used. All were generated using CRISPR/Cas9 assisted tagging and mutagenesis and have been previously described. In summary: JS-SL-C1 iPS cells expressing either wild-type or P525L FUS GFP were previously generated from a healthy female donor. JS-SL-C1 iPS cells were used for compound dose response analysis. KOLF iPS cell lines expressing wild-type FUS GFP or P525L FUS GFP were previously generated from the KOLF-C1 clonal iPS cell line produced as part of the human induced pluripotent stem cell initiative (HipSci). KOLF-C1 cells were derived from a healthy male donor. In these lines, GFP is part of a modified localisation and affinity purification (LAP) tag, providing a short linker and giving an identical fusion protein sequence to the Koyoto HeLa BAC cell line. JS-SL-C1 and KOLF-C1 iPS cell lines were used as an isogenic pair for analysis of DNA damage response and lipoamide action on P525L FUS. AH-ALS1-F58 iPS cell expressing P525L FUS with a C-terminal GFP fluorescent marker were previously generated from a clonal iPS cell line from a female ALS patient expressing P521C FUS. The P525L mutation and GFP tag were introduced and the P521C mutation corrected by simultaneous tagging and mutagenesis. iPS cells were grown in TeSR E8 medium (Stem Cell Technologies) at 37° C. with 5% $CO_2$.

MNs were generated from AH-ALS1-F58 iPS cells expressing P525L FUS in matrigel coated plates with silicone channels for axons by inducing differentiation as previously described. This yields clusters of soma on one side of the channels with axons which extend through the channels and protrude out of the far side of the channels. AH-ALS1-F58 were used to generate motor neurons (MNs) as they have previously been characterised in axonal transport assays. iPS MNs used for assays within 4 weeks of the completion of differentiation, unless otherwise stated.

All procedures using human cell samples were in accordance with the Helsinki convention and approved by the Ethical Committee of the Technische Universität Dresden (EK45022009, EK393122012).

Recombinant Protein

For in vitro droplet formation screening and solidification assays recombinant GFP FUS and GFP G156E FUS were purified using baculovirus/insect cell expression system, exactly as previously described[7]. Briefly, His MBP FUS GFP was purified from cell lysate by Ni-NTA affinity purification, the His MBP cleaved, then concentrated by dialysis and further purified by size exclusion chromatography. The composition of the storage buffer for purified FUS was 1M KCl, 50 mM Tris HCl pH 7.4, 5% glycerol and 1 mM DTT, and FUS concentration was adjusted to 30 µM in storage buffer prior to use.

Compounds

For ex vivo and in vitro screens the PHARMAKON 1600 library was used, prepared as 10 mM stocks in DMSO. For follow-up assays, compounds were repurchased and prepared as 10 mM stocks in DMSO; lipoamide (T5875, Sigma Aldrich or sc-239160, Santa Cruz Biotechnology), lipoic acid (62320, Sigma Aldrich), R-(+)-lipoic acid (07039, Sigma Aldrich), S-(−)-lipoic acid (08561, Sigma Aldrich), dihydrolipoic acid (T8260, Sigma Aldrich), valeric acid (240370, Sigma Aldrich), 1,3-propanedithiol (P50609, Sigma Aldrich), mitoxantrone (M6545, Sigma Aldrich), N-(2-hydroxyethyl)ethylenediamine (127582, Sigma Aldrich), 1,4-dihydroxyanthraquinone (Q906, Sigma Aldrich), cetylpyridinium chloride (C9002, Sigma Aldrich), quinacrine (Q3251, Sigma Aldrich), 9-aminoacridine (A38401, Sigma Aldrich), 2-amino-5-diethylaminopentane (A48806, Sigma Aldrich), daunorubicin (30450, Sigma Aldrich), 8-acetyl-6,11-dihydroxy-7,8,9,10-tetrahycro-napthacene-5,12-dione (R162892, Sigma Aldrich). $^{15}N$ racemic and R-(+)-lipoamide were synthesised (see below) and characterised by $^{1}H$ NMR, $^{13}C$ NMR, mass spectrometry, infrared spectroscopy and melting point. Yield was ~50%, with $^{15}N$ label at ~99%.

Ex Vivo HeLa Cell Screen

The effect of compounds on FUS GFP localisation in stressed HeLa cells was screened in 384 well format. 4000 cells were seeded per well and incubated for 24 h, after which the medium was replaced with 40 µl fresh medium and compound added to a final concentration of 10 µM by acoustic dispensing (Labcyte Echo 550). The final concentration of DMSO in all samples was 0.1%. After 1 h potassium arsenate was added from a 5× stock solution to a final concentration of 1 mM and the cells incubated a further 1 h, then the cells were fixed with 7.4% formaldedhyde, stained with 1 mg/ml Hoechst 33342 and 1:10,000 CellMask blue (ThermoFisher). Six fields of view per well were captured using a CellVoyager CV7000 automated spinning disc confocal microscope (Yokogawa) using a 40× NA 1.3 water immersion objective. Each plate included 48 wells treated with 0.1% DMSO and stressed with arsenate (compound solvent control), along with 8 untreated unstressed wells and 4 unstressed untreated wells with parental Koyoto HeLa cells. All images are displayed at gamma 0.7 to show bright stress granules and faint nuclei simultaneously.

For the initial screen FUS GFP signal was analysed using KNIME. Cytoplasm was identified from weak (CellMask blue), and nuclei from strong (Hoechst 33342) blue fluorescent signal. Particle number and sum area, granularity at 9, 10 & 11 px (cytoplasm) or 1, 5, 6, 7, 8 & 9 px (nucleus) scale, texture at 10 px scale and integrated signal intensity were measured for the nucleus and cytoplasm in the green (FUS GFP) channel. Z scores ($z=(x-\mu)/\sigma$ where x is the observed value, $\mu$ the control mean and $\sigma$ the control standard deviation) relative to the DMSO treated control wells on each plate were calculated for each of the parameters, and combined into the Mahalanobis distance.

In Vitro Purified FUS GFP Screen

The effect of compounds on FUS GFP droplets in vitro was assessed in 384 well plate format. The compound volume (in DMSO) necessary for 1, 3, 10, 30 or 100 µM final concentration were added by acoustic dispensing (Labcyte Echo 550) to 96 well plate wells containing 3 µl FUS GFP diluted in 50 mM Tris. HCl pH 7.4, 1 mM DTT (for low salt assays). Final DMSO concentration was 0.01 to 1%. Using a Freedom Evo 200 liquid handling workstation (TECAN) the FUS GFP/compound mixture was diluted in 7 µl assay buffer containing 50 mM Tris. HCl pH 7.4, 1 mM DTT, 50 mM KCl and 0.7 µM FUS GFP. Compound/FUS GFP and assay buffer were mixed by a standardised pipetting procedure then split to four wells in clear bottom 384 well plates then immediately imaged using a CellVoyager CV7000 automated spinning disc confocal microscope (as above). Droplets in suspension for six fields of view were imaged as a maximum intensity projection of 6 focal planes at 2 µm steps per sample. Droplet number and FUS GFP partition into droplets were analysed with a fixed intensity threshold using ImageJ. Number of droplets and partition were weakly time dependent due to droplet sedimentation, so normalised assuming a linear change over time by reference to DMSO controls at the start and end of each plate row.

Compound Characterization on HeLa and iPS Cells

Compound effects were assessed under a variety of conditions in HeLa or iPS cells expressing wild-type or P525L FUS GFP by live cell imaging. Different combinations of 1 h pre-treatment compound or pre-stress with arsenate followed by 1 h treatment with compound and/or stress with arsenate. Unless otherwise indicated, cells were pre-treated for 1 h using 10 µM compound from 10 mM stock in DMSO (or an equal volume of DMSO control) then stressed for 1 h with 1 mM potassium arsenate still in the presence of compound. GFP fluorescence was imaged by widefield epifluorescence using an inverted Olympus IX71 microscope with an Olympus 100× NA 1.4 Plan Apo oil immersion objective and a CoolSNAP HQ CCD camera (Photometrics), using a DeltaVision climate control unit (37° C., 5% $CO_2$) (Applied Precision). The kinetics of pre-stress followed by treatment was analysed from images captured at 2 min intervals for 100 min, for single time points images were captured after 1 h unless otherwise indicated.

Various cellular stresses were achieved by replacing 1 h 1 mM potassium arsenate treatment with other conditions: 100 µM rotenone (R8875, Sigma Aldrich) from a 1 M stock in DMSO for 2 h (mitochondrial stress). Serum-free DMEM for 2.5 h (serum starvation stress). Sorbitol (S1876, Sigma Aldrich) from a 4 M stock in $H_2O$ for 1 h (osmotic stress). 42° C. in normal growth medium for 30 m (heat stress). 100 mM 6-deoxyglucose (D9761, Sigma Aldrich) from a 1 M stock in $H_2O$ in glucose free DMEM (11966025, ThermoFisher Scientific) supplemented with 10% FCS for 1 h (glycolysis stress). Appropriate solvent controls were used.

For Western blots and analysis of intracellular FUS aggregates iPS cells were lysed with RIPA buffer. Western blots were performed using standard methods and the following antibodies: Mouse anti-FUS (AMAB90549 Sigma Aldrich, 1:500 dilution), rabbit anti-GFP (sc-8334 Santa Cruz, 1:400) or rabbit anti-GAPDH (2118S NEB, 1:5000) primary antibody with horseradish peroxidase-conjugated anti-mouse or anti-rabbit (Dianova 1:10,000) secondary antibodies. The filter retardation assay for intracellular FUS aggregates was performed as previously described[56]. Briefly, protein extract were loaded on 0.2 µm cellulose acetate membrane then subject to microfiltration, leaving aggregated protein on the membrane. Aggregated FUS was detected as above.

HeLa Cell Compound Dose Responses

Dose dependent effect of compounds on HeLa or iPS cells expressing FUS GFP were assessed using 1 h 1 mM potassium arsenate stress as for the ex vivo HeLa cell screen, except serial compound dilutions in medium were prepared manually from 80 µM to ~0.4 nM at 1.189× dilution steps. Small dilution steps rather than concentration replicates were selected as it provides greater statistical power from a set number of samples. Final DMSO concentration was 0.08% in all samples, and each plate included at least 12 control wells with 0.08% DMSO. Cytoplasmic FUS droplet number and nuclear/cytoplasm partition of FUS were analysed using custom macros in ImageJ. Nuclei were identified by intensity thresholding of the blue fluorescence image following a 5 px Gaussian blur. Cytoplasmic FUS droplets by intensity thresholding of the green image following a 10 px weight 0.9 unsharp filter masked by the thresholded nuclei, and nuclear FUS droplets by intensity thresholding of the green image following a 5 px weight 0.9 unsharp filter and 10 px rolling ball background subtraction masked to only include thresholded nuclei. The ratio of cytoplasmic FUS drops to nuclei was taken as cytoplasmic FUS droplets per cell per field of view, and p, the ratio of partition of FUS to the nucleus and the cytoplasm, was derived from $a=V_n/v_t$, the ratio of nuclear to total green signal per field of view, where $p=a/(1-a)$. These data were log transformed and fitted to a Rodbard sigmoidal curve to determine $EC_{50}$. Six fields of view were captured and analysed per condition.

In Vitro FUS GFP Solidification Assays

For in vitro solidification assays, FUS GFP in storage buffer was diluted in water to give 10 µM FUS, 50 mM Tris·HCl pH 7.4 and 1 mM DTT in a 20 µl volume in non-binding clear bottom 384 well plates (Greiner Bio-One, 781906). Compounds, or an equal volume of DMSO, were then added for a final compound concentration of 30 µM and 0.3% DMSO. 'Aging' to cause fibre was induced by horizontal shaking at 800 rpm at room temperature. Fibre and droplet formation were analysed by widefield epifluorescence using a DeltaVision Elite microscope (GE Healthcare Life Sciences) with a Plan ApoN 60× NA 1.4 oil immersion objective (Olympus) and an sCMOS camera (PCO). For salt sensitivity of droplet formation FUS GFP in storage buffer was diluted in the appropriate concentration of KCl premixed with compound or DMSO to generate the final KCl concentration series with 30 µM compound concentration and 0.3% DMSO.

Fluorescence recovery after photobleaching (FRAP) of FUS GFP droplets and fibres was performed on a Nikon TiE inverted microscope with a Nikon Apo 100× NA 1.49 oil immersion objective using a Yokogawa CSU-X1 spinning disc head and an Andor iXon EM+ DU-897 EMCCD camera. 10×10 px regions were bleached for 50 ns with a 6 mW 405 nm laser using an Andor FRAPPA beam delivery unit then imaged for 5 min at 5 Hz. Recovery curve half-life and mobile fraction were calculated in ImageJ.

Ex Vivo DNA Cut Assays

UV micro-irradiation of live cells was performed to induce DNA damage. KOLF iPS MNs expressing wild-type GFP were stressed by addition of 1 mM potassium arsenate for 1 h, then were treated with lipoamide, mitoxantrone or an equal volume of DMSO for 1 h. A single point in the nucleus was subject to 3 UV pulses as described for FRAP, but at 10% laser power. GFP fluorescence was imaged at 1 Hz, and intensity of response was analysed in ImageJ.

NMR

For analysis of compound interaction with FUS untagged FUS low complexity domain (residues 1 to 163) expressed, purified and analysed using $^1$H-$^{15}$N heteronuclear single quantum coherence NMR and sample conditions previously described[14] in the presence of 500 µM compound or equivalent DMSO solvent control (1%).

For analysis of $^{15}$N lipoamide uptake by cells HeLa cells expressing FUS GFP were grown in 6 well plates to $10^6$ cells/well in DMEM supplemented with 10% FCS. To simultaneously stress and treat cells, the medium was replaced with 0.6 ml medium supplemented with potassium arsenate and 100 µM $^{15}$N racemic or R-(+)-lipoamide for 1 h at 37° C. High concentrations of compound were used to maximise the signal. The medium was then removed and retained (medium sample), the cells washed with ~2 ml PBS, then the cells removed by trypsinisation: Addition of 0.3 ml TrypLE Express (12604013, ThermoFisher) and incubation at 37° C. for 5 min, then addition of 0.3 ml medium to quench the trypsin. The resuspended cells were retained (cell sample). All samples were frozen at −80° C. Wells were prepared for all combinations of no compound (1% DMSO control), $^{15}$N (+)-lipoamide or $^{15}$N R-(+)-lipoamide, with or without potassium arsenate and with or without cells. $^1$H detected $^{15}$N edited $^1$H sensitivity enhanced HSQ was used to quantify $^{15}$N lipoamide concentration (see Supplementary Information). Solvent, pH and temperature sensitivity of the primary amide proton chemical shifts were determined using dummy samples assembled from the appropriate solvent and added compounds.

Neuron Dieback and Axonal Transport Assays

For analysis of axon dieback transport AH-ALS1-F58 iPS MNs expressing P525L FUS or an isogenic control expressing WT FUS were grown with 2 µM compound or an equal volume of DMSO for 60 days. Over this length of culture neurons expressing WT FUS have stable axons, while neurons expressing P525L FUS do not. Axon dieback is visible as accumulated cell detritus at the exit of axons from channels. Experiments and analysis were performed blinded, and axonal dieback was scored qualitatively using phase contrast images captured every 10 to 20 days.

For analysis of axonal transport iPS MNs expressing P525L FUS were treated with 2 µM compound or an equal volume of DMSO for 3 days. Longer incubation was selected to ensure penetration and action of compounds along the length of the axon channel. 2 µM was selected as the highest concentration where there were no toxic effects (assessed qualitatively). Analysis of axonal transport of liposomes were performed as follows: liposomes were labelled by addition of 50 nM lysotracker red (ThermoFisher) and imaged using a Leica DMI6000 inverted microscope with a 100× NA 1.46 oil immersion objective and an Andor iXON 897 EMCCD camera in an incubator chamber (37° C., 5% $CO_2$) at 3⅓ Hz for 120 s at either the proximal or distal end of the silicone channels containing the axons. Particle tracking was used to identify proportion of particles moving faster than 0.2 µm/s for five videomicrographs. Each video includes a variable population of non-moving background particles, therefore, for each biological replicate data were normalised to the mean proportion of fast moving lysosomes in the DMSO (solvent control) treated samples.

Protein Aggregation in C. elegans

The effect of lipoic acid on stress granule protein aggregation in vivo was analysed using a C. elegans model for stress granule formation and aggregation. As previously described, fluorescent-tagged PAB-1 forms abundant stress granules and large solid aggregates during aging or upon chronic stress. RHO-1 and KIN-19 also aggregate during aging, but are not RNA binding or stress granule proteins. Three lines were used: Fluorescently tagged PAB-1 (DCD214: N2; uqIs24[pmyo-2::tagrfp::pab 1gene]), KIN-19 (CF3649: N2; muIs 209[pmyo-3::kin-19::tagrfp+ptph-1:: GFP] and RHO-1 (DCD13: N2; uqIs9 [pmyo-2::rho-1::tagr fp+ptph-1::gfp]). Each were analysed as below, except DCD13 were maintained at 20° C.

The animals were exposed to lipoic acid in liquid culture in a 96 well plate starting from larval stage L4 in a total volume of 50 µl S-Complete per well (100 mM NaCl, 50 mM Potassium phosphate pH 6, 10 mM potassium citrate, 3 mM $MgSO_4$, 3 mM $CaCl_2$), 5 µg/mL cholesterol, 50 µM ethylenediaminetetraacetic acid (EDTA), 25 µM FeSO4, 10 µM $MnCl_2$, 10 µM $ZnSO_4$, 1 µM $CuSO_4$) supplemented with heat-killed OP50 and 50 µg/ml carbenicillin. Per experiment, a minimum of nine wells each with 13 animals were treated with R-(+)- or S-(−)-lipoic acid or an equivalent volume of DMSO. Toxicity was evaluated from the number of dead or aberrantly small-sized animals.

48 h after switching the L4s from 20° C. to 25° C. (day 2 of adulthood) extensive aggregation of fluorescently tagged PAB-1 and RHO-1 occurs in the pharyngeal muscles and KIN-19 throughout the animal. After immobilization with 2 mM levamisole aggregation was scored using a fluorescent stereo microscope (Leica M165 FC, Plan Apo 2.0× objective). For PAB-1, aggregates occurred primarily in the terminal bulb of the pharynx and aggregation was scored as high (>10 aggregates per animal) or low (<10). For RHO-1, aggregates were scored in the isthmus of the pharynx and aggregation was scored as high (>50% of the isthmus), medium (<50%) or low (no aggregation). For KIN-19 aggregates occurred throughout the body wall muscles and aggregation was scored as high (aggregates in the head, middle body and tail), medium (>15 aggregates in the head and middle body) or low (>15 aggregates in the head or middle body). High-magnification images were acquired with a Leica SP8 confocal microscope with a HC Plan Apo CS2 63× NA 1.40 oil objective using a Leica HyD hybrid detector. tagRFP::PAB-1 was detected using 555 nm as excitation and an emission range from 565-650 nm. Representative confocal images are displayed as maximum z stack projection.

Motor Defects in D. melanogaster

All Drosophila stocks were maintained on standard cornmeal at 25° C. in light/dark controlled incubator. The w1118, UAS-eGFP, and D42-GAL4 were obtained from Bloomington stock center. The UAS-FUS WT, UAS-FUS P525L, and UAS-FUS R521C were previously described in Anderson et al. (Hum. Mol. Genet. 27, 1366-1381, 2018).

Climbing assays were performed as previously described. Briefly, flies expressing FUS, eGFP or w1118 were grown in the presence or absence of (±)-α-Lipoic Acid (0.43 mM or 2.15 mM diluted in ethanol), (R)-(+)-α-Lipoic Acid (0.43 mM or 2.15 mM diluted in ethanol), (S)-(−)-α-Lipoic Acid (0.43 mM or 2.15 mM diluted in ethanol), (±)-α-Lipoamide (0.43 mM diluted in DMSO), or PP 242/Torkinib (10 µM or 50 μM diluted in DMSO), then anesthetised, placed into vials and allowed to acclimatise for 15 mins in new vials. For each fly genotype, the vial was knocked three times on the base on a bench and a video camera was used to record the flies climbing up the vial walls. The percentage of flies that climbed 4 cm in 30 s was recorded. Statistical analysis was carried out in GraphPad Prism 6 using either Student's T-test or one-way ANOVA with Tukey's or Dunnet's multiple comparisons test.

Synthesis and Characterisation of Racemic (±) and $^{15}$N R-(+)-lipoamide $^{15}$N (±)-Lipoamide

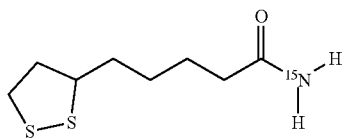 [SMILES: [15NH2]C(=O)CCCCC1CCSS1]

(±)-Lipoic acid (1.08 g, 5.24 mmol), N-Hydroxysuccinimide (660 mg, 5.60 mmol) and (1-ethyl-3-(3-dimethylaminopropyl) carbodiimide hydrochloride (1.1 g, 5.76 mmol) were stirred in DMF (20 ml) at 25° C. under argon atmosphere for 4 h. The solution was diluted with EtOAc (100 ml) and washed with H$_2$O (100 ml) and saturated aqueous NaHCO$_3$ (100 ml). The organic layer was dried over MgSO$_4$, filtered off and concentrated under reduced pressure. The NHS ester obtained, trimethylamine (1.1 ml, 7.89 mmol) and $^{15}$NH$_4$Cl (500 mg, 9.36 mmol) were dissolved in DCM (20 ml) and the mixture was stirred for 20 h. The solution was diluted with DCM (100 ml), washed with H$_2$O (100 ml), saturated aqueous NaHCO$_3$ (100 ml) and again with H$_2$O (100 ml, 2 times). The organic layer was dried over MgSO$_4$, filtered off and concentrated under reduced pressure to give crude $^{15}$N Lipoamide, which was further purified by silica gel column chromatography (DCM:MeOH=30:1). The solvent was removed under reduced pressure and $^{15}$N Lipoamide was obtained as yellow solid. Yield: 554.2 mg (51%). $^1$H NMR (400 MHZ, Chloroform-d) δ 5.62 (d, J=31.3 Hz, 1H, NH$_{cis}$), 5.37 (d, J=31.0 Hz, 1H, N$_{Htrans}$), 3.60 (ddt, 1H, SSCH), 3.26-3.06 (m, 2H, SSCH$_2$), 2.58-2.40 (m, 1H, SSCH$_2$CH$_{trans}$), 2.26 (t, J=7.5 Hz, 2H, CH$_2$CONH$_2$), 2.02-1.84 (m, 1H, SSCH$_2$CH$_{cis}$), 1.83-1.60 (m, 4H), 1.60-1.39 (m, 2H, CH$_2$CH$_2$CH$_2$CONH$_2$). 13C NMR (101 MHZ, Chloroform-d) & 175.02 (d, J=13.6 Hz, CONH$_2$), 56.39, 40.26, 38.49, 35.61, 35.53, 28.84, 25.14. ESI-MS: m/z=229.05 (M+Na)+. Electrospray (M+Na)+ ion detected. Data suggests $^{15}$N label is at ~99%. IR: 3352 cm$^{-1}$, 3176 cm$^{-1}$ (CONH$_2$), 2937 cm$^{-1}$, 2898 cm$^{-1}$, 2865 cm$^{-1}$, 2783 cm$^{-1}$ (C—H), 1746 cm$^{-1}$, 1650 cm$^{-1}$, 1629 cm$^{-1}$, 1464 cm$^{-1}$, 1413 cm$^{-1}$, 1367 cm$^{-1}$, 1342 cm$^{-1}$, 1321 cm 1, 1292 cm$^{-1}$, 1281 cm$^{-1}$, 1252 cm$^{-1}$, 1226 cm$^{-1}$, 1203 cm$^{-1}$, 1144 cm$^{-1}$, 1125 cm$^{-1}$, 1078 cm$^{-1}$, 1034 cm$^{-1}$, 999 cm$^{-1}$, 950 cm$^{-1}$, 911 cm$^{-1}$, 868 cm$^{-1}$, 803 cm$^{-1}$, 734 cm$^{-1}$, 675 cm$^{-1}$, 629 cm$^{-1}$ (C=O). Melting point: 130° C., Rf=0.60 (DCM:MeOH=20:1).

$^{15}$N R-(+)-Lipoamide

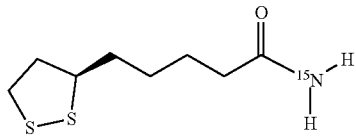 [SMILES: [15NH2]C(=O)CCCC[C@@H]1CCSS1]

R-(+)-Lipoic acid (1.08 g, 5.24 mmol), N-Hydroxysuccinimide (660 mg, 5.60 mmol) and (1-ethyl-3-(3-dimethylaminopropyl) carbodiimide hydrochloride (1.1 g, 5.76 mmol) were stirred in DMF (20 ml) at 25° C. under argon atmosphere for 4 h. The solution was diluted with EtOAc (100 ml) and washed with H$_2$O (100 ml) and saturated aqueous NaHCO$_3$ (100 ml). The organic layer was dried over MgSO$_4$, filtered off and concentrated under reduced pressure. The NHS ester obtained, trimethylamine (1.1 ml, 7.89 mmol) and $^{15}$NH$_4$Cl (500 mg, 9.36 mmol) were dissolved in DCM (20 ml) and the mixture was stirred for 20 h. The solution was diluted with DCM (100 ml), washed with H$_2$O (100 ml), saturated aqueous NaHCO$_3$ (100 ml) and again with H$_2$O (100 ml, 2 times). The organic layer was dried over MgSO$_4$, filtered off and concentrated under reduced pressure to give crude $^{15}$N Lipoamide, which was further purified by silica gel column chromatography (DCM:MeOH=30:1). The solvent was removed under reduced pressure and $^{15}$N (R)-Lipoamide was obtained as yellow solid. Yield: 554.5 mg (51%). $^1$H NMR (400 MHZ, Chloroform-d) δ 5.56 (d, J=4.1 Hz, 1H, NH$_{cis}$), 5.34 (d, J=4.7 Hz, 1H, NH$_{trans}$), 3.60 (ddt, 1H, SSCH), 3.30-3.03 (m, 2H, SSCH$_2$), 2.61-2.35 (m, 1H, SSCH$_2$CH$_{trans}$), 2.32-2.18 (m, 2H, CH$_2$CONH$_2$), 1.94 (m, 1H, SSCH$_2$CH$_{cis}$), 1.81-1.59 (m, 4H), 1.59-1.41 (m, 2H, CH$_2$CH$_2$CH$_2$CONH$_2$). 13C NMR (101 MHZ, Chloroform-d) δ 174.90 (d), 56.40, 40.26, 38.50, 35.60, 35.52, 34.64, 28.85, 25.14. ESI-MS: m/z=207.06 (M+H+). Electrospray (M+H+) ion detected. Data suggests $^{15}$N label is at ~99%. IR: 3340 cm$^{-1}$, 3174 cm$^{-1}$ (CONH$_2$), 2936 cm$^{-1}$, 2921 cm$^{-1}$, 2865 cm$^{-1}$, 2850 cm$^{-1}$ (C—H), 2788 cm$^{-1}$, 2550 cm$^{-1}$, 2360 cm$^{-1}$, 2341 cm$^{-1}$, 2161 cm$^{-1}$, 2036 cm$^{-1}$, 1751 cm$^{-1}$, 1650 cm$^{-1}$, 1627 cm$^{-1}$ (C=O), 1461 cm 1, 1411 cm$^{-1}$, 1369 cm$^{-1}$, 1343 cm$^{-1}$, 1317 cm$^{-1}$, 1294 cm$^{-1}$, 1260 cm$^{-1}$, 1213 cm$^{-1}$, 1197 cm$^{-1}$, 1135 cm$^{-1}$, 1036 cm$^{-1}$, 1004 cm$^{-1}$, 914 cm$^{-1}$, 878 cm$^{-1}$, 808 cm$^{-1}$, 794 cm$^{-1}$. Melting point: 121.5° C., Rf=0.60 (DCM:MeOH=20:1), [α]$^{25}$+105.6 (c=2.0, CHCl$_3$).

Density functional theory (DFT) calculations were performed to confirm assignment of the lipoamide $^1$H NMR spectrum. An optimised structure for lipoamide was generated using Gaussian098 from which shielding tensors were calculated, enabling isotropic and anisotropic components to be determined. DFT calculations used the B3LYP density functional with the 6-31G (d) basis set[72]. DFT calculations confirmed that the cis-amide proton 13 should have a larger chemical shift than the trans-amide proton 14 (FIG. 13A), and that the proton bound to carbon 3 closest in proximity to the proton bound to carbon 2 should have a larger chemical shift than the other proton on carbon 3 (FIG. 13A).

($^{15}$N) $^1$H NMR of $^{15}$N Lipoamide $^1$H detected $^{15}$N edited $^1$H sensitivity enhanced HSQC NMR (referred to here as ($^{15}$N) $^1$H) spectra were acquired on a narrow bore Varian solution state spectrometer operating with a fixed field strength of 14.1 T, equipped with a room-temperature probe.

The free induction decay was recorded for an acquisition time of 0.0624 and a sweep with of 8 kHz recorded over 1000 and a recovery delays of 1 s. Typically, 10000 transients were collected giving a total experiment time of 3 h 1 min. The J coupling between the amide protons and the $^{15}$N in H$_2$O samples was determined to be 96 Hz, and so the transfer times of 1/4 J in the INEPT portions of the pulse sequence were set to 2.6 ms. With these settings $^{15}$N ammonia or ammonium ions would not be detectable. Chemical modification of $^{15}$N lipoamide (including covalent attachment to an apoenzyme) would give a substantial change in the ($^{15}$N) $^1$H NMR spectrum. Similarly, dissolution of lipoamide in a phospholipid membrane would give substantial peak broadening in the cell samples. We observed neither, consistent with freely diffusing lipoamide.

Integrated NMR signal intensity is proportional to concentration, provided conditions (including ionic strength, buffer composition, temperature and pH) are identical[73]. Chemical exchange[74], expected as the amide protons in lipoamide should be labile in water, must also be accounted for. To ensure appropriate conditions were selected, ($^{15}$N) $^1$H NMR spectra were obtained in different solvents (Chloroform-d, H$_2$O, culture medium, medium with 3 mM KAsO$_2$ and a 50:50 mixture of medium with 3 mM KAsO$_2$ and EDTA-trypsin) (FIGS. 13B-13C). Only in pure water and Chloroform-d were both amide proton resonances of comparable signal intensity. In other solvents the cis-amide proton signal was reduced, suggesting chemical exchange (FIG. 13B), therefore the trans-amide proton was used for concentration quantitation. To determine temperature and pH sensitivity of the trans-amide proton signal ($^{15}$N) $^1$H spectra of 1 mM lipoamide in medium were acquired at different temperatures (FIG. 13D) and pH (FIG. 13E). Both amide protons showed chemical exchange under high temperature, high pH conditions, with the trans-amide proton affected more weakly (FIGS. 13D-13E). To determine whether lipoamide degrades over time the signal from the trans-amide proton was monitored at 37° C. and 10° C. for 10 h. At 37° C., but not 10° C., the signal intensity decayed slowly (FIG. 13F), suggesting slow hydrolysis to form ammonia. At 10° C. and below pH 8.6 the integrated signal from the trans-amide proton resonance is therefore a good measure of $^{15}$N lipoamide concentration.

Cellular uptake was measured by comparing the signal intensity S of the trans-amide proton of lipoamide acquired in the absence (—cells, sample i, FIG. 2A) and presence (+cells, sample ii, FIG. 2A) of HeLa cells. The measured fractional uptake U was given by:

$$U = 1 - \frac{S_{+cells}}{S_{-cells}}$$

The quantity (moles) of lipoamide added (add) becomes distributed between the intracellular (cell) and extracellular (out) environments following uptake. This can be expressed in terms of concentrations c and volumes V:

$$c_{add}V_{add} = c_{cell}V_{cell} + c_{out}V_{out}$$

The total volume of cells is given by $V_{cell} = V_1 N_{cell}$ where $V_1$ is the volume of a single cell and $N_{cell}$ is the number of cells. $V_{cell} \ll V_{add}$ so we assume $V_{add} = V$. The fractional uptake can also be written in terms of these concentrations and volumes:

$$U = 1 - \frac{c_{out}V_{out}}{c_{add}V_{add}}$$

Rearrangement gives expressions for the concentration inside and outside the cell in terms of the quantity of lipoamide added and the measured fractional uptake U.

$$C_{out} = (1-U)\frac{c_{add}V_{add}}{V_{out}}$$

-continued $$C_{cell} = U\frac{c_{add}V_{add}}{V_1 N_{cell}}$$

We approximate HeLa cells as spheres of radius $10^{-5}$ m $V_1 = 4.19 \times 10^{-15}$ m$^3$. In our experiment, $N_{cell} = 10^6$, $c_{add} = 100$ μM and $V_{add} = 600$ μl, respectively.

We saw no evidence for peak broadening which would be associated with dissolution in a phospholipid membrane, however in principle the lost signal intensity on uptake could be attributed to uptake into membranes rather than the cytoplasm.

Calculation suggests this is implausible. The number of phospholipid molecules in the plasma membrane can be estimated from the footprint of each lipid molecule $A_L = 0.5$ nm$^2$ [75]. Assuming a spherical cell, the surface area of a single cell is $A_1 = 1.3 \times 10^{-9}$ m$^2$. Therefore, the total number of phospholipid molecules taken up by cells $N_{uptake} = c_{cell}V_{cell}N_A$ where $N_A$ is Avogadro's number. The ratio R of lipoamide to lipid molecules is given by:

$$R = \frac{N_{uptake}}{N_L} = \frac{A_L N_A U c_{add} V_{add}}{A_1 N_{cell}}$$

For the mean experimentally observed U=0.35 (ie. 35% uptake) then we expect R=4.9, i.e. 4.9 lipoamide molecules per plasma membrane lipid molecule. The plasma membrane is not the only membrane in the cell, however even if it makes up 10% of total phospholipid there would need to be approximately 1 lipoamide molecule per 2 phospholipid molecule.

What is claimed is:

1. A method of identifying a compound that modulates a characteristic associated with one or more condensates comprising a condensate-associated molecule, the method comprising:
    (a) contacting the compound with a cellular composition comprising one or more condensates or a cellular composition capable of forming one or more condensates, and
    (b) determining the characteristic associated with the one or more condensates based on the number of the one or more condensates comprising the condensate-associated molecule, the cellular location of the one or more condensates, and the cellular distribution of the one or more condensates to identify the compound that modulates the characteristic associated with the one or more condensates,
    wherein a modulation in the characteristic, as compared to a reference, indicates that the compound modulates the characteristic associated with the one or more condensates.

2. The method of claim 1, wherein determining the characteristic associated with the one or more condensates is further based on any one or more of the following:
    (i) size of the one or more condensates;
    (ii) surface area of the one or more condensates;
    (iii) composition of the one or more condensates;
    (iv) liquidity of the one or more condensates;
    (v) solidification of the one or more condensates;
    (vi) dissolution of the one or more condensates;
    (vii) presence and/or amount of fiber formation;
    (viii) location of the condensate-associated molecule;
    (ix) partitioning of the condensate-associated molecule into the one or more condensates; or
    (x) aggregation of the condensate-associated molecule.

3. The method of claim 1, wherein the one or more condensates are within one or more cells in the cellular composition.

4. The method of claim 1, further comprising subjecting the cellular composition to a condensate-forming condition prior to step (b).

5. The method of claim 1, further comprising subjecting the cellular composition to a condensate-forming condition prior to step (a).

6. The method of claim 4, wherein the condensate-forming condition is any one or more of:
   (i) an oxidative stressor;
   (ii) a mitochondrial electron transport chain inhibitor;
   (iii) a heat stressor;
   (iv) an osmotic stressor;
   (v) a hyperosmotic stressor; and
   (vi) glycolysis inhibition.

7. The method of claim 1, wherein the condensate-associated molecule is a polypeptide.

8. The method of claim 1, wherein the condensate-associated molecule is a wildtype polypeptide.

9. The method of claim 1, wherein the condensate-associated molecule is a mutant polypeptide.

10. The method of claim 1, wherein the condensate-associated molecule is selected from the group consisting of: FUS, EWSR1, TIAL1, PABPC1, and G3BP1.

11. The method of claim 1, wherein a cell in the cellular composition expresses the condensate-associated molecule.

12. The method of claim 1, wherein the cellular composition comprises a HeLA, iPSC, or iPSC MN cell.

13. The method of claim 1, further comprising imaging at least a portion of the cellular composition.

14. The method of claim 1, further comprising contacting at least a portion of the cellular composition with a fixative.

15. The method of claim 1, further comprising contacting at least a portion of the cellular composition with a stain.

16. The method of claim 1, further comprising contacting at least a portion of the cellular composition with a DNA-damaging condition.

17. The method of claim 16, wherein the DNA-damaging condition is laser irradiation.

18. The method of claim 1, wherein the reference is a second condensate.

19. The method of claim 1, wherein the reference is a second cellular composition.

20. The method of claim 1, further comprising assessing the identified compound using a second cell-based assay.

21. The method of claim 1, further comprising assessing the identified compound using a biochemical assay.

22. The method of claim 1, wherein the cellular distribution is based on the ratio of the one or more condensates comprising the condensate-associated molecule in the nucleus versus the cytoplasm.

* * * * *